(12) United States Patent
Saito et al.

(10) Patent No.: US 10,620,109 B2
(45) Date of Patent: Apr. 14, 2020

(54) METHOD FOR SELECTING SKELETAL MUSCLE PROGENITOR CELL

(71) Applicant: KYOTO UNIVERSITY, Kyoto-shi, Kyoto (JP)

(72) Inventors: Hirohide Saito, Kyoto (JP); Seiya Takahashi, Kyoto (JP); Hidetoshi Sakurai, Kyoto (JP); Takahiko Sato, Kyoto (JP); Satoru Takayama, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/543,513

(22) PCT Filed: Jan. 14, 2016

(86) PCT No.: PCT/JP2016/050997
§ 371 (c)(1),
(2) Date: Jul. 13, 2017

(87) PCT Pub. No.: WO2016/114354
PCT Pub. Date: Jul. 21, 2016

(65) Prior Publication Data
US 2017/0370821 A1 Dec. 28, 2017

(30) Foreign Application Priority Data
Jan. 14, 2015 (JP) ................. 2015-005447

(51) Int. Cl.
*G01N 15/14* (2006.01)
*C12N 5/10* (2006.01)
*G01N 21/64* (2006.01)

(52) U.S. Cl.
CPC .......... *G01N 15/1434* (2013.01); *C12N 5/10* (2013.01); *G01N 21/6428* (2013.01); *G01N 2015/149* (2013.01); *G01N 2021/6439* (2013.01)

(58) Field of Classification Search
CPC ..... C12N 5/10; C12N 15/85; C12N 2310/141
See application file for complete search history.

(56) References Cited

U.S. PATENT DOCUMENTS

| 2004/0110286 A1* | 6/2004 | Bhatia .................. C12N 5/0647 435/366 |
| 2010/0292297 A1 | 11/2010 | Wang et al. |
| 2010/0323356 A1 | 12/2010 | Inoue et al. |
| 2012/0115150 A1 | 5/2012 | Bozzoni et al. |
| 2013/0150256 A1 | 6/2013 | Synnergren et al. |
| 2014/0370537 A1 | 12/2014 | Sakurai et al. |

FOREIGN PATENT DOCUMENTS

| EP | 3121276 A1 | 1/2017 |
| WO | WO 2007/070483 A2 | 6/2007 |
| WO | WO 2010/008100 A1 | 1/2010 |
| WO | WO 2010/136415 A1 | 12/2010 |
| WO | WO 2011/154553 A2 | 12/2011 |
| WO | WO 2013/073246 A1 | 5/2013 |
| WO | WO 2015/141827 A1 | 9/2015 |
| WO | WO 2016/108288 A1 | 7/2016 |

OTHER PUBLICATIONS

Meyer et al. Cell Communication and Signaling 13:4, pp. 1-14 (Year: 2015).*
Miyagoe-Suzuki et al. World J Stem Cells, 9:89-97 (Year: 2017).*
Guller et al. J Physiol 588 21 2010, 4075-4087 (Year: 2010).*
Tanaka et al. PLOS One 8: e61540, pp. 1-14 (Year: 2013).*
Miki et al., "Efficient Detection and Purification of Cell Populations Using Synthetic MicroRNA Switches," *Cell Stem Cell*, 16(6): 699-711 and Graphical Abstract (2015).
Mizuno et al., "Generation of skeletal muscle stem/progenitor cells from murine induced pluripotent stem cells," *FASEB J.*, 24(7): 2245-2253 (2010).
Shelton et al., "Derivation and Expansion of PAX7-Positive Muscle Progenitors from Human and Mouse Embryonic Stem Cells," *Stem Cell Reports*, 3(3): 516-529 (2014).
Townley-Tilson et al., "MicroRNAs 1, 133, and 206: Critical factors of skeletal and cardiac muscle development, function, and disease," *Int. J. Biochem. Cell Biol.*, 42(8): 1252-1255 (2010).
Japanese Patent Office, International Search Report in International Patent Application No. PCT/JP2016/050997 (dated Apr. 19, 2016).
Mahmood et al., "Enhanced Differentiation of Human Embryonic Stem Cells to Mesenchymal Progenitors by Inhibition of TGF-β/Activin/Nodal Signaling Using SB-431542," *J. Bone Miner. Res.*, 25(6): 1216-1233 (2010).
Brown et al., "Endogenous microRNA regulation suppresses transgene expression in hematopoietic lineages and enables stable gene transfer," *Nat. Med.*, 12(5): 585-591 (2006).
Sachdeva et al., "Tracking differentiating neural progenitors in pluripotent cultures using microRNA-regulated lentiviral vectors," *Proc. Natl. Acad. Sci. U.S.A.*, 107(25): 11602-11607 and Supporting Information [4 pages] (2010).
European Patent Office, Communication Pursuant to Article 94(3) EPC in European Patent Application No. 16737425.5 (dated May 23, 2019).
European Patent Office, Extended European Search Report in European Patent Application No. 16737425.5 (dated May 8, 2018).
Kato et al., "Real-time functional imaging for monitoring miR-133 during myogenic differentiation," *Int. J. Biochem. Cell Biol.*, 41(11): 2225-2231 (2009).

* cited by examiner

*Primary Examiner* — Brian Whiteman
(74) *Attorney, Agent, or Firm* — Leydig, Voit & Mayer, Ltd.

(57) ABSTRACT

The present invention aims to provide a method of sorting a skeletal muscle progenitor cell from a cell population containing the skeletal muscle progenitor cell. The above-mentioned problem is solved by providing a step of introducing miRNA-responsive mRNA into a cell population. The miRNA-responsive mRNA contains (i) a nucleic acid having a sequence specifically recognized by miRNA specifically expressed in a skeletal muscle progenitor cell, and (ii) a nucleic acid containing a sequence encoding a marker protein.

20 Claims, 7 Drawing Sheets

Specification includes a Sequence Listing.

SEQUENCE LISTING

<160> NUMBER OF SEQ ID NOS: 62

<210> SEQ ID NO 1
<211> LENGTH: 22
<212> TYPE: RNA
<213> ORGANISM: Homo sapiens

<400> SEQUENCE: 1
uggaauguaa agaaguaugu au          22

<210> SEQ ID NO 2
<211> LENGTH: 22
<212> TYPE: RNA
<213> ORGANISM: Homo sapiens

<400> SEQUENCE: 2 uuugguccccc uucaaccagc ug         22

<210> SEQ ID NO 3
<211> LENGTH: 22
<212> TYPE: RNA
<213> ORGANISM: Homo sapiens

<400> SEQUENCE: 3
uggaauguaa ggaagugugu gg          22

<210> SEQ ID NO 4
<211> LENGTH: 22
<212> TYPE: RNA
<213> ORGANISM: Homo sapiens

<400> SEQUENCE: 4
auacauacuu cuuuacauuc ca          22

```
<210> SEQ ID NO 5
<211> LENGTH: 22
<212> TYPE: RNA
<213> ORGANISM: Homo sapiens

<400> SEQUENCE: 5
cagcugguug aagggggacca aa                                              22

<210> SEQ ID NO 6
<211> LENGTH: 22
<212> TYPE: RNA
<213> ORGANISM: Homo sapiens

<400> SEQUENCE: 6
ccacacacuu ccuuacauuc ca                                               22

<210> SEQ ID NO 7
<211> LENGTH: 65
<212> TYPE: RNA
<213> ORGANISM: Artificial Sequence
<220> FEATURE:
<223> OTHER INFORMATION: Synthetic cassette

<400> SEQUENCE: 7
gguuccuuaa ucgcggaucc auacauacuu cuuuacauuc caagaucaca ccggucgcca       60
ccaug                                                                  65

<210> SEQ ID NO 8
<211> LENGTH: 65
<212> TYPE: RNA
<213> ORGANISM: Artificial Sequence
<220> FEATURE:
<223> OTHER INFORMATION: Synthetic cassette

<400> SEQUENCE: 8
gguuccuuaa ucgcggaucc cagcugguug aagggggacca aagaucaca ccggucgcca       60 ccaug                                                                  65

<210> SEQ ID NO 9
<211> LENGTH: 65
<212> TYPE: RNA
<213> ORGANISM: Artificial Sequence
<220> FEATURE:
<223> OTHER INFORMATION: Synthetic cassette

<400> SEQUENCE: 9
gguuccuuaa ucgcggaucc ccacacacuu ccuuacauuc caagaucaca ccggucgcca       60
ccaug                                                                  65

<210> SEQ ID NO 10
<211> LENGTH: 212
<212> TYPE: RNA
<213> ORGANISM: Artificial Sequence
<220> FEATURE:
<223> OTHER INFORMATION: Synthetic cassette

<400> SEQUENCE: 10
ucuagaccuu cugcggggcu ugccuucugg ccaugcccuu cuucucuccc uugcaccugu       60
accucuuggu cuuugaauaa agccugagua ggaaaaaaaa aaaaaaaaaa aaaaaaaaaa      120
aaaaaaaaaa aaaaaaaaaa aaaaaaaaaa aaaaaaaaaa aaaaaaaaaa aaaaaaaaaa      180
aaaaaaaaaa aaaaaaaaaa aaaaaaaaaa aa                                   212
```

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
caccggtcgc caccatggga tccgtgagca agggc                          35

<210> SEQ ID NO 12
<211> LENGTH: 29
<212> TYPE: DNA
<213> ORGANISM: Artificial Sequence
<220> FEATURE:
<223> OTHER INFORMATION: primer

<400> SEQUENCE: 12
caccggtcgc caccatggga tccagcgag                                 29

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
caccggtcgc caccatggga tccgtgtcta ag                             32

<210> SEQ ID NO 14
<211> LENGTH: 45
<212> TYPE: DNA
<213> ORGANISM: Artificial Sequence
<220> FEATURE:
<223> OTHER INFORMATION: primer

<400> SEQUENCE: 14
gccccgcaga aggtctagac tatcactcga gatgcatatg agatc               45

<210> SEQ ID NO 15
<211> LENGTH: 783
<212> TYPE: DNA
<213> ORGANISM: Artificial Sequence
<220> FEATURE:
<223> OTHER INFORMATION: Synthetic cassette

<400> SEQUENCE: 15
caccggtcgc caccatggga tccgtgagca agggcgagga gctgttcacc ggggtggtgc    60
ccatcctggt cgagctggac ggcgacgtaa acggccacaa gttcagcgtg tccggcgagg   120
gcgagggcga tgccacctac ggcaagctga ccctgaagtt catctgcacc accggcaagc   180
tgcccgtgcc ctggcccacc ctcgtgacca cctgacccta cggcgtgcag tgcttcagcc   240
gctaccccga ccacatgaag cagcacgact tcttcaagtc cgccatgccc gaaggctacg   300
tccaggagcg caccatcttc ttcaaggacg acggcaacta caagacccgc gccgaggtga   360
agttcgaggg cgacaccctg gtgaaccgca tcgagctgaa gggcatcgac ttcaaggagg   420
acggcaacat cctggggcac aagctggagt acaactacaa cagccacaac gtctatatca   480
tggccgacaa gcagaagaac ggcatcaagt gaacttcaa gatccgccac aacatcgagg   540
acggcagcgt gcagctcgcc gaccactacc agcagaacac ccccatcggc gacggccccg   600

-continued

| | |
|---|---|
| tgctgctgcc cgacaaccac tacctgagca cccagtccgc cctgagcaaa gaccccaacg | 660 |
| agaagcgcga tcacatggtc ctgctggagt tcgtgaccgc cgccgggatc actctcggca | 720 |
| tggacgagct gtacaagaga tctcatatgc atctcgagtg atagtctaga ccttctgcgg | 780 |
| ggc | 783 |

<210> SEQ ID NO 16
<211> LENGTH: 756
<212> TYPE: DNA
<213> ORGANISM: Artificial Sequence
<220> FEATURE:
<223> OTHER INFORMATION: Synthetic cassette

<400> SEQUENCE: 16

| | |
|---|---|
| caccggtcgc caccatggga tccagcgagc tgattaagga gaacatgcac atgaagctgt | 60 |
| acatggaggg caccgtggac aaccatcact tcaagtgcac atccgagggc gaaggcaagc | 120 |
| cctacgaggg cacccagacc atgagaatca aggtggtcga gggcggccct ctccccttcg | 180 |
| ccttcgacat cctggctact agcttcctct acggcagcaa gaccttcatc aaccacaccc | 240 |
| agggcatccc cgacttcttc aagcagtcct ccctgagggg cttcacatgg gagagagtca | 300 |
| ccacatacga gacggggggc gtgctgaccg ctacccagga caccagcctc caggacggct | 360 |
| gcctcatcta caacgtcaag atcagagggg tgaacttcac atccaacggc cctgtgatgc | 420 |
| agaagaaaac actcggctgg gaggccttca ccgagacgct gtaccccgct gacggcggcc | 480 |
| tggaaggcag aaacgacatg gccctgaagc tcgtgggcgg gagccatctg atcgcaaaca | 540 |
| tcaagaccac atatagatcc aagaaacccg ctaagaacct caagatgcct ggcgtctact | 600 |
| atgtggacta cagactggaa agaatcaagg aggccaacaa cgagacctac gtcgagcagc | 660 |
| acgaggtggc agtggccaga tactgcgacc tccctagcaa actggggcac agatctcata | 720 |
| tgcatctcga gtgatagtct agaccttctg cggggc | 756 |

<210> SEQ ID NO 17
<211> LENGTH: 777
<212> TYPE: DNA
<213> ORGANISM: Artificial Sequence
<220> FEATURE:
<223> OTHER INFORMATION: Synthetic cassette

<400> SEQUENCE: 17

| | |
|---|---|
| caccggtcgc caccatggga tccgtgtcta agggcgaaga gctgattaag gagaacatgc | 60 |
| acatgaagct gtacatggag ggcaccgtga caaccacca cttcaagtgc catccgagg | 120 |
| gcgaaggcaa gccctacgag ggcacccaga ccatgagaat caaggtggtc gagggcggcc | 180 |
| ctctcccctt cgccttcgac atcctggcta ccagcttcat gtacggcagc agaaccttca | 240 |
| tcaaccacac ccagggcatc cccgacttct ttaagcagtc cttccctgag ggcttcacat | 300 |
| gggagagagt caccacatac gaagacgggg gcgtgctgac cgctacccag acaccagcc | 360 |
| tccaggacgg ctgcctcatc tacaacgtca agatcagagg ggtgaacttc ccatccaacg | 420 |
| gccctgtgat gcagaagaaa acactcggct gggaggccaa caccgagatg ctgtaccccg | 480 |
| ctgacggcgg cctggaaggc agaagcgaca tggccctgaa gctcgtgggc ggggccacc | 540 |
| tgatctgcaa cttcaagacc atatacagat ccaagaaacc cgctaagaac ctcaagatgc | 600 |
| ccggcgtcta ctatgtggac cacagactgg aaagaatcaa ggaggccgac aaagagacct | 660 |
| acgtcgagca gcacgaggtg gctgtggcca gatactgcga cctccctagc aaactggggc | 720 |
| acaaacttaa tagatctcat atgcatctcg agtgatagtc tagaccttct gcggggc | 777 |

-continued

<210> SEQ ID NO 18
<211> LENGTH: 87
<212> TYPE: DNA
<213> ORGANISM: Artificial Sequence
<220> FEATURE:
<223> OTHER INFORMATION: Synthetic cassette

<400> SEQUENCE: 18
cagtgaattg taatacgact cactataggg cgaattaaga gagaaaagaa gagtaagaag    60
aaatataaga caccggtcgc caccatg                                       87

<210> SEQ ID NO 19
<211> LENGTH: 31
<212> TYPE: DNA
<213> ORGANISM: Artificial Sequence
<220> FEATURE:
<223> OTHER INFORMATION: primer

<400> SEQUENCE: 19
cagtgaattg taatacgact cactataggg c                                  31

<210> SEQ ID NO 20
<211> LENGTH: 37
<212> TYPE: DNA
<213> ORGANISM: Artificial Sequence
<220> FEATURE:
<223> OTHER INFORMATION: primer

<400> SEQUENCE: 20
catggtggcg accggtgtct tatatttctt cttactc                            37

<210> SEQ ID NO 21
<211> LENGTH: 87
<212> TYPE: DNA
<213> ORGANISM: Artificial Sequence
<220> FEATURE:
<223> OTHER INFORMATION: Synthetic cassette

<400> SEQUENCE: 21
cagtgaattg taatacgact cactataggg cgaattaaga gagaaaagaa gagtaagaag    60
aaatataaga caccggtcgc caccatg                                       87

<210> SEQ ID NO 22
<211> LENGTH: 77
<212> TYPE: DNA
<213> ORGANISM: Artificial Sequence
<220> FEATURE:
<223> OTHER INFORMATION: Synthetic cassette

<400> SEQUENCE: 22
cgactcacta taggttccgc gatcgcggat ccatacatac ttctttacat tccaagatca    60
caccggtcgc caccatg                                                  77

<210> SEQ ID NO 23
<211> LENGTH: 77
<212> TYPE: DNA
<213> ORGANISM: Artificial Sequence
<220> FEATURE:
<223> OTHER INFORMATION: Synthetic cassette

<400> SEQUENCE: 23
cgactcacta taggttccgc gatcgcggat cccagctggt tgaaggggac caaaagatca    60
caccggtcgc caccatg 77

<210> SEQ ID NO 24
<211> LENGTH: 77
<212> TYPE: DNA
<213> ORGANISM: Artificial Sequence
<220> FEATURE:
<223> OTHER INFORMATION: Synthetic cassette

<400> SEQUENCE: 24
cgactcacta taggttccgc gatcgcggat ccccacacac ttccttacat tccaagatca 60
caccggtcgc caccatg 77

<210> SEQ ID NO 25
<211> LENGTH: 77
<212> TYPE: DNA
<213> ORGANISM: Artificial Sequence
<220> FEATURE:
<223> OTHER INFORMATION: Synthetic cassette

<400> SEQUENCE: 25
cgactcacta taggttccgc gatcgcggat ccgctgccgt atatgtgatg tcacagatca 60
caccggtcgc caccatg 77

<210> SEQ ID NO 26
<211> LENGTH: 77
<212> TYPE: DNA
<213> ORGANISM: Artificial Sequence
<220> FEATURE:
<223> OTHER INFORMATION: Synthetic cassette

<400> SEQUENCE: 26
cgactcacta taggttccgc gatcgcggat ccccagcta gattgtaagc tccttagatc 60
caccggtcgc caccatg 77

<210> SEQ ID NO 27
<211> LENGTH: 92
<212> TYPE: DNA
<213> ORGANISM: Artificial Sequence
<220> FEATURE:
<223> OTHER INFORMATION: Synthetic cassette

<400> SEQUENCE: 27
tctagacctt ctgcggggct tgccttctgg ccatgccctt cttctctccc ttgcacctgt 60
acctcttggt ctttgaataa agcctgagta gg 92

<210> SEQ ID NO 28
<211> LENGTH: 19
<212> TYPE: DNA
<213> ORGANISM: Artificial Sequence
<220> FEATURE:
<223> OTHER INFORMATION: primer

<400> SEQUENCE: 28
tctagacctt ctgcggggc 19

<210> SEQ ID NO 29
<211> LENGTH: 48
<212> TYPE: DNA
<213> ORGANISM: Artificial Sequence
<220> FEATURE:
<223> OTHER INFORMATION: primer

<400> SEQUENCE: 29
tttttttttt tttttttttt cctactcagg ctttattcaa agaccaag    48

<210> SEQ ID NO 30
<211> LENGTH: 112
<212> TYPE: DNA
<213> ORGANISM: Artificial Sequence
<220> FEATURE:
<223> OTHER INFORMATION: Synthetic cassette

<400> SEQUENCE: 30
tctagacctt ctgcggggct tgccttctgg ccatgccctt cttctctccc ttgcacctgt    60
acctcttggt ctttgaataa agcctgagta ggaaaaaaaa aaaaaaaaaa aa    112

<210> SEQ ID NO 31
<211> LENGTH: 139
<212> TYPE: DNA
<213> ORGANISM: Artificial Sequence
<220> FEATURE:
<223> OTHER INFORMATION: primer

<400> SEQUENCE: 31
tttttttttt tttttttttt tttttttttt tttttttttt tttttttttt tttttttttt    60
tttttttttt tttttttttt tttttttttt tttttttttt tttttttttt tttttttttt    120
cctactcagg ctttattca    139

<210> SEQ ID NO 32
<211> LENGTH: 39
<212> TYPE: DNA
<213> ORGANISM: Artificial Sequence
<220> FEATURE:
<223> OTHER INFORMATION: Synthetic cassette

<400> SEQUENCE: 32
gctaatacga ctcactatag gttccttaat cgcggatcc    39

<210> SEQ ID NO 33
<211> LENGTH: 1046
<212> TYPE: DNA
<213> ORGANISM: Artificial Sequence
<220> FEATURE:
<223> OTHER INFORMATION: Synthetic DNA template

<400> SEQUENCE: 33
cagtgaattg taatacgact cactataggg cgaattaaga gagaaagaa gagtaagaag     60 aaatataaga caccggtcgc caccatggga tccgtgagca agggcgagga gctgttcacc    120
ggggtggtgc ccatcctggt cgagctggac ggcgacgtaa acggccacaa gttcagcgtg    180
tccggcgagg gcgagggcga tgccacctac ggcaagctga ccctgaagtt catctgcacc    240
accggcaagc tgcccgtgcc ctggcccacc ctcgtgacca ccctgaccta cggcgtgcag    300
tgcttcagcc gctaccccga ccacatgaag cagcacgact tcttcaagtc cgccatgccc    360
gaaggctacg tccaggagcg caccatcttc ttcaaggacg acggcaacta caagacccgc    420
gccgaggtga agttcgaggg cgacaccctg gtgaaccgca tcgagctgaa gggcatcgac    480
ttcaaggagg acggcaacat cctggggcac aagctggagt acaactacaa cagccacaac    540
gtctatatca tggccgacaa gcagaagaac ggcatcaagg tgaacttcaa gatccgccac    600
aacatcgagg acggcagcgt gcagctcgcc gaccactacc agcagaacac ccccatcggc    660
gacggccccg tgctgctgcc cgacaaccac tacctgagca cccagtccgc cctgagcaaa    720

```
gaccccaacg agaagcgcga tcacatggtc ctgctggagt tcgtgaccgc cgccgggatc    780
actctcggca tggacgagct gtacaagaga tctcatatgc atctcgagtg atagtctaga    840
ccttctgcgg ggcttgcctt ctggccatgc ccttcttctc tcccttgcac ctgtacctct    900
tggtctttga ataaagcctg agtaggaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaa                                        1046

<210> SEQ ID NO 34
<211> LENGTH: 1019
<212> TYPE: DNA
<213> ORGANISM: Artificial Sequence
<220> FEATURE:
<223> OTHER INFORMATION: Synthetic DNA template

<400> SEQUENCE: 34
cagtgaattg taatacgact cactataggg cgaattaaga gagaaaagaa gagtaagaag     60
aaatataaga caccggtcgc caccatggga tccagcgagc tgattaagga gaacatgcac    120
atgaagctgt acatggaggg caccgtggac aaccatcact tcaagtgcac atccgagggc    180
gaaggcaagc cctacgaggg cacccagacc atgagaatca aggtggtcga gggcggccct    240
ctccccttcg ccttcgacat cctggctact agcttcctct acggcagcaa gaccttcatc    300
aaccacaccc agggcatccc cgacttcttc aagcagtcct cccctgaggg cttcacatgg    360
gagagagtca ccacatacga agacggggc gtgctgaccg ctacccagga caccagcctc    420
caggacggct gcctcatcta caacgtcaag atcagagggg tgaacttcac atccaacggc    480
cctgtgatgc agaagaaaac actcggctgg gaggccttca ccgagacgct gtaccccgct    540
gacggcggcc tggaaggcag aaacgacatg gccctgaagc tcgtgggcgg gagccatctg    600
atcgcaaaca tcaagaccac atatagatcc aagaaacccg ctaagaacct caagatgcct    660
ggcgtctact atgtggacta cagactggaa agaatcaagg aggccaacaa cgagacctac    720
gtcgagcagc acgaggtggc agtggccaga tactgcgacc tccctagcaa actggggcac    780
agatctcata tgcatctcga gtgatagtct agaccttctg cggggcttgc cttctggcca    840
tgcccttctt ctctcccttg cacctgtacc tcttggtctt tgaataaagc ctgagtagga    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaa   1019

<210> SEQ ID NO 35
<211> LENGTH: 1040
<212> TYPE: DNA
<213> ORGANISM: Artificial Sequence
<220> FEATURE:
<223> OTHER INFORMATION: Synthetic DNA template

<400> SEQUENCE: 35
cagtgaattg taatacgact cactataggg cgaattaaga gagaaaagaa gagtaagaag     60
aaatataaga caccggtcgc caccatggga tccgtgtcta agggcgaaga gctgattaag    120
gagaacatgc acatgaagct gtacatggag ggcaccgtga acaaccacca cttcaagtgc    180
acatccgagg gcgaaggcaa gccctacgag ggcacccaga ccatgagaat caaggtggtc    240
gagggcggcc ctctcccctt cgccttcgac atcctggcta ccagcttcat gtacggcagc    300
agaaccttca tcaaccacac ccagggcatc cccgacttct ttaagcagtc cttccctgag    360
ggcttcacat gggagagagt caccacatac gaagacgggg cgtgctgac cgctacccag    420
```

```
gacaccagcc tccaggacgg ctgcctcatc tacaacgtca agatcagagg ggtgaacttc    480
ccatccaacg gccctgtgat gcagaagaaa acactcggct gggaggccaa caccgagatg    540
ctgtaccccg ctgacggcgg cctggaaggc agaagcgaca tggccctgaa gctcgtgggc    600
gggggccacc tgatctgcaa cttcaagacc acatacagat ccaagaaacc cgctaagaac    660
ctcaagatgc ccggcgtcta ctatgtggac cacagactgg aaagaatcaa ggaggccgac    720
aaagagacct acgtcgagca gcacgaggtg gctgtggcca gatactgcga cctccctagc    780
aaactggggc acaaacttaa tagatctcat atgcatctcg agtgatagtc tagaccttct    840
gcggggcttg ccttctggcc atgcccttct tctctcccct tgcacctgta cctcttggtct   900 ttgaataaag cctgagtagg aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa                                               1040
```

<210> SEQ ID NO 36
<211> LENGTH: 1043
<212> TYPE: DNA
<213> ORGANISM: Artificial Sequence
<220> FEATURE:
<223> OTHER INFORMATION: Synthetic DNA template

<400> SEQUENCE: 36

```
gctaatacga ctcactatag gttccttaat cgcggatccc cacacacttc cttacattcc     60
aagatcacac cggtcgccac catgggatcc gtgagcaagg gcgaggagct gttcaccggg    120
gtggtgccca tcctggtcga gctggacggc gacgtaaacg gccacaagtt cagcgtgtcc    180
ggcgagggcg agggcgatgc cacctacggc aagctgaccc tgaagttcat ctgcaccacc    240
ggcaagctgc ccgtgccctg gcccaccctc gtgaccaccc tgacctacgg cgtgcagtgc    300
ttcagccgct accccgacca catgaagcag cacgacttct tcaagtccgc catgcccgaa    360
ggctacgtcc aggagcgcac catcttcttc aaggacgacg gcaactacaa gacccgcgcc    420
gaggtgaagt tcgagggcga caccctggtg aaccgcatcg agctgaaggg catcgacttc    480
aaggaggacg gcaacatcct ggggcacaag ctggagtaca actacaacag ccacaacgtc    540
tatatcatgg ccgacaagca gaagaacggc atcaaggtga acttcaagat ccgccacaac    600
atcgaggacg gcagcgtgca gctcgccgac cactaccagc agaacacccc catcggcgac    660
ggccccgtgc tgctgcccga caaccactac ctgagcaccc agtccgccct gagcaaagac    720
cccaacgaga gcgcgatca catggtcctg ctggagttcg tgaccgccgc cgggatcact    780
ctcggcatgg acgagctgta caagagatct catatgcatc tcgagtgata gtctagacct    840
tctgcggggc ttgccttctg gccatgccct tcttctctcc cttgcacctg tacctcttgg    900
tctttgaata aagcctgagt aggaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaaa   1020
aaaaaaaaaa aaaaaaaaaa aaa                                           1043
```

<210> SEQ ID NO 37
<211> LENGTH: 1016
<212> TYPE: DNA
<213> ORGANISM: Artificial Sequence
<220> FEATURE:
<223> OTHER INFORMATION: Synthetic DNA template

<400> SEQUENCE: 37

```
gctaatacga ctcactatag gttccttaat cgcggatcca tacatacttc tttacattcc      60
aagatcacac cggtcgccac catgggatcc agcgagctga ttaaggagaa catgcacatg     120
aagctgtaca tggagggcac cgtggacaac catcacttca agtgcacatc cgagggcgaa     180
ggcaagccct acgagggcac ccagaccatg agaatcaagg tggtcgaggg cggccctctc     240
cccttcgcct tcgacatcct ggctactagc ttcctctacg gcagcaagac cttcatcaac     300
cacacccagg gcatccccga cttcttcaag cagtccttcc ctgagggctt cacatgggag     360
agagtcacca catacgaaga cggggggcgtg ctgaccgcta cccaggacac cagcctccag    420
gacggctgcc tcatctacaa cgtcaagatc agagggtga acttcacatc caacggccct     480
gtgatgcaga agaaaacact cggctgggag gccttcaccg agacgctgta ccccgctgac     540
ggcggcctgg aaggcagaaa cgacatggcc ctgaagctcg tgggcgggag ccatctgatc     600
gcaaacatca agaccacata tagatccaag aaacccgcta agaacctcaa gatgcctggc     660
gtctactatg tggactacag actggaaaga atcaaggagg ccaacaacga gacctacgtc     720
gagcagcacg aggtggcagt ggccagatac tgcgacctcc ctagcaaact ggggcacaga     780
tctcatatgc atctcgagtg atagtctaga ccttctgcgg ggcttgcctt ctggccatgc     840
ccttcttctc tcccttgcac ctgtacctct tggtctttga ataaagcctg agtaggaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaa        1016
```

<210> SEQ ID NO 38
<211> LENGTH: 1016
<212> TYPE: DNA
<213> ORGANISM: Artificial Sequence
<220> FEATURE:
<223> OTHER INFORMATION: Synthetic DNA template

<400> SEQUENCE: 38

```
gctaatacga ctcactatag gttccttaat cgcggatccc agctggttga aggggaccaa      60
aagatcacac cggtcgccac catgggatcc agcgagctga ttaaggagaa catgcacatg     120
aagctgtaca tggagggcac cgtggacaac catcacttca agtgcacatc cgagggcgaa     180
ggcaagccct acgagggcac ccagaccatg agaatcaagg tggtcgaggg cggccctctc     240
cccttcgcct tcgacatcct ggctactagc ttcctctacg gcagcaagac cttcatcaac     300
cacacccagg gcatccccga cttcttcaag cagtccttcc ctgagggctt cacatgggag     360
agagtcacca catacgaaga cggggggcgtg ctgaccgcta cccaggacac cagcctccag    420
gacggctgcc tcatctacaa cgtcaagatc agagggtga acttcacatc caacggccct     480
gtgatgcaga agaaaacact cggctgggag gccttcaccg agacgctgta ccccgctgac     540
ggcggcctgg aaggcagaaa cgacatggcc ctgaagctcg tgggcgggag ccatctgatc     600
gcaaacatca agaccacata tagatccaag aaacccgcta agaacctcaa gatgcctggc     660
gtctactatg tggactacag actggaaaga atcaaggagg ccaacaacga gacctacgtc     720
gagcagcacg aggtggcagt ggccagatac tgcgacctcc ctagcaaact ggggcacaga     780
tctcatatgc atctcgagtg atagtctaga ccttctgcgg ggcttgcctt ctggccatgc     840
ccttcttctc tcccttgcac ctgtacctct tggtctttga ataaagcctg agtaggaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaa        1016
```

```
<210> SEQ ID NO 39
<211> LENGTH: 1016
<212> TYPE: DNA
<213> ORGANISM: Artificial Sequence
<220> FEATURE:
<223> OTHER INFORMATION: Synthetic DNA template

<400> SEQUENCE: 39
gctaatacga ctcactatag gttccttaat cgcggatccc cacacacttc cttacattcc      60
aagatcacac cggtcgccac catgggatcc agcgagctga ttaaggagaa catgcacatg     120
aagctgtaca tggagggcac cgtggacaac catcacttca agtgcacatc cgagggcgaa     180
ggcaagccct acgagggcac ccagaccatg agaatcaagg tggtcgaggg cggccctctc     240
cccttcgcct tcgacatcct ggctactagc ttcctctacg gcagcaagac cttcatcaac     300
cacacccagg gcatccccga cttcttcaag cagtccttcc ctgagggctt cacatgggag     360
agagtcacca catacgaaga cggggggcgtg ctgaccgcta cccaggacac cagcctccag     420
gacggctgcc tcatctacaa cgtcaagatc agaggggtga acttcacatc caacggccct     480
gtgatgcaga agaaaacact cggctgggag gccttcaccg agacgctgta ccccgctgac     540
ggcggcctgg aaggcagaaa cgacatggcc ctgaagctcg tgggcgggag ccatctgatc     600
gcaaacatca agaccacata tagatccaag aaacccgcta agaacctcaa gatgcctggc     660
gtctactatg tggactacag actggaaaga atcaaggagg ccaacaacga gacctacgtc     720
gagcagcacg aggtggcagt ggccagatac tgcgacctcc ctagcaaact ggggcacaga     780
tctcatatgc atctcgagtg atagtctaga ccttctgcgg ggcttgcctt ctggccatgc     840
ccttcttctc tcccttgcac ctgtacctct tggtctttga ataaagcctg agtaggaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaa       1016

<210> SEQ ID NO 40
<211> LENGTH: 1016
<212> TYPE: DNA
<213> ORGANISM: Artificial Sequence
<220> FEATURE:
<223> OTHER INFORMATION: Synthetic DNA template

<400> SEQUENCE: 40
gctaatacga ctcactatag gttccttaat cgcggatccg ctgccgtata tgtgatgtca      60
cagatcacac cggtcgccac catgggatcc agcgagctga ttaaggagaa catgcacatg     120
aagctgtaca tggagggcac cgtggacaac catcacttca agtgcacatc cgagggcgaa     180
ggcaagccct acgagggcac ccagaccatg agaatcaagg tggtcgaggg cggccctctc     240
cccttcgcct tcgacatcct ggctactagc ttcctctacg gcagcaagac cttcatcaac     300
cacacccagg gcatccccga cttcttcaag cagtccttcc ctgagggctt cacatgggag     360
agagtcacca catacgaaga cggggggcgtg ctgaccgcta cccaggacac cagcctccag     420
gacggctgcc tcatctacaa cgtcaagatc agaggggtga acttcacatc caacggccct     480
gtgatgcaga agaaaacact cggctgggag gccttcaccg agacgctgta ccccgctgac     540
ggcggcctgg aaggcagaaa cgacatggcc ctgaagctcg tgggcgggag ccatctgatc     600
gcaaacatca agaccacata tagatccaag aaacccgcta agaacctcaa gatgcctggc     660
gtctactatg tggactacag actggaaaga atcaaggagg ccaacaacga gacctacgtc     720
gagcagcacg aggtggcagt ggccagatac tgcgacctcc ctagcaaact ggggcacaga     780
```

| | |
|---|---|
| tctcatatgc atctcgagtg atagtctaga ccttctgcgg ggcttgcctt ctggccatgc | 840 |
| ccttcttctc tcccttgcac ctgtacctct tggtctttga ataaagcctg agtaggaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaa | 1016 |

```
<210> SEQ ID NO 41
<211> LENGTH: 1016
<212> TYPE: DNA
<213> ORGANISM: Artificial Sequence
<220> FEATURE:
<223> OTHER INFORMATION: Synthetic DNA template

<400> SEQUENCE: 41
```

| | |
|---|---|
| gctaatacga ctcactatag gttccttaat cgcggatccc ccagctagat tgtaagctcc | 60 |
| ttagatccac cggtcgccac catgggatcc agcgagctga ttaaggagaa catgcacatg | 120 |
| aagctgtaca tggagggcac cgtggacaac catcacttca gtgcacatc cgagggcgaa | 180 |
| ggcaagccct acgagggcac ccagaccatg agaatcaagg tggtcgaggg cggccctctc | 240 |
| cccttcgcct tcgacatcct ggctactagc ttcctctacg gcagcaagac cttcatcaac | 300 |
| cacacccagg gcatccccga cttcttcaag cagtccttcc ctgagggctt cacatgggag | 360 |
| agagtcacca catacgaaga cggggggcgtg ctgaccgcta cccaggacac cagcctccag | 420 |
| gacggctgcc tcatctacaa cgtcaagatc agaggggtga acttcacatc caacggccct | 480 |
| gtgatgcaga agaaaacact cggctgggag gccttcaccg agacgctgta ccccgctgac | 540 |
| ggcggcctgg aaggcagaaa cgacatggcc ctgaagctcg tgggcgggag ccatctgatc | 600 |
| gcaaacatca agaccacata tagatccaag aaacccgcta agaacctcaa gatgcctggc | 660 |
| gtctactatg tggactacag actggaaaga atcaaggagg ccaacaacga gacctacgtc | 720 |
| gagcagcacg aggtggcagt ggccagatac tgcgacctcc ctagcaaact ggggcacaga | 780 |
| tctcatatgc atctcgagtg atagtctaga ccttctgcgg ggcttgcctt ctggccatgc | 840 |
| ccttcttctc tcccttgcac ctgtacctct tggtctttga ataaagcctg agtaggaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaa | 1016 |

```
<210> SEQ ID NO 42
<211> LENGTH: 1019
<212> TYPE: RNA
<213> ORGANISM: Artificial Sequence
<220> FEATURE:
<223> OTHER INFORMATION: Synthetic transfection control

<400> SEQUENCE: 42
```

| | |
|---|---|
| gggcgaauua agagagaaaa gaagaguaag aagaaauaua agacaccggu cgccaccaug | 60 |
| ggauccguga gcaagggcga ggagcuguuc accgggguggg ugcccauccu ggucgagcug | 120 |
| gacggcgacg uaaacggcca caaguucagc gugucggcg agggcgaggg cgaugccacc | 180 |
| uacggcaagc ugacccugaa guucaucugc accaccggca agcugcccgu gcccuggccc | 240 |
| acccucguga ccacccugac cuacggcgug cagugcuuca gccgcuaccc cgaccacaug | 300 |
| aagcagcacg acuucuucaa guccgccaug cccgaaggcu acguccagga gcgcaccauc | 360 |
| uucuucaagg acgacggcaa cuacaagacc cgcgccgagg ugaaguucga gggcgacacc | 420 |
| cugguggaacc gcaucgagcu gaagggcauc gacuucaagg aggacggcaa cauccugggg | 480 |
| cacaagcugg aguacaacua caacagccac aacgucuaua ucauggccga caagcagaag | 540 |

```
aacggcauca aggugaacuu caagauccgc acaacaucg aggacggcag cgugcagcuc    600
gccgaccacu accagcagaa cacccccauc ggcgacggcc ccgugcugcu gcccgacaac    660
cacuaccuga gcacccaguc cgcccugagc aaagacccca cgagaagcg cgaucacaug     720 guccugcugg aguucgugac cgccgccggg aucacucucg gcauggacga gcuguacaag    780
agaucucaua ugcaucucga gugauagucu agaccuucug cggggcuugc cuucuggcca    840
ugcccuucuu cucccccuug caccuguacc ucuuggucuu ugaauaaagc cugaguagga    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa aaaaaaaaaa aaaaaaaaaa aaaaaaaaa    1019

<210> SEQ ID NO 43
<211> LENGTH: 991
<212> TYPE: RNA
<213> ORGANISM: Artificial Sequence
<220> FEATURE:
<223> OTHER INFORMATION: Synthetic transfection control

<400> SEQUENCE: 43
gggcgaauua agagagaaaa gaagaguaag aagaaauaua agacaccggu cgccaccaug     60
ggauccagcg agcgauuaag gagaacaugc acaugaagcu guacauggag ggcaccgugg    120
acaaccauca cuucaagugc acauccgagg gcgaaggcaa gcccuacgag ggcacccaga    180
ccaugagaau caaggugguc gagggcggcc cucuccccuu cgccuucgac auccuggcua    240
cuagcuuccu cuacggcagc aagaccuuca ucaaccacac ccagggcauc cccgacuucu    300
ucaagcaguc cuucccugag ggcuucacau gggagagagu caccacauac gaagacgggg    360
gcgugcugac cgcuacccag gacaccagcc uccaggacgg cugccucauc uacaacguca    420
agaucagagg ggugaacuuc acauccaacg gcccugugau gcagaagaaa acacucggcu    480
gggaggccuu caccgagacg cuguaccccg cugacggcgg ccuggaaggc agaaacgaca    540
uggcccugaa gcucgugggc gggagccauc ugaucgcaaa caucaagacc acauauagau    600
ccaagaaacc cgcuaagaac cucaagaugc cuggcgucua cuauguggac uacagacugg    660
aaagaaucaa ggaggccaac aacgagaccu acgucgagca gcacgaggug gcaguggcca    720
gauacugcga ccucccuagc aaacuggggc acagaucuca uaugcaucuc gagugauagu    780
cuagaccuuc ugcggggcuu gccuucggc caugcccuuc uucucucccu ugcaccugua    840
ccucuugguc uuugaauaaa gccugaguag gaaaaaaaaa aaaaaaaaaa aaaaaaaaaa    900
aaaaaaaaaa aaaaaaaaaa aaaaaaaaaa aaaaaaaaaa aaaaaaaaaa aaaaaaaaaa    960
aaaaaaaaaa aaaaaaaaaa aaaaaaaaaa a                                   991

<210> SEQ ID NO 44
<211> LENGTH: 1013
<212> TYPE: RNA
<213> ORGANISM: Artificial Sequence
<220> FEATURE:
<223> OTHER INFORMATION: Synthetic transfection control

<400> SEQUENCE: 44
gggcgaauua agagagaaaa gaagaguaag aagaaauaua agacaccggu cgccaccaug     60
ggauccgugu cuaagggcga agagcugauu aaggagaaca ugcacaugaa gcuguacaug    120
gagggcaccg ugaacaacca ccacuucaag ugcacauccg agggcgaagg caagcccuac    180
gagggcaccc agaccaugag aaucaaggug gucgagggcg gccucucccc cuucgccuuc    240
```

| | |
|---|---:|
| gacauccugg cuaccagcuu cauguacggc agcagaaccu caucaaccea cacccagggc | 300 |
| auccccgacu ucuuuaagca guccuucccu gagggcuuca caugggagag agucaccaca | 360 |
| uacgaagacg ggggcgugcu gaccgcuacc caggacacca gccuccagga cggcugccuc | 420 |
| aucuacaacg ucaagaucag aggggugaac uucccaucca acggcccugu gaugcagaag | 480 |
| aaaacacucg gcugggaggc caacaccgag augcuguacc ccgcugacgg cggccuggaa | 540 |
| ggcagaagcg acauggcccu gaagcucgug gcgggggcc accugaucug caacuucaag | 600 |
| accacauaca gauccaagaa acccgcuaag aaccucaaga ugcccggcgu cuacuaugug | 660 |
| gaccacagac uggaaagaau caaggaggcc gacaaagaga ccuacgucga gcagcacgag | 720 |
| guggcugugg ccagauacug cgaccucccu agcaaacugg ggcacaaacu uaauagaucu | 780 |
| cauaugcauc ucgagugaua gucuagaccu cugcggggc uugccuucug gccaugcccu | 840 |
| ucuucucucc cuugcaccug uaccucuugg ucuuugaaua aagccugagu aggaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaa | 1013 |

<210> SEQ ID NO 45
<211> LENGTH: 1024
<212> TYPE: RNA
<213> ORGANISM: Artificial Sequence
<220> FEATURE:
<223> OTHER INFORMATION: Synthetic switch

<400> SEQUENCE: 45

| | |
|---|---:|
| gguuccuuaa ucgcggaucc ccacacacuu ccuuacauuc caagaucaca ccggucgcca | 60 |
| ccaugggauc cgugagcaag ggcgaggagc uguuccaccgg ggugugccc auccuggucg | 120 |
| agcuggacgg cgacguaaac ggccacaagu ucagcgucc ggcgagggc gagggcgaug | 180 |
| ccaccuacgg caagcugacc cugaaguuca ucugcaccac cggcaagcug cccgugcccu | 240 |
| ggcccacccu cgugaccacc cugaccuacg gcgugcagug cuucagccgc uaccccgacc | 300 |
| acaugaagca gcacgacuuc uucaaguccg ccaugcccga aggcuacguc caggagcgca | 360 |
| ccaucuucuu caaggacgac ggcaacuaca gacccgcgc cgaggugaag uucgagggcg | 420 |
| acacccuggu gaaccgcauc gagcugaagg gcaucgacuu caaggaggac ggcaacaucc | 480 |
| uggggcacaa gcuggaguac aacuacaaca gccacaacgu cuauaucaug gccgacaagc | 540 |
| agaagaacgg caucaaggug aacuucaaga uccgccacaa caucgaggac ggcagcgugc | 600 |
| agcucgccga ccacuaccag cagaacaccc ccaucggcga cggccccgug cugcugcccg | 660 |
| acaaccacua ccugagcacc caguccgccc ugagcaaaga ccccaacgag aagcgcgauc | 720 |
| acauggucu gcuggaguuc gugaccgccg ccgggaucac ucucggcaug gacgagcugu | 780 |
| acaagagauc ucauaugcau cucgagugau agucuagacc uucugcgggg cuugccuucu | 840 |
| ggccaugccc uucuucucuc ccuugcaccu guaccucuug gucuuugaau aaagccugag | 900 |
| uaggaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaaaaa | 1020 |
| aaaa | 1024 |

<210> SEQ ID NO 46
<211> LENGTH: 997
<212> TYPE: RNA
<213> ORGANISM: Artificial Sequence
<220> FEATURE:
<223> OTHER INFORMATION: Synthetic switch

<400> SEQUENCE: 46

```
gguuccuuaa ucgcggaucc auacauacuu cuuuacauuc caagaucaca ccggucgcca    60
ccaugggauc cagcgagcug auuaaggaga acaugcacau gaagcuguac auggagggca   120
ccguggacaa ccaucacuuc aagugcacau ccgagggcga aggcaagccc uacgagggca   180
cccagaccau gagaaucaag guggucgagg gcggcccucu ccccuucgcc uucgacaucc   240
uggcuacuag cuuccucuac ggcagcaaga ccuucaucaa ccacacccag ggcauccccg   300
acuucuucaa gcagguccuuc ccugagggcu ucacauggga gagagucacc acaucgaag   360
acggggggcgu gcugaccgcu acccaggaca ccagccucca ggacggcugc cucaucuaca   420
acgucaagau cagagggggug aacuucacau ccaacggccc ugugaugcag aagaaaacac   480
ucggcuggga ggccuucacc gagacgcugu accccgcuga cggcggccug gaaggcagaa   540
acgacauggc ccugaagcuc gugggcggga gccaucugau cgcaaacauc aagaccacau   600
auagauccaa gaaacccgcu aagaaccuca agaugccugg cgucuacuau guggacuaca   660
gacuggaaag aaucaaggag ccaacaacg agaccuacgu cgagcagcac gagguggcag   720
uggccagaua cugcgaccuc ccuagcaaac uggggcacag aucucauaug caucucgagu   780
gauagucuag accuucugcg gggcuugccu ucuggccaug cccuucuucu cucccuugca   840
ccuguaccuc uuggucuuug aauaaagccu gaguaggaaa aaaaaaaaaa aaaaaaaaaa   900
aaaaaaaaaa aaaaaaaaaa aaaaaaaaaa aaaaaaaaaa aaaaaaaaaa aaaaaaaaaa   960
aaaaaaaaaa aaaaaaaaaa aaaaaaaaaa aaaaaaa                            997
```

<210> SEQ ID NO 47
<211> LENGTH: 997
<212> TYPE: RNA
<213> ORGANISM: Artificial Sequence
<220> FEATURE:
<223> OTHER INFORMATION: Synthetic switch

<400> SEQUENCE: 47

```
gguuccuuaa ucgcggaucc cagcugguug aaggggacca aaagaucaca ccggucgcca    60
ccaugggauc cagcgagcug auuaaggaga acaugcacau gaagcuguac auggagggca   120
ccguggacaa ccaucacuuc aagugcacau ccgagggcga aggcaagccc uacgagggca   180
cccagaccau gagaaucaag guggucgagg gcggcccucu ccccuucgcc uucgacaucc   240
uggcuacuag cuuccucuac ggcagcaaga ccuucaucaa ccacacccag ggcauccccg   300
acuucuucaa gcagguccuuc ccugagggcu ucacauggga gagagucacc acaucgaag   360
acggggggcgu gcugaccgcu acccaggaca ccagccucca ggacggcugc cucaucuaca   420
acgucaagau cagagggggug aacuucacau ccaacggccc ugugaugcag aagaaaacac   480
ucggcuggga ggccuucacc gagacgcugu accccgcuga cggcggccug gaaggcagaa   540
acgacauggc ccugaagcuc gugggcggga gccaucugau cgcaaacauc aagaccacau   600
auagauccaa gaaacccgcu aagaaccuca agaugccugg cgucuacuau guggacuaca   660
gacuggaaag aaucaaggag ccaacaacg agaccuacgu cgagcagcac gagguggcag   720
uggccagaua cugcgaccuc ccuagcaaac uggggcacag aucucauaug caucucgagu   780
gauagucuag accuucugcg gggcuugccu ucuggccaug cccuucuucu cucccuugca   840
ccuguaccuc uuggucuuug aauaaagccu gaguaggaaa aaaaaaaaaa aaaaaaaaaa   900
aaaaaaaaaa aaaaaaaaaa aaaaaaaaaa aaaaaaaaaa aaaaaaaaaa aaaaaaaaaa   960
```

```
aaaaaaaaaa aaaaaaaaa aaaaaaaaaa aaaaaaa                          997
```

<210> SEQ ID NO 48
<211> LENGTH: 997
<212> TYPE: RNA
<213> ORGANISM: Artificial Sequence
<220> FEATURE:
<223> OTHER INFORMATION: Synthetic switch

<400> SEQUENCE: 48

```
gguuccuuaa ucgcggaucc ccacacacuu ccuuacauuc caagaucaca ccggucgcca    60
ccaugggauc cagcgagcug auuaaggaga acaugcacau gaagcuguac auggagggca   120
ccguggacaa ccaucacuuc aagugcacau ccgagggcga aggcaagccc uacgagggca   180
cccagaccau gagaaucaag guggucgagg gcggcccucu cccuucgcc uucgacaucc    240
uggcuacuag cuuccucuac ggcagcaaga ccuucaucaa ccacacccag ggcauccccg   300
acuucuucaa gcaguccuuc ccugagggcu ucacauggga gagagucacc acaucgaag    360
acggggggcgu gcugaccgcu acccaggaca ccagccucca ggacggcugc cucaucuaca   420
acgucaagau cagaggggug aacuucacau ccaacggccc ugugaugcag aagaaaacac   480
ucggcuggga ggccuucacc gagacgcugu accccgcuga cggcggccug gaaggcagaa   540
acgacauggc ccugaagcuc gugggcggga gccaucugau cgcaaacauc aagaccacau   600
auagauccaa gaaacccgcu aagaaccuca agaugccugg cgucuacuau gggacuaca    660
gacuggaaag aaucaaggag gccaacaacg agaccuacgu cgagcagcac gagguggcag   720
uggccagaua cugcgaccuc ccuagcaaac uggggcacag aucucauaug caucucgagu   780
gauagucuag accuucugcg gggcuugccu ucuggccaug cccuucuucu cucccuugca   840
ccuguaccuc uuggucuuug aauaaagccu gaguaggaaa aaaaaaaaa aaaaaaaaa    900
aaaaaaaaaa aaaaaaaaaa aaaaaaaaa aaaaaaaaaa aaaaaaaaa aaaaaaaaaa     960
aaaaaaaaaa aaaaaaaaa aaaaaaaaa aaaaaaa                            997
```

<210> SEQ ID NO 49
<211> LENGTH: 997
<212> TYPE: RNA
<213> ORGANISM: Artificial Sequence
<220> FEATURE:
<223> OTHER INFORMATION: Synthetic switch

<400> SEQUENCE: 49

```
gguuccgcga ucgcggaucc gcugccguau augugaugc acagaucaca ccggucgcca     60
ccaugggauc cagcgagcug auuaaggaga acaugcacau gaagcuguac auggagggca   120
ccguggacaa ccaucacuuc aagugcacau ccgagggcga aggcaagccc uacgagggca   180
cccagaccau gagaaucaag guggucgagg gcggcccucu ccccuucgcc uucgacaucc   240
uggcuacuag cuuccucuac ggcagcaaga ccuucaucaa ccacacccag ggcauccccg   300
acuucuucaa gcaguccuuc ccugagggcu ucacauggga gagagucacc acaucgaag    360
acggggggcgu gcugaccgcu acccaggaca ccagccucca ggacggcugc cucaucuaca   420
acgucaagau cagaggggug aacuucacau ccaacggccc ugugaugcag aagaaaacac   480
ucggcuggga ggccuucacc gagacgcugu accccgcuga cggcggccug gaaggcagaa   540
acgacauggc ccugaagcuc gugggcggga gccaucugau cgcaaacauc aagaccacau   600
auagauccaa gaaacccgcu aagaaccuca agaugccugg cgucuacuau gggacuaca    660
gacuggaaag aaucaaggag gccaacaacg agaccuacgu cgagcagcac gagguggcag   720
```

-continued

```
uggccagaua cugcgaccuc ccuagcaaac uggggcacag aucucauaug caucucgagu    780
gauagucuag accuucugcg gggcuugccu ucuggccaug cccuucuucu cucccuugca    840
ccuguaccuc uuggucuuug aauaaagccu gaguaggaaa aaaaaaaaaa aaaaaaaaa     900 aaaaaaaaaa aaaaaaaaaa aaaaaaaaaa aaaaaaaaaa aaaaaaaaaa aaaaaaaaaa   960
aaaaaaaaaa aaaaaaaaaa aaaaaaaaaa aaaaaa                             997
```

<210> SEQ ID NO 50
<211> LENGTH: 997
<212> TYPE: RNA
<213> ORGANISM: Artificial Sequence
<220> FEATURE:
<223> OTHER INFORMATION: Synthetic switch

<400> SEQUENCE: 50

```
gguuccuuaa ucgcggaucc cccagcuaga uuguaagcuc cuuagaucca ccggucgcca    60
ccaugggauc cagcgagcug auuaaggaga acaugcacau gaagcuguac auggagggca   120
ccguggacaa ccaucacuuc aagugcacau ccgagggcga aggcaagccc uacgagggca   180
cccagaccau gagaaucaag guggucgagg gcggcccucu ccccuucgcc uucgacaucc   240
uggcuacuag cuuccucuac ggcagcaaga ccuucaucaa ccacacccag ggcaucccg    300 acuucuucaa gcaguccuuc ccugagggcu ucacauggga gagagucacc acauacgaag   360 acggggggcgu gcugaccgcu acccaggaca ccagccucca ggacggcugc cucaucuaca   420
acgucaagau cagaggggug aacuucacau ccaacggccc ugugaugcag aagaaaacac   480
ucggcuggga ggccuucacc gagacgcugu accccgcuga cggcggccug gaaggcagaa   540
acgacauggc ccugaagcuc gugggcggga gccaucugau cgcaaacauc aagaccacau   600
auagauccaa gaaacccgcu aagaaccuca agaugccugg cgucuacuau guggacuaca   660
gacuggaaag aaucaaggag gccaacaacg agaccuacgu cgagcagcac gagguggcag   720
uggccagaua cugcgaccuc ccuagcaaac uggggcacag aucucauaug caucucgagu   780
gauagucuag accuucugcg gggcuugccu ucuggccaug cccuucuucu cucccuugca   840
ccuguaccuc uuggucuuug aauaaagccu gaguaggaaa aaaaaaaaaa aaaaaaaaa    900 aaaaaaaaaa aaaaaaaaaa aaaaaaaaaa aaaaaaaaaa aaaaaaaaaa aaaaaaaaaa   960
aaaaaaaaaa aaaaaaaaaa aaaaaaaaaa aaaaaa                             997
```

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51

```
tcacctcctc agagcaacct                                                20
```

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52

```
ggaactagaa gcccctggag                                                20
```

```
<210> SEQ ID NO 53
<211> LENGTH: 19
<212> TYPE: DNA
<213> ORGANISM: Artificial Sequence
<220> FEATURE:
<223> OTHER INFORMATION: primer

<400> SEQUENCE: 53
acgtgaggac gagcatgtg                                                  19

<210> SEQ ID NO 54
<211> LENGTH: 18
<212> TYPE: DNA
<213> ORGANISM: Artificial Sequence
<220> FEATURE:
<223> OTHER INFORMATION: primer

<400> SEQUENCE: 54
gtgcagcgtt gagtgtct                                                   18

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
tgggcgtgta aggtgtgtaa                                                 20

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
cgatgtactg gatggcactg                                                 20

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
gggattccct ttggaagtgt                                                 20

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
cggcaaagaa tcttggagac                                                 20

<210> SEQ ID NO 59
<211> LENGTH: 20
<212> TYPE: DNA
<213> ORGANISM: Artificial Sequence
<220> FEATURE:
<223> OTHER INFORMATION: primer
```

```
<400> SEQUENCE: 59
aggaaggagg cagaggaaag                                              20

<210> SEQ ID NO 60
<211> LENGTH: 20
<212> TYPE: DNA
<213> ORGANISM: Artificial Sequence
<220> FEATURE:
<223> OTHER INFORMATION: primer

<400> SEQUENCE: 60
cagctgttct gctgtgaagg                                              20

<210> SEQ ID NO 61
<211> LENGTH: 22
<212> TYPE: DNA
<213> ORGANISM: Artificial Sequence
<220> FEATURE:
<223> OTHER INFORMATION: primer

<400> SEQUENCE: 61
caccattggc aatgagcggt tc                                           22

<210> SEQ ID NO 62
<211> LENGTH: 22
<212> TYPE: DNA
<213> ORGANISM: Artificial Sequence
<220> FEATURE:
<223> OTHER INFORMATION: primer

<400> SEQUENCE: 62
aggtctttgc ggatgtccac gt                                           22
```

METHOD FOR SELECTING SKELETAL MUSCLE PROGENITOR CELL

CROSS-REFERENCE TO RELATED APPLICATIONS

This patent application is the U.S. national phase of International Patent Application No. PCT/JP2016/050997, filed on Jan. 14, 2016, which claims the benefit of Japanese Patent Application No. 2015-005447, filed Jan. 14, 2015, the disclosures of which are incorporated herein by reference in their entireties for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 38,278 bytes ASCII (Text) file named "730326SequenceListing.txt," created Jul. 13, 2017.

TECHNICAL FIELD

The present invention relates to a technique for identifying and selecting a skeletal muscle progenitor cell.

BACKGROUND ART

For drug discovery screening and cell transplantation therapy, expectations are directed toward tissue cells derived from pluripotent stem cells, and many induction methods of the tissue cells have currently been developed. However, it is difficult to uniformly induce differentiation of all cells of pluripotent stem cells into desired cells. To appropriately utilize induced cells, therefore, a technique for purifying a desired cell becomes important.

As a method of such purification, a purification method using an antibody and a cellular surface antigen as an index has been proposed. However, not all desired cells recognize cellular surface antigens appropriate for the cells. In particular, human skeletal muscle progenitor cell does not have such cellular surface antigen, which poses a large problem for cell transplantation therapy (non-patent document 1).

DOCUMENT LIST

Non-Patent Document

[non-patent document 1] Mizuno Y, et al. FASEB J. 24:2245-2253, 2010

SUMMARY OF THE INVENTION

Problems to be Solved by the Invention

An object of the present invention is to provide a method of selecting a skeletal muscle progenitor cell from a cell population containing skeletal muscle progenitor cells and other cell types, which is induced from pluripotent stem cells, and a method of producing a uniform skeletal muscle progenitor cell population from pluripotent stem cells, which contains said selection method. Also, an object of the present invention is to provide a skeletal muscle progenitor cell suitable for transplantation.

Means of Solving the Problems

The present inventors have conducted intensive studies in an attempt to solve the above-mentioned problems and, under the hypothesis that cells may be identified using miRNA specifically expressed in skeletal muscle progenitor cells as an indicator, prepared mRNA, whose expression of the marker protein is controlled by miRNA responsiveness, and introduced same into a cell population containing skeletal muscle progenitor cells. As a result, they have succeeded in efficient sorting of skeletal muscle progenitor cells based on differences in the expression of marker proteins, which resulted in the completion of the present invention.

Therefore, the present invention provides the following.

[1] A method of sorting a skeletal muscle progenitor cell, comprising a step of introducing miRNA-responsive mRNA into a cell population, wherein the miRNA-responsive mRNA consists of a sequence comprising the following:
 (i) a nucleic acid having a sequence specifically recognized by miRNA specifically expressed in a skeletal muscle progenitor cell, and
 (ii) a nucleic acid comprising a sequence encoding a marker protein, and
 (ii) is functionally linked to the nucleic acid of (i).

[2] The method of [1], wherein the aforementioned (i) and (ii) are linked in the direction of from 5' to 3'.

[3] The method of [1] or [2], wherein the miRNA specifically expressed in a skeletal muscle progenitor cell of the aforementioned (i) is one or more miRNAs selected from the group consisting of miR-1, miR-133 and miR-206.

[4] The method of any of [1] to [3], wherein the marker protein of the aforementioned (ii) is one or more genes selected from the group consisting of a fluorescent protein, an apoptosis induction protein and a protein encoded by a suicide gene.

[5] The method of [4], wherein the marker protein of the aforementioned (ii) is a fluorescent protein, and the method comprises a step of further introducing the control mRNA into the cell population.

[6] The method of any of [1] to [5], wherein the aforementioned cell population is a population of cells obtained by differentiation induction of pluripotent stem cells into skeletal muscle progenitor cells.

[7] The method of [6], wherein the aforementioned differentiation induction of pluripotent stem cells into skeletal muscle progenitor cells comprises the following steps (1) to (5):
 (1) a step of culturing pluripotent stem cells in a culture medium containing a TGF-β inhibitor and a GSK3β inhibitor,
 (2) a step of culturing the cells obtained in the step of (1) in a culture medium containing a TGF-β inhibitor, a GSK3β inhibitor, IGF1, HGF and bFGF,
 (3) a step of culturing the cells obtained in the step of (2) in a culture medium containing a TGF-β inhibitor, a GSK3β inhibitor and IGF1,
 (4) a step of culturing the cells obtained in the step of (3) in a culture medium containing a TGF-β inhibitor, IGF1 and HGF, and
 (5) a step of culturing the cells obtained in the step of (4) in a culture medium containing a TGF-β inhibitor, IGF1 and serum.

[8] The method of [7], wherein the TGF-β inhibitor in the aforementioned steps (1) to (5) is SB431542, the GSK3β inhibitor in the aforementioned Step (1) is CHIR99021, and the GSK3β inhibitor in the aforementioned steps (2) and (3) is LiCl.

[9] The method of [7] or [8], wherein the serum in the aforementioned Step (5) is horse serum.

[10] A method of producing a skeletal muscle progenitor cell from a pluripotent stem cell, comprising the following steps (1) to (3):
(1) a step of producing a skeletal muscle progenitor cell from a pluripotent stem cell,
(2) a step of introducing miRNA-responsive mRNA comprising the following (i) and (ii) into the cells obtained in the step of (1):
  (i) a nucleic acid having a sequence specifically recognized by miRNA specifically expressed in a skeletal muscle progenitor cell,
  (ii) a nucleic acid encoding a marker protein, and
  (ii) is functionally linked to the nucleic acid of (i), and
(3) a step of selecting a cell having a small translation amount of the aforementioned marker protein or incapable of detection thereof.
[11] The method of [10], wherein the aforementioned Step (1) comprises the following steps (1-1) to (1-5):
(1-1) a step of culturing pluripotent stem cells in a culture medium containing a TGF-β inhibitor and a GSK3β inhibitor,
(1-2) a step of culturing the cells obtained in the step of (1-1) in a culture medium containing a TGF-β inhibitor, a GSK3β inhibitor, IGF1, HGF and bFGF,
(1-3) a step of culturing the cells obtained in the step of (1-2) in a culture medium containing a TGF-β inhibitor, a GSK3β inhibitor and IGF1,
(1-4) a step of culturing the cells obtained in the step of (1-3) in a culture medium containing a TGF-β inhibitor, IGF1 and HGF, and
(1-5) a step of culturing the cells obtained in the step of (1-4) in a culture medium containing a TGF-β inhibitor, IGF1 and serum.
[12] The method of [11], wherein the TGF-β inhibitor in the aforementioned steps (1-1) to (1-5) is SB431542, the GSK3β inhibitor in the aforementioned step (1-1) is CHIR99021, and the GSK3β inhibitor in the aforementioned steps (1-2) and (1-3) is LiCl.
[13] The method of [11] or [12], wherein the serum in the aforementioned step (1-5) is horse serum.
[14] The method of any of [10] to [13], wherein the aforementioned (i) and (ii) are linked in the direction of from 5' to 3'.
[15] The method of any of [10] to [14], wherein the miRNA specifically expressed in a skeletal muscle progenitor cell of the aforementioned (i) is one or more miRNAs selected from the group consisting of miR-1, miR-133 and miR-206.
[16] The method of any of [10] to [15], wherein the marker protein of the aforementioned (ii) is one or more genes selected from the group consisting of a fluorescent protein, an apoptosis induction protein and a protein encoded by a suicide gene.
[17] The method of [16], wherein the marker protein of the aforementioned (ii) is a fluorescent protein, the method comprises a step of further introducing the control mRNA into the cells obtained in the step of (1), and the aforementioned Step (3) is a step of selecting a cell further introduced with the control mRNA.

Effect of the Invention

The method of the present invention makes it possible to selectively obtain a skeletal muscle progenitor cell from a pluripotent stem cell.

BRIEF DESCRIPTION OF THE DRAWINGS

In FIG. 1.

In FIG. 2, FIGS. 2A and B show the results of quantification, by qRT-PCR, of the expression of miR-206 of PAX3-GFP iPSCs (A) and MYF5-tdTomato C3 iPSCs (B). In the Figure, D in the horizontal axis shows the number of days from the start of the differentiation induction. The vertical axis shows the expression quantitative ratio with the value of D2 as 1 in FIG. 2A, and the expression quantitative ratio with the value of D19 as 1 in FIG. 2B. The error bar shows standard deviation. FIG. 2C shows dot plot after transfection of miR-206 switch into the cells on day 44 (left figure) and day 78 (right figure) of differentiation induction of PAX3-GFP iPSCs. In the Figures, the vertical axis shows fluorescence intensity of tagBFP, and the horizontal axis shows fluorescence intensity of tagRFP. FIG. 2D shows dot plot after transfection of miR-206 switch into the cells on day 55 (left figure) and day 88 (right figure) of differentiation induction of MYF5-tdTomato C3 iPSCs. In the Figure, the vertical axis shows fluorescence intensity of tagBFP, and the horizontal axis shows fluorescence intensity of EGFP. FIG. 2E shows dot plot after transfection of miR-1 switch or miR-133 switch into the cells on day 78 of differentiation induction of PAX3-GFP iPSCs. In the Figure, the vertical axis shows fluorescence intensity of tagBFP, and the horizontal axis shows fluorescence intensity of tagRFP. FIG. 2F shows dot plot after transfection of miR-489 switch or miR-708 switch into the cells on day 88 of differentiation induction of MYF5-tdTomato C3 iPSCs. In the Figure, the vertical axis shows fluorescence intensity of tagBFP, and the horizontal axis shows fluorescence intensity of EGFP.

In FIG. 3, In FIG. 3C to FIG. 3H, the vertical axis shows an expression quantitative ratio with the expression level derived from miR-206− fraction as 1, and the error bar shows standard deviation.

In FIG. 4, In FIG. 4C to FIG. 4G, the vertical axis shows an expression quantitative ratio with the expression level of P 7 as 1, and the error bar shows standard deviation.

In FIG. 5.

In FIG. 6, In FIG. 6C to FIG. 6H, the vertical axis shows an expression quantitative ratio with the expression level of miR-206− fraction as 1, and the error bar shows standard deviation.

In FIG. 7.

DESCRIPTION OF EMBODIMENTS

Figure 1:
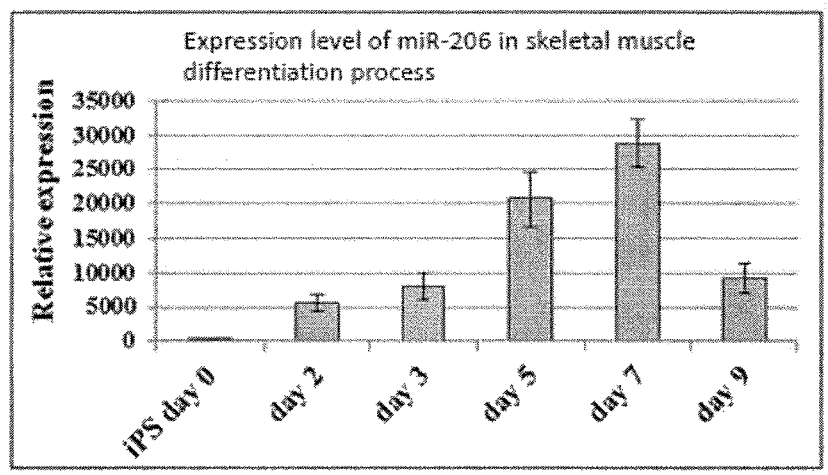
FIG. 1A shows the results of quantification, by the Quantitative RT-PCR method (qRT-PCR), of the expression of miR-206 in the skeletal muscle differentiation process by Dox-MyoD forced expression in human iPS cell line. Dox was added to the medium up to day 7, and was not added on day 8-day 9. The day contained in the sample name shows the number of days when differentiation induction was performed. The value on iPS day 0 is 1, and the error bar shows standard deviation.
FIG. 1B shows a schematic drawing of miRNA switch.
FIG. 1C shows the results of FACS analysis on Day 1 when Dox induction was not performed (Dox−)
FIG. 1D shows the results of FACS analysis on Day 6 when Dox induction was performed (Dox+). The vertical axes in FIG. 1C and FIG. 1D show fluorescence intensity of EGFP, and the horizontal axes show fluorescence intensity of tagBFP.
Figure 1:
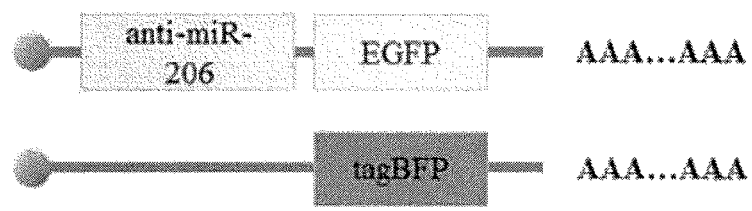
Figure 1:
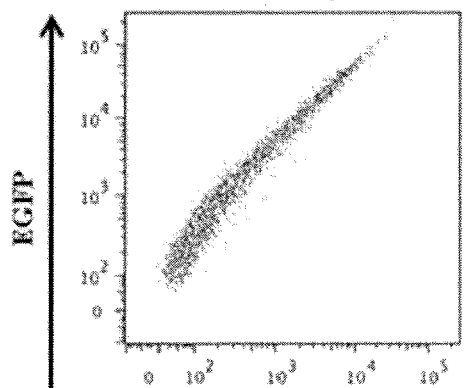

The present invention is explained in detail below by illustrating the embodiments. However, the present invention is not limited to the following embodiments.

The present invention provides a method of sorting skeletal muscle progenitor cells, which includes a step of introducing an miRNA-responsive mRNA into a cell population. In the introduction step in the method of this embodiment, the cell population into which the miRNA-responsive mRNA is introduced and which becomes the target of sorting may be any cell population capable of containing skeletal muscle progenitor cells. For example, it may be a cell population of skeletal muscle progenitor cells induced to differentiate from pluripotent stem cells, or a population of cells isolated from a living body, though the cell population is not limited thereto. Therefore, the miRNA-responsive mRNA may be introduced into a cell population unclear as to whether it contains a skeletal muscle progenitor cell. In a preferable embodiment, the cell population may be a cell population of skeletal muscle progenitor cells induced to differentiate from pluripotent stem cells. The cell population of skeletal muscle progenitor cells induced to differentiate from pluripotent stem cells is a cell population of skeletal muscle progenitor cells that underwent a step of differentiation induction of pluripotent stem cells into skeletal muscle progenitor cells by the method described in detail later, and may contain cells converted to skeletal muscle progenitor cells by a desired induction and cells differentiated into a cell type other than skeletal muscle progenitor cell.

In the present invention, the "skeletal muscle" means a mature muscle, and includes a muscle cell which is a muscle fiber or multinuclear cell. In the present invention, moreover, the "skeletal muscle progenitor cell" means a cell that has not reached a mature muscle cell but is in a preliminary stage, and has an ability to selectively differentiate into a muscle cell. Here, the skeletal muscle progenitor cell does not mean that it does not at all have a differentiation potency into other mesoderm cells such as osteoblast, adipocyte and the like and, in some cases, a cell having a differentiation potency into a cell other than muscle cell can also be encompassed in the skeletal muscle progenitor cell of the present invention. A skeletal muscle progenitor cell is characterized by the expression of a particular gene and can be identified by, for example, detection of the expression of at least one marker gene selected from MyoD, Myf5, Pax7, Myogenin, myosin heavy chain, NCAM, Desmin, SkMAct, MF20, M-Cadherin, Fgfr4 and VCAME1. The skeletal muscle progenitor cell in the present invention can preferably be a Myf5-positive cell, and more preferably a Myf5 and Pax7-positive cell. Unless particularly specified, the skeletal muscle progenitor cell in the present invention includes skeletal muscle stem cells and satellite cells.

<miRNA-Responsive mRNA>

In the present invention, the miRNA-responsive mRNA is an mRNA containing (i) a nucleic acid having a sequence specifically recognized by miRNA specifically expressed in a skeletal muscle progenitor cell (hereinafter to be referred to as miRNA target sequence), and (ii) a nucleic acid comprising a sequence encoding a marker protein, which mRNA is functionally linked such that the translation of the marker protein in (ii) is controlled by the nucleic acid sequence of (i).

In the present invention, being controlled by the nucleic acid sequence of (i) means that the translation amount of the marker protein is suppressed by inhibited translation of miRNA-responsive mRNA, decomposition thereof and the like, according to the abundance of miRNA specifically expressed in the skeletal muscle progenitor cells.

The "miRNA" in the present invention is a non-coding RNA with a short chain (20-25 bases) present in a cell, and is involved in the regulation of gene expression through inhibition of translation from mRNA into a protein and decomposition of mRNA. This miRNA is transcribed from DNA as a single-stranded pri-miRNA capable of taking a hairpin loop structure containing the miRNA and a complementary chain thereof, partly cleaved into pre-miRNA by an enzyme called Drosha in the nucleus, extranuclearly transported, and further cleaved by Dicer to be functional.

The aforementioned (i) "miRNA specifically expressed in a skeletal muscle progenitor cell" used in the present invention is not particularly limited as long as it is an miRNA expressed higher in skeletal muscle progenitor cells as compared to cells other than skeletal muscle progenitor cell. For example, it may be an miRNA expressed highly at a ratio of not less than 10%, not less than 20%, not less than 30%, not less than 40%, not less than 50%, not less than 60%, not less than 70%, not less than 80%, not less than 90% or above, in skeletal muscle progenitor cells as compared to cells other than skeletal muscle progenitor cell, but it is not limited thereto. Such miRNA can be appropriately selected from miRNAs registered in the database information (e.g., www.mirbase.org/ or www.microrna.org/) and/or miRNAs described in the document information described in the database. In the present invention, the "miRNA specifically expressed in a skeletal muscle progenitor cell" of the aforementioned (i) is preferably a short chain non-coding RNA generated from hsa-miR-1, hsa-miR-133 or hsa-miR-206 (also referred to as miR-1, miR-133 or miR-206, respectively), more preferable miR-1 is hsa-miR-1-3p (SEQ ID NO: 1), and more preferable miR-133 is hsa-miR-133a-3p (SEQ ID NO: 2). In the present invention, preferable miRNA specifically expressed in a skeletal muscle progenitor cell is hsa-miR-206 (SEQ ID NO: 3).

In the present invention, being "specifically recognized by miRNA specifically expressing in a skeletal muscle progenitor cell" of the aforementioned (i) refers to the presence of an miRNA in the form of an RNA-induced silencing complex (RISC) resulting from an interaction of the miRNA with predetermined multiple proteins.

In the present invention, the miRNA target sequence is preferably, for example, a sequence completely complementary to the miRNA. Alternatively, the target sequence of the miRNA may have an inconsistency (mismatch) with the completely complementary sequence as long as it is recognized by the miRNA. The mismatch with the sequence completely complementary to the miRNA may be any as long as it can be generally recognized by the miRNA in a desired cell and, as regards the inherent intracellular function in vivo, about 40-50% mismatch may be acceptable. While such mismatch is not particularly limited, examples thereof include mismatch(es) in 1 base, 2 bases, 3 bases, 4 bases, 5 bases, 6 bases, 7 bases, 8 bases, 9 bases or 10 bases, or 1%, 5%, 10%, 20%, 30% or 40% mismatch of the whole recognition sequence. Particularly, as in the miRNA target sequence on the mRNA provided in the cell, many mismatches may present particularly in a part other than the seed region, i.e., in a region on the 5' side in the target sequence, which corresponds to about 16 bases on the 3' side of miRNA, and the seed region may be free of mismatch or may contain mismatch(es) in 1 base, 2 bases or 3 bases. Such sequence only needs to be a base length including the number of bases to which RISC specifically binds, and the length is not particularly limited. Preferred is a sequence of not less than 18 bases and less than 24 base, more preferably a sequence of not less than 20 bases and less than 22 bases. In the present invention, the miRNA target sequence can be appropriately determined and used by introducing miRNA-responsive mRNA having the sequence into a skeletal muscle progenitor cell and a cell other than skeletal muscle progenitor cell, and confirming suppressed translation of the corresponding marker protein only in the skeletal muscle progenitor cell. In the present invention, examples of the target sequence of preferable miRNAs corresponding to the "miRNA specifically expressed in a skeletal muscle progenitor cell" are shown in Table 1.

TABLE 1

| miRNA specifically expressed in skeletal muscle progenitor cell | miRNA target sequence (5'→3') | SEQ ID NO: |
|---|---|---|
| hsa-miR-1-3p | AUACAUACUUCUUUACAUUCCA | 4 |
| hsa-miR-133a-3p | CAGCUGGUUGAAGGGGACCAAA | 5 |
| hsa-miR-206 | CCACACACUUCCUUACAUUCCA | 6 |

The "marker protein" used in the present invention is any protein translated in the cell to function as a marker and enable sorting of cells. One example of the protein translated in the cell to function as a marker includes, but is not limited to, fluorescent protein, luminescent protein, protein aiding fluorescence, luminescence or color development, membrane protein, apoptosis induction protein, suicide protein and the like.

In the present invention, examples of the fluorescent protein include, but are not limited to, blue fluorescent proteins such as Sirius, TagBFP, EBFP and the like; cyan fluorescent proteins such as mTurquoise, TagCFP, AmCyan, mTFP1, MidoriishiCyan, CFP and the like; green fluorescent proteins such as TurboGFP, AcGFP, TagGFP, Azami-Green (e.g., hmAG1), ZsGreen, EmGFP, EGFP, GFP2, HyPer and the like; yellow fluorescent proteins such as TagYFP, EYFP, Venus, YFP, PhiYFP, PhiYFP-m, TurboYFP, ZsYellow, mBanana and the like; orange fluorescent proteins such as KusabiraOrange (e.g., hmKO2), mOrange and the like; red fluorescent proteins such as TurboRFP, DsRed-Express, DsRed2, TagRFP, DsRed-Monomer, AsRed2, mStrawberry and the like; and near-infrared fluorescent proteins such as TurboFP602, mRFP1, JRed, KillerRed, mCherry, HcRed, KeimaRed (e.g., hdKeimaRed), mRasberry, mPlum and the like.

In the present invention, examples of the luminescent protein include, but are not limited to, aequorin. Examples of the protein aiding fluorescence, luminescence or color development include, but are not limited to, an enzyme that decomposes precursor substance of fluorescence, luminescence or color development, and includes such as luciferase, phosphatase, peroxidase, β-lactamase and the like. In the present invention, when a protein aiding fluorescence, luminescence or color development is used as a marker, skeletal muscle progenitor cells can be sorted by contacting a cell population with the corresponding precursor substance, or introducing the corresponding precursor substance into the cell population.

In the present invention, the apoptosis induction protein means a protein having an activity to induce apoptosis of cells. Examples thereof include, but are not limited to, IκB, Smac/DIABLO, ICE, HtrA2/OMI, AIF, endonuclease G, Bax, Bak, Noxa, Hrk (harakiri), Mtd, Bim, Bad, Bid, PUMA, activated caspase-3, Fas, Tk and the like.

In the present invention, the suicide protein means a protein whose expression in a cell is lethal to the cell. In the present invention, the suicide protein may be one that induces cell death by itself (e.g., diphtheria toxin A), or a protein that renders a cell sensitive to a particular drug (e.g., simple herpes thymidine kinase renders a cell sensitive to an antivirus compound). Examples the suicide protein include, but are not limited to, diphtheria toxin A, simple herpes thymidine kinase (HSV-TK), carboxypeptidase G2 (CPG2), carboxyl esterase (CA), cytosine deaminase (CD), cytochrome P450 (cyt-450), deoxycytidine kinase (dCK), nitroreductase (NR), purine nucleoside phosphorylase (PNP), thymidine phosphorylase (TP), varicella zoster virus thymidine kinase (VZV-TK), xanthine-guanine phosphoribosyltransferase (XGPRT) and the like.

In the present invention, the above-mentioned marker protein may be provided with a localization signal. Examples the localization signal include, but are not limited to, nuclear localization signal, cellular membrane localization signal, mitochondria localization signal, protein secretion signal and the like, specifically, classical nuclear localization sequence (NLS), M9 sequence, mitochondria target sequence (MTS), and endoplasmic reticulum transfer sequence. Such localization signal is particularly advantageous when the cells are sorted on images by the below-mentioned imaging cytometry and the like.

In the present invention, being functionally linked such that the translation of the marker protein in (ii) is controlled by the nucleic acid sequence of (i) means being provided with at least one miRNA target sequence in 5'UTR, 3'UTR and/or an open reading frame (containing initiation codon) encoding the marker protein. The miRNA-responsive mRNA preferably has cap structure (7-methylguanosine 5'-phosphoric acid), the open reading frame encoding the marker protein, and poly-A tail from the 5'-terminal in the direction of from 5' to 3', and is provided with at least one miRNA target sequence in 5'UTR, 3'UTR and/or open reading frame. The position of the miRNA target sequence in mRNA may be in 5'UTR or 3'UTR, or in the open reading frame (3'-side of the initiation codon), and all of these may be provided with the miRNA target sequence. Therefore, the number of the miRNA target sequence may be 1, 2, 3, 4, 5, 6, 7, 8 or more.

Preferably, in the miRNA-responsive mRNA, the nucleic acids of (i) and (ii) are linked in this order in the direction of 5' to 3'. Therefore, only one miRNA target sequence needs to be present in 5'UTR. This is because translation can be efficiently suppressed. In this case, the number of bases and the kind of bases between the cap structure and the miRNA target sequence may be any as long as they do not constitute a stem structure or a steric structure. For example, the number of bases between the cap structure and the miRNA target sequence can be designed to be 0-50 bases, preferably 10-30 bases. In addition, the number of bases and the kind of bases between the miRNA target sequence and the initiation codon may be any as long as they do not constitute a stem structure or a steric structure, and the number of bases between the miRNA target sequence and the initiation codon can be designed to be 0-50, preferably 10-30 bases.

In the present invention, the miRNA target sequence in the miRNA-responsive mRNA is preferably free of AUG to be the initiation codon. For example, when the miRNA target sequence is present in 5'UTR and AUG is contained in the target sequence, the target sequence is preferably designed to be in-frame in relation to the sequence encoding the marker protein linked to the 3' side. Alternatively, when AUG is contained in the target sequence, AUG in the target sequence can be converted to GUG and used. To minimize the influence of AUG in the target sequence, the configuration position of the target sequence in 5'UTR can be changed as appropriate. For example, the number of bases between the miRNA target sequence and the initiation codon can be designed to be 0-60 bases, for example, 0-15 bases, 10-20 bases, 20-30 bases, 30-40 bases, 40-50 bases, 50-60 bases.

In the present invention, to reduce cytotoxicity, mRNA preferably contains modified bases such as pseudouridine, 5-methylcytidine and the like instead of general uridine and cytidine. The site of the modified base can be the whole or partial for each independently uridine and cytidine and, when it is partial, a random site can be employed at any ratio.

In the present invention, when the miRNA target sequence is present in 5'UTR, for example, sequences described in the following Table 2 may be employed. Those other than the miRNA target sequence are not particularly limited.

TABLE 2

| miRNA specifically expressed in skeletal muscle progenitor cell | sequence of 5'UTR (5'→3') in miRNA-responsive mRNA (AUG at 3'-terminal is initiation codon) | SEQ ID NO: |
|---|---|---|
| hsa-miR-1-3p | GGUUCCUUAAUCGCGGAUCCAUACA UACUUCUUUACAUUCCAAGAUCACA CCGGUCGCCACCAUG | 7 |

TABLE 2-continued

| miRNA specifically expressed in skeletal muscle progenitor cell | sequence of 5'UTR (5'→3') in miRNA-responsive mRNA (AUG at 3'-terminal is initiation codon) | SEQ ID NO: |
|---|---|---|
| hsa-miR-133a-3p | GGUUCCUUAAUCGCGGAUCCCAGCU GGUUGAAGGGGACCAAAAGAUCACA CCGGUCGCCACCAUG | 8 |
| hsa-miR-206 | GGUUCCUUAAUCGCGGAUCCCCACA CACUUCCUUACAUUCCAAGAUCACA CCGGUCGCCACCAUG | 9 |

In the present invention, miRNA-responsive mRNA is necessary for translation of marker protein. While the downstream of the sequence encoding the marker protein (i.e., 3'UTR) is not particularly limited as long as it has poly-A sequence, when the miRNA target sequence is present in 5'UTR, for example, the sequences described in the following Table 3 may be adopted.

TABLE 3

| sequence of 3'UTR | SEQ ID NO: |
|---|---|
| UCUAGACCUUCUGCGGGGCUUGCCUUCUGGCCAUGCCC UUCUUCUCUCCCUUGCACCGUACCUCUUGGUCUUUGA AUAAAGCCUGAGUAGGAAAAAAAAAAAAAAAAAAAAA AAAAAAAAAAAAAAAAAAAAAAAAAAAAAAAAAAAA AAAAAAAAAAAAAAAAAAAAAAAAAAAAAAAAAAAA AAAAAAAAAAAAAAAAAAAA | 10 |

When the sequence of the miRNA-responsive mRNA is determined according to the above, those of ordinary skill in the art can synthesize same by any method known in genetic engineering. Particularly, it can be obtained by in vitro synthesis method using a template DNA containing a promoter sequence as a template.

Before carrying out the sorting method according to this embodiment, a screening step may be performed to examine the effectiveness of the sorting. Specifically, a plurality of candidate miRNA-responsive mRNAs having 5'UTR as exemplified above are produced, each of which is introduced into a skeletal muscle progenitor cell group having whose known purity, and target sequences of miRNAs and miRNA-responsive mRNAs that are highly effective in screening can be determined. Such step is also described in detail in the Examples.

<Method of Sorting Skeletal Muscle Progenitor Cells>

Sorting of the skeletal muscle progenitor cells of the present invention includes a step of introducing miRNA-responsive mRNA into a cell population, and a step of sorting cells in which the translation amount of the marker protein contained in the aforementioned miRNA-responsive mRNA is small or cannot be detected.

In some cases, miRNA-responsive mRNA to be introduced may be only one kind, or two or more kinds, for example, three, four, five, six, seven, or eight or more kinds thereof may be used. For example, two or more kinds of miRNA-responsive mRNAs are used, each miRNA-responsive mRNA is desirably different in both the miRNA target sequence and marker protein. When two or more kinds of miRNA-responsive mRNAs are used, the number of miRNA target sequences contained in the miRNA-responsive mRNA, the distance from the 5'-terminal of the miRNA target sequence, and other structural features of the miRNA-responsive mRNA may be the same or different between respective miRNA-responsive mRNAs. Alternatively, miRNA-responsive mRNA having the same miRNA target sequence but a different marker protein can also be used. For example, it is also possible to use a miRNA-responsive mRNA having a nucleic acid containing a sequence encoding an apoptosis-inducing protein which shows signal transduction through different pathway, such as Fas and Bim etc. are combined with the same miRNA target sequence. In this case, efficient removal of cells other than skeletal muscle precursor cells is expected.

In the present invention, as a step of introducing miRNA-responsive mRNA into a cell population, one or more kinds of miRNA-responsive mRNAs are directly introduced into a cell contained in the cell population by using lipofection method, liposome method, electroporation method, calcium phosphate coprecipitation method, DEAE dextran method, microinjection method, particle gun method and the like. When two or more different kinds of miRNA-responsive mRNAs are introduced, or miRNA-responsive mRNA and the below-mentioned mRNA to be a control (hereinafter to be also referred to as control mRNA or transfection control) are used, plural mRNAs are preferably co-transfected into a cell population. This is because the ratio of two or more kinds of co-transfected mRNAs in the cell is maintained in each cell, and the activity ratio of the protein expressed from these mRNAs becomes constant in the cell population. The amount of introduction in this case varies depending on the cell population to be introduced, mRNA to be introduced, introduction method and the kind of introduction reagent, those of ordinary skill in the art can appropriately select them to achieve the desired translation amount.

In the present invention, the control mRNA is exemplified by a mRNA containing a sequence encoding a marker protein other than the marker protein contained in the miRNA-responsive mRNA or a sequence encoding a drug resistance protein, but not containing a miRNA target site. A marker protein translated from a control mRNA is preferably a protein that does not cause cell death by translation of the marker protein, and therefore, fluorescent protein, luminescent protein, protein aiding fluorescence, luminescence or color development, and membrane protein are preferably used.

The "drug resistance protein" used in the present invention may be any protein as long as it is resistant to the corresponding drug. For example, it includes a protein encoded in an antibiotic resistance gene, but it is not limited thereto. Examples of the antibiotic resistance gene include kanamycin resistance gene, ampicillin resistant gene, puromycin resistance gene, blasticidin resistance gene, gentamicin resistance gene, kanamycin resistance gene, tetracycline resistance gene, chloramphenicol resistance gene and the like. In the present invention, preferably, puromycin resistance gene or blasticidin resistance gene is used as an antibiotic resistance gene.

A sorting method as one embodiment of the present invention more preferably includes a step of simultaneously introducing miRNA-responsive mRNA and control mRNA into a target cell population. Such step can be preferably performed by co-transfection of miRNA-responsive mRNA and control mRNA. Using the control mRNA, it becomes possible to sort cells, in which the marker protein translated from miRNA-responsive mRNA is low or is not translated, as skeletal muscle precursor cells even when the introduction efficiency of miRNA-responsive mRNA into cells is low. When control mRNA is used in the present invention, those of ordinary skill in the art can also appropriately select the introduction amount of control mRNA to achieve a desired translation amount.

When control mRNA is used in the present invention, the marker protein translated from the control mRNA is preferably different from the marker protein contained in miRNA-responsive mRNA. For example, when the marker protein contained in the miRNA-responsive mRNA is an apoptosis induction protein, the marker protein contained in the control mRNA may be a fluorescent protein. In this case, expression of apoptosis induction protein is suppressed, resulting in cell survival, and cells labeled with a fluorescent protein can be further sorted as the skeletal muscle progenitor cell.

In addition, a control mRNA comprising a sequence encoding a drug resistance protein can be used together with miRNA-responsive mRNA which translates any marker protein. In this case, among the cells resistant to the corresponding drugs, a cell in which the marker protein is not expressed or is reduced can be sorted as the skeletal muscle precursor cell.

On the other hand, when the marker protein contained in the miRNA-responsive mRNA and the marker protein contained in the control mRNA are fluorescent proteins, the both fluorescent proteins desirably have different fluorescence wavelengths.

While the control mRNA in the present invention is not particularly limited, for example, EGFP mRNA, tagBFP mRNA, tagRFP mRNA and the like shown in the Examples can be mentioned.

In the present invention, the step of sorting cells in which the translation amount of the marker protein contained in the aforementioned miRNA-responsive mRNA is small or cannot be detected can be performed by detecting a signal from the marker protein by using a predetermined detection apparatus. Examples of the detection apparatus include, but are not limited to, flow cytometer, imaging cytometer, fluorescence microscope, luminescence microscope, CCD camera and the like. As such detection apparatus, a person skilled in the art can use a suitable one according to the marker protein. For example, when the marker is a fluorescent protein or luminescent protein, it can be sorted using a flow cytometer, and when the marker is a protein aiding fluorescence, luminescence or color development, it can be sorted using a microscope and a culture dish coated with photo-responsive cell culture material, by irradiating light on the cells after color development etc. and utilizing the fact that unirradiated cells are detached from the culture dish. When the marker protein is a membrane localization protein, a method for quantitating a marker protein using a cellular surface protein-specific detection reagent such as an antibody and the above-mentioned detection apparatus is possible, as well as a method of isolating cells without quantitative process of marker protein such as magnetic cell separator (MACS) is possible, and when the marker protein is a drug resistance gene, a method of detecting the expression of the marker protein by drug administration and isolating viable cells is possible.

In the present invention, sorting cells means isolation of skeletal muscle progenitor cells with a high purity from a cell population not subjected to a sorting step using miRNA-responsive mRNA. In the present invention, the purity of the sorted cells is not particularly limited as long as it is high as compared to the case without a sorting step using miRNA-responsive mRNA. It is preferably not less than 60%, and examples thereof include 60%, 70%, 80%, 81%, 82%, 83%, 84%, 85%, 86%, 87%, 88%, 89%, 90%, 91%, 92%, 93%, 94%, 95%, 96%, 97%, 98%, 99% and 100%.

<Pluripotent Stem Cell>

A pluripotent stem cell usable in the present invention is a stem cell having pluripotency permitting differentiation into any cell present in living organisms, and also having proliferation potency. While it is not particularly limited to the following, it includes, for example, embryonic stem (ES) cell, germline stem (GS) cell, embryonic germline (EG) cell, induced pluripotent stem (iPS) cell, embryonic stem cell derived from a cloned embryo obtained by nuclear transplantation (ntES cell), Muse cell and the like. Preferable pluripotent stem cells are ES cell, iPS cell and ntES cell. In view of the use for a myopathy treatment, it is more preferably human ES cell or human iPS cell, further preferably human iPS cell.

(A) Embryonic Stem Cell

ES cell is a stem cell having pluripotency and proliferation potency based on self-replication, which is established from an inner cell mass of an early-stage embryo (e.g., blastocyst) of a mammal such as human, mouse and the like.

ES cell is an embryo-derived stem cell derived from an inner cell mass of blastocyst, which is an embryo after 8-cell stage and molura of a fertilized egg, and has an ability to differentiate into any cell constituting an adult body, i.e., pluripotent differentiation, and proliferation potency based on self-replication. The ES cell was discovered in mouse in 1981 (M. J. Evans and M. H. Kaufman (1981), Nature 292:154-156) and thereafter ES cell lines were also established in primates such as human, monkey and the like (J. A. Thomson et al. (1998), Science 282:1145-1147; J. A. Thomson et al. (1995), Proc. Natl. Acad. Sci. USA, 92: 7844-7848; J. A. Thomson et al. (1996), Biol. Reprod., 55: 254-259; J. A. Thomson and V. S. Marshall (1998), Curr. Top. Dev. Biol., 38:133-165).

ES cell can be established by removing an inner cell mass from the blastocyst of a fertilized egg of a target animal, and culturing the inner cell mass on fibroblast feeder cells. In addition, the cells can be maintained by passage culture using a culture medium added with substances such as leukemia inhibitory factor (LIF), basic fibroblast growth factor (bFGF) and the like. The methods of establishment and maintenance of human and monkey ES cells are described in, for example, U.S. Pat. No. 5,843,780; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; H. Kawasaki et al. (2002), Proc. Natl. Acad. Sci. USA, 99:1580-1585; Klimanskaya I, et al. (2006), Nature. 444:481-485 and the like.

Using, as a culture medium for preparing ES cells, for example, a DMEM/F-12 culture medium supplemented with 0.1 mM 2-mercaptoethanol, 0.1 mM nonessential amino acids, 2 mM L-glutamic acid, 20% KSR and 4 ng/ml bFGF, human ES cells can be maintained under wet atmosphere at 37° C., 2% $CO_2$/98% air (O. Fumitaka et al. (2008), Nat. Biotechnol., 26:215-224). In addition, ES cells require passage every 3-4 days, and the passage in this case can be performed using, for example, 0.25% trypsin and 0.1 mg/ml collagenase IV in PBS containing 1 mM $CaCl_2$ and 20% KSR.

ES cells can be generally selected by the Real-Time PCR method using the expression of a gene marker such as alkaline phosphatase, Oct-3/4, Nanog and the like as an index. Particularly, for selection of human ES cell, expression of a gene marker such as OCT-3/4, NANOG, ECAD and the like can be used as an index (E. Kroon et al. (2008), Nat. Biotechnol., 26:443-452).

As for human ES cell line, for example, WA01(H1) and WA09(H9) are available from WiCell Research Institute, and KhES-1, KhES-2 and KhES-3 are available from Institute for Frontier Medical Sciences, Kyoto University (Kyoto, Japan).

(B) Germuline Stem Cell

Germuline stem cell is a pluripotent stem cell derived from the testis, which becomes the origin for spermatogenesis. This cell can be induced to differentiate into various lines of cells, like ES cells and shows properties of, for example, generation of a chimeric mouse by transplantation into a mouse blastocyst and the like (M. Kanatsu-Shinohara et al. (2003) Biol. Reprod., 69:612-616; K. Shinohara et al. (2004), Cell, 119:1001-1012). It is self-replicable in a culture medium containing a glial cell line-derived neurotrophic factor (GDNF), can produce a germuline stem cell by repeating passages under culture conditions similar to those for ES cells (Masanori Takebayashi et al., (2008), Experimental Medicine, Vol. 26, No. 5(Suppl.), pp. 41-46, YODOSHA (Tokyo, Japan)).

(C) Embryonic Germ Cell

Embryonic germ cell is a cell having pluripotency similar to that of ES cells, which is established from a primordial germ cell at the prenatal period. It can be established by culturing a primordial germ cell in the presence of a substance such as LIF, bFGF, a stem cell factor and the like (Y. Matsui et al. (1992), Cell, 70:841-847; J. L. Resnick et al. (1992), Nature, 359:550-551).

(D) Induced Pluripotent Stem Cell

Induced pluripotent stem (iPS) cell is an artificial stem cell derived from a somatic cell, which can be produced by introducing a specific reprogramming factor in the form of a DNA or protein into a somatic cell, and show almost equivalent property (e.g., pluripotent differentiation and proliferation potency based on self-renewal) as ES cells (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO2007/069666). The reprogramming factor may be constituted with a gene specifically expressed in ES cell, a gene product or non-coding RNA thereof, a gene playing an important role for the maintenance of undifferentiation of ES cell, a gene product or non-coding RNA thereof, or a low molecular weight compound. Examples of the gene contained in the reprogramming factor include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and the like. These reprogramming factors may be used alone or in combination. Examples of the combination of the reprogramming factors include combinations described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290, WO2010/147395, WO2010/147612. Huangfu D, et al. (2008), Nat. Biotechnol., 26: 795-797, Shi Y, et al. (2008), Cell Stem Cell, 2: 525-528, Eminli S, et al. (2008), Stem Cells. 26:2467-2474, Huangfu D, et al. (2008), Nat Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci USA. 106:8912-8917, Kim J B, et al. (2009). Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P, et al. (2010), and Stem Cells. 28:713-720.

Examples of the above-mentioned reprogramming factor include, but are not limited to, factors used for enhancing the establishment efficiency, such as histone deacetylase (HDAC) inhibitors [e.g., low-molecular inhibitors such as valproic acid (VPA), trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29 mer shRNA Constructs against HDAC1 (OriGene) and the like), and the like], MEK inhibitor (e.g., PD184352, PD98059, U0126, SL327 and PD0325901), Glycogen synthase kinase-3 inhibitor (e.g., Bio and CHIR99021), DNA methyl transferase inhibitors (e.g., 5-azacytidine), histone methyl transferase inhibitors [for example, low-molecular inhibitors such as BIX-01294, and nucleic acid-based expression inhibitors such as siRNAs and shRNAs against Suv39h1, Suv39h2, SetDB1 and G9a], L-channel calcium agonist (e.g., Bayk8644), butyric acid, TGF-β inhibitor or ALK5 inhibitor (e.g., LY364947, SB431542, 616453 and A-83-01), p53 inhibitor (e.g., siRNA and shRNA against p53), ARID3A inhibitor (e.g., siRNA and shRNA against ARID3A), miRNA such as miR-291-3p, miR-294, miR-295, mir-302 and the like, Wnt Signaling (e.g., soluble Wnt3a), neuropeptide Y, prostaglandins (e.g., prostaglandin E2 and prostaglandin J2), hTERT, SV40LT, UTF1, IRX6, GLIS1, PITX2, DMRTB1 and the like. In the present specification, these factors used for enhancing the establishment efficiency are not particularly distinguished from the reprogramming factor.

When in the form of a protein, a reprogramming factor may be introduced into a somatic cell by a method, for example, lipofection, fusion with cell penetrating peptide (e.g., TAT derived from HIV and polyarginine), microinjection and the like.

When in the form of a DNA, a reprogramming factor may be introduced into a somatic cell by the method of, for example, vector of virus, plasmid, artificial chromosome and the like, lipofection, liposome, microinjection and the like. Examples of the virus vector include retrovirus vector, lentivirus vector (hereinafter, Cell, 126, pp. 663-676, 2006; Cell, 131, pp. 861-872, 2007; Science, 318, pp. 1917-1920, 2007), adenovirus vector (Science, 322, 945-949, 2008), adeno-associated virus vector, vector of Hemagglutinating Virus of Japan (WO 2010/008054) and the like. Examples of the artificial chromosome vector include human artificial chromosome (HAC), yeast artificial chromosome (YAC), bacterial artificial chromosome (BAC, PAC) and the like. As the plasmid, plasmids for mammalian cells can be used (Science, 322:949-953, 2008). The vector can contain regulatory sequences of promoter, enhancer, ribosome binding sequence, terminator, polyadenylation site and the like so that a nuclear reprogramming substance can be expressed and further, where necessary, a selection marker sequence such as a drug resistance gene (e.g., kanamycin resistance gene, ampicillin resistance gene, puromycin resistance gene and the like), thymidine kinase gene, diphtheria toxin gene and the like, a reporter gene sequence of green fluorescent protein (GFP), β-glucuronidase (GUS), FLAG and the like, and the like. Moreover, the above-mentioned vector may have a LoxP sequence before and after thereof to simultaneously cut out a gene encoding a reprogramming factor or a gene encoding a reprogramming factor bound to the promoter, after introduction into a somatic cell.

When in the form of RNA, for example, it may be introduced into a somatic cell by a means of lipofection, microinjection and the like, and RNA incorporating 5-methylcytidine and pseudouridine (TriLink Biotechnologies) may be used to suppress degradation (Warren L, (2010) Cell Stem Cell. 7:618-630).

Examples of the culture medium for inducing iPS cell include 10-15% FBS-containing DMEM, DMEM/F12 or DME culture medium (these culture media can further contain LIF, penicillin/streptomycin, puromycin, L-glutamine, nonessential amino acids, β-mercaptoethanol and the like as appropriate) or a commercially available culture medium [for example, culture medium for mouse ES cell culture (TX-WES culture medium, Thromb-X Inc.), culture medium for primate ES cell (culture medium for primate ES/iPS cell, Reprocell Inc.), serum-free medium (mTeSR, Stemcell Technologies Inc.)] and the like.

Examples of the culture method include contacting a somatic cell with a reprogramming factor on 10% FBS-containing DMEM or DMEM/F12 culture medium at 37° C. in the presence of 5% $CO_2$ and culturing for about 4-7 days, thereafter reseeding the cells on feeder cells (e.g., mitomycin C-treated STO cells, SNL cells etc.), and culturing the cells in a bFGF-containing culture medium for primate ES cell from about 10 days after the contact of the somatic cell and the reprogramming factor, whereby iPS-like colonies can be obtained after about 30-about 45 days or longer from the contact.

Alternatively, the cells are cultured on feeder cells (e.g., mitomycin C-treated STO cells, SNL cells etc.) at 37° C. in the presence of 5% $CO_2$ in a 10% FBS-containing DMEM culture medium (which can further contain LIF, penicillin/streptomycin, puromycin, L-glutamine, nonessential amino acids, β-mercaptoethanol and the like as appropriate), whereby ES-like colonies can be obtained after about 25-about 30 days or longer. Desirably, a method using a somatic cell itself to be reprogrammed, instead of the feeder cells (Takahashi K, et al. (2009), PLoS One. 4:e8067 or WO2010/137746), or an extracellular substrate (e.g., Laminin-5 (WO2009/123349) and Matrigel (BD)).

Besides the above, a culture method using a serum-free medium can also be recited as an example (Sun N, et al. (2009), Proc Natl Acad Sci USA. 106:15720-15725). Furthermore, to enhance establishment efficiency, an iPS cell may be established under hypoxic conditions (oxygen concentration of not less than 0.1% and not more than 15%) (Yoshida Y, et al. (2009), Cell Stem Cell. 5:237-241 or WO2010/013845).

The culture medium is exchanged with a fresh culture medium once a day between the above-mentioned cultures, from day 2 from the start of the culture. While the cell number of the somatic cells used for nuclear reprogramming is not limited, it is about $5 \times 10^3$-about $5 \times 10^6$ cells per 100 $cm^2$ culture dish.

The iPS cell can be selected based on the shape of the formed colony. When a drug resistance gene which is expressed in association with a gene (e.g., Oct3/4, Nanog) expressed when a somatic cell is reprogrammed is introduced as a marker gene, an established iPS cell can be selected by culturing in a culture medium (selection culture medium) containing a corresponding drug. When the marker gene is a fluorescent protein gene, iPS cell can be selected by observation with a fluorescence microscope, when it is a luminescent enzyme gene, iPS cell can be selected by adding a luminescent substrate, and when it is a chromogenic enzyme gene, iPS cell can be selected by adding a chromogenic substrate.

The term "somatic cell" used in the present specification means any animal cell (preferably, cells of mammals inclusive of human) excluding germ line cells or totipotent cells, such as ovum, oocyte, ES cells and the like. Somatic cell unlimitatively encompasses any of somatic cells of fetuses, somatic cells of neonates, and mature healthy or pathogenic somatic cells, and any of primary cultured cells, passage cells, and established lines of cells. Specific examples of the somatic cell include (1) tissue stem cells (somatic stem cells) such as neural stem cell, hematopoietic stem cell, mesenchymal stem cell, dental pulp stem cell and the like, (2) tissue progenitor cell, (3) differentiated cells such as lymphocyte, epithelial cell, endothelial cell, myocyte, fibroblast (skin cells etc.), hair cell, hepatocyte, gastric mucosal cell, enterocyte, splenocyte, pancreatic cell (pancreatic exocrine cell etc.), brain cell, lung cell, renal cell and adipocyte and the like, and the like.

In the present invention, while the mammal individual as a source of somatic cells is not particularly limited, it is preferably human. When the iPS cells obtained are to be used for the regenerative medical use in humans, it is particularly preferable, from the viewpoint of prevention of graft rejection, that somatic cells are patient's own cells or collected from another person having the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressor and the like. For example, it includes an HLA type wherein major HLAs (the three major loci of HLA-A, HLA-B and HLA-DR or 4 gene loci added with HLA-C) are identical (hereinafter the same meaning shall apply) and the like.

(E) ES Cells Derived from Cloned Embryo by Nuclear Transplantation

An nt ES cell is an ES cell derived from a cloned embryo prepared by a nuclear transplantation technique, and has almost the same property as the ES cell derived from a fertilized egg (T. Wakayama et al. (2001), Science, 292:740-743; S. Wakayama et al. (2005), Biol. Reprod., 72:932-936; J. Byrne et al. (2007), Nature, 450:497-502). That is, an ES cell established from an inner cell mass of a blastocyst derived from a cloned embryo obtained by substituting the nucleus of an unfertilized egg with the nucleus of a somatic cell is an nt ES (nuclear transfer ES) cell. For generation of an nt ES cell, a combination of the nuclear transplantation technique (J. B. Cibelli et al. (1998), Nature Biotechnol., 16:642-646) and the ES cell generation technique (mentioned above) is used (Kiyoka Wakayama et al., (2008), Experimental Medicine, Vol. 26, No. 5(Suppl.), pp. 47-52). In nuclear transplantation, reprogramming can be performed by injecting the nucleus of a somatic cell to an enucleated unfertilized egg of a mammal, and culturing for a few hours.

(F) Multilineage-Differentiating Stress Enduring Cell (Muse Cell)

Muse cell is a pluripotent stem cell produced by the method described in WO2011/007900. In more detail, it is a cell having pluripotency, which is obtained by subjecting a fibroblast or a bone marrow stromal cell to a trypsin treatment for a long time, preferably for 8 hr or for 16 hr, and thereafter culturing the cells in a suspended state, and positive for SSEA-3 and CD105.

<Method of Producing Skeletal Muscle Progenitor Cell from Pluripotent Stem Cell>

According to the present invention, a method including the following steps can be used for producing skeletal muscle progenitor cells from pluripotent cells;

(1) a step of culturing pluripotent stem cells in a culture medium containing a TGF-β inhibitor and a GSK3β inhibitor, (2) a step of culturing the cells obtained in the step of (1) in a culture medium containing a TGF-β inhibitor, a GSK3β inhibitor, IGF1, HGF and bFGF, (3) a step of culturing the cells obtained in the step of (2) in a culture medium containing a TGF-β inhibitor, a GSK3β inhibitor and IGF1, (4) a step of culturing the cells obtained in the step of (3) in a culture medium containing a TGF-β inhibitor, IGF1 and HGF, and (5) a step of culturing the cells obtained in the step of (4) in a culture medium containing a TGF-β inhibitor, IGF1 and serum.

The differentiation induction method of skeletal muscle progenitor cell in the present invention is described in detail below.

Preliminary Preparation for Differentiation Induction

This step may contain a step of culturing pluripotent stem cells prior to differentiation induction of pluripotent stem cells into skeletal muscle progenitor cells. Here, pluripotent stem cells may be separated by any method and cultured by suspension culture, or cultured by adhesion culture using a coating-treated culture dish. In this step, adhesion culture is preferably used. Examples of the separation method of pluripotent stem cells include a method including physical separation, a separation method using a separation solution having protease activity and collagenase activity (e.g., Accutase™, Accumax™ and the like) or a separation solution having collagenase activity alone, a dissociation method using Trypsin/EDTA and the like. Preferably, a method including dissociation of cells by using Trypsin/EDTA is used.

In the present invention, suspension culture means formation of an embryoid by culturing cells in a state of being non-adhesive to the culture dish, and is not particularly limited. To improve adhesiveness to cells, it can be performed using a culture dish free of an artificial treatment (e.g., coating treatment with extracellular matrix and the like) or a culture dish artificially treated to suppress adhesion (e.g., coating treatment with poly-hydroxyethyl methacrylic acid (poly-HEMA)).

In the present invention, adhesion culture can be performed by culturing on feeder cells, or in a culture container coated with an extracellular substrate. The coating treatment can be performed by appropriately removing a solution containing an extracellular substrate after placing the solution in a culture container.

In the present invention, a feeder cell means other cell that plays an auxiliary role to adjust culture conditions for the object cell. In the present invention, the extracellular substrate is a supramolecular architecture present outside a cell, and may be derived from nature or an artificial material (recombinant). For example, substances such as collagen, proteoglycan, fibronectin, hyaluronic acid, tenascin, entactin, elastin, fibrillin, laminin and fragments of these can be mentioned. These extracellular substrates may be used in combination and may be, for example, a material prepared from cells such as BD Matrigel™ and the like. As an artificial material, a fragment of laminin is recited as an example. In the present invention, laminin is a protein having a heterotrimer structure having one α chain, one β chain, and one γ chain, and is not particularly limited. For example, α chain is α1, α2, α3, α4 or α5, β chain is β1, β2 or β3, and γ chain is γ1, γ2 or γ3. In the present invention, a fragment of laminin is not particularly limited as long as it is a fragment of laminin having an integrin-binding activity, and examples thereof include E8 fragment obtained by digestion with elastase.

A step of culturing pluripotent stem cells prior to the differentiation induction of pluripotent stem cells into skeletal muscle progenitor cells is preferably adhesion culture, and the adhesion culture can be adhesion culture using a culture container coated with Matrigel™. The culture medium used in the step of culturing pluripotent stem cells can be prepared using a medium used for culturing animal cells as the basal medium. Examples of the basal medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, StemPro34 (invitrogen), RPMI-base medium, mTeSR1, a mixed medium of these and the like. In this step, mTeSR1 is preferably used. The medium may contain a serum, or may be serum-free. Where necessary, the medium may contain one or more serum replacements such as albumin, transferrin, Knockout Serum Replacement (KSR) (serum replacement for FBS in ES cell culture), N2 supplement (Invitrogen), B27 supplement (Invitrogen), fatty acid, insulin, collagen precursor, trace element, 2-mercaptoethanol (2 ME), thiolglycerol and the like, and may contain one or more substances such as lipid, amino acid, L-glutamine, Glutamax (Invitrogen), non-essential amino acid, vitamin, growth factor, low-molecular-weight compound, antibiotic, antioxidant, pyruvic acid, buffering agent, inorganic salt and the like. Preferable medium is mTeSR1.

The culture period in the step of culturing pluripotent stem cells is, for example, not less than 1 day and not more than 10 days, such as 1 day, 2 days, 3 days, 4 days, 5 days, 6 days, 7 days, 8 days, 9 days, 10 days and the like, preferably 4 days.

When pluripotent stem cells are separated in a step of culturing pluripotent stem cells, the medium preferably contains a ROCK inhibitor. The ROCK inhibitor is not particularly limited as long as it can suppress the function of Rho kinase (ROCK) and, for example, Y-27632 can be preferably used in the present invention.

While the concentration of Y-27632 in the medium is not particularly limited, it is preferably 1 μM-50 μM, and examples thereof include, but are not limited to, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 25 μM, 30 μM, 35 μM, 40 μM, 45 μM, 50 μM. It is more preferably 10 μM.

The period of adding a ROCK inhibitor to the medium may be the culture period in the step of culturing pluripotent stem cells, and only needs to be the period of suppressing cell death when dispersing single cells, which is, for example, at least one day.

In the step of culturing pluripotent stem cells, while the incubation temperature is not limited to the following, it is about 30-40° C., preferably about 37° C., and the culture is performed under the atmosphere of $CO_2$-containing air. The $CO_2$ concentration is preferably about 2-5%, preferably 5%.

In the step of culturing pluripotent stem cells, the medium can be exchanged during the culture period. The medium used for medium exchange may be a medium containing the same components as in the medium before exchange or a medium containing different components. Preferably, a medium containing the same components is used. While the timing of medium exchange is not particularly limited, it is performed, for example, every 1 day, every 2 days, every 3 days, every 4 days, every 5 days, from the start of culture in a fresh medium. In this step, the medium is preferably exchanged every 2 days.

Step (1): A Step of Culturing Pluripotent Stem Cells in a Culture Medium Containing a TGF-β Inhibitor and a GSK3β Inhibitor Step (1) is a step of culturing pluripotent stem cells in a culture medium containing a TGF-β inhibitor and a GSK3β inhibitor. The culture medium used in Step (1) can be prepared using a medium used for culturing animal cells as the basal medium. Examples of the basal medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, StemPro34 (invitrogen), RPMI-base medium, a mixed medium of these and the like. In Step (1), preferred is a mixed medium of IMDM medium and Ham's F12 medium.

The basal medium may contain a serum, or may be serum-free. Where necessary, the medium may contain one or more serum replacements such as albumin, transferrin, Knockout Serum Replacement (KSR) (serum replacement for FBS in ES cell culture), N2 supplement (Invitrogen), B27 supplement (Invitrogen), fatty acid, insulin, selenium (sodium selenite), collagen precursor, trace element, 2-mercaptoethanol (2 ME), thiolglycerol and the like, and may contain one or more substances such as lipid, amino acid, L-glutamine, Glutamax (Invitrogen), non-essential amino acid, vitamin, growth factor, low-molecular-weight compound, antibiotic, antioxidant, pyruvic acid, buffering agent, inorganic salt and the like. In Step (1), a preferable basal medium is a mixed medium of IMDM medium and Ham's F12 medium added with albumin, transferrin, fatty acid, insulin, selenium and thiolglycerol.

In the present invention, the TGF-β inhibitor is not particularly limited as long as it is a substance that inhibits signal transduction from the binding of TGF-β to a receptor to SMAD. Examples thereof include a substance that inhibits its binding to ALK family as a receptor of TGF-β, a substance that inhibits phosphorylation of SMAD by ALK family and the like. In the present invention, examples of the TGF-β inhibitor include Lefty-1 (for example, mouse: NM_010094, human: NM_020997 in NCBI Accession No.), SB431542, SB202190 (all above, R. K. Lindemann et al., Mol. Cancer, 2003, 2:20), SB505124 (GlaxoSmithKline), NPC30345, SD093, SD908, SD208 (Scios), LY2109761, LY364947, LY580276 (Lilly Research Laboratories), A-83-01 (WO 2009146408) and derivatives of these and the like.

The TGF-β inhibitor used in Step (1) may preferably be SB431542.

While the concentration of SB431542 in the medium is not particularly limited, it is preferably 1 μM-50 μM, and examples thereof include, but are not limited to, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 25 μM, 30 μM, 35 μM, 40 μM, 45 μM, 50 μM. It is more preferably 10 μM.

In the present invention, the GSK3β inhibitor is defined as a substance that inhibits kinase activity (e.g., β-catenin phosphorylating ability) of GSK3β protein, and many are already known. Examples thereof include Lithium chloride (LiCl) found for the first time as a GSK3β inhibitor, BIO (alias, GSK3β inhibitor IX; 6-bromo indirubin 3'-oxime) as an indirubin derivative, SB216763 (3-(2,4-dichlorophenyl)-4-(1-methyl-1H-indol-3-yl)-1H-pyrrole-2,5-dione) as a maleimide derivative, GSK3β inhibitor VII (4-dibromoacetophenone) which is a phenyl α bromomethylketone compound, cellular membrane permeation type phosphorylating peptide, L803-mts (alias, GSK3β peptide inhibitor) and CHIR99021 (6-[2-[4-(2,4-Dichlorophenyl)-5-(4-methyl-1H-imidazol-2-yl)pyrimidin-2-ylamino]ethylamino]pyridine-3-carbonitrile) having high selectivity. These compounds are commercially available from, for example, Calbiochem Ltd., Biomol Inc. and the like and can be utilized with ease. They may be obtained from other supply source or may be produced by oneself.

The GSK3β inhibitor used in Step (1) may preferably be CHIR99021.

While the concentration of CHIR99021 in the medium is not particularly limited, it is within the range of, for example, 1 μM-50 μM, preferably 5 μM-50 μM, and examples thereof include, but are not limited to, 5 μM, 6 μM, 7 μM, 8 μM, 9 μM, 10 μM, 15 μM, 20 μM, 25 μM, 30 μM, 35 μM, 40 μM, 45 μM, 50 μM. Preferably, a concentration higher than 1 μM, which is the concentration used for inhibiting GSK3β, is used, and more preferred is not less than 5 μM.

In Step (1), the culture period is, for example, not less than 10 days and not more than 30 days, such as 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days and the like, preferably 21 days.

In Step (1), while the incubation temperature is not limited to the following, it is about 30-40° C., preferably about 37° C., and the culture is performed under the atmosphere of $CO_2$-containing air. The $CO_2$ concentration is preferably about 2-5%, preferably 5%.

In Step (1), to increase the content percentage of desired cells, passage is preferably contained in the step. In the present invention, passage is an operation to dissociate cells under culture from a container and reseed them. In the step of dissociating cells, cells adhered to each other to form a population are dissociated (separated) into each cell. Examples of the method for dissociating cells include a method including physical dissociation, a dissociation method using a dissociation solution having a protease activity and a collagenase activity (e.g., Accutase™ and Accumax™ and the like), a dissociation solution having only a collagenase activity, a dissociation method using Trypsin/EDTA and the like. Preferably, a method of dissociating cells by using Trypsin/EDTA is used.

In Step (1), while passage is not particularly limited, it is performed every 4-10 days, for example, every 4 days, every 5 days, every 6 days, every 7 days, every 8 days, every 9 days, every 10 days, preferably, every 7 days, from the start of this step.

The culture medium immediately after passage may contain a ROCK inhibitor to prevent cell death of the reseeded cells. The ROCK inhibitor can be used under conditions similar to those mentioned above.

In Step (1), it is desirable to exchange medium as appropriate. While the timing of medium exchange is not particularly limited, it is performed, for example, every 1 day, every 2 days, every 3 days, every 4 days, every 5 days, from the start of culture in a fresh medium. In this step, the medium is preferably exchanged every 2 days.

Step (2): A Step of Culturing in a Culture Medium Containing a TGF-β Inhibitor, a GSK3β Inhibitor, IGF1, HGF and bFGF Step (2) is a step of culturing the cells obtained in the above-mentioned Step (1) in a culture medium containing a TGF-β inhibitor, a GSK3β inhibitor, IGF1, HGF and bFGF. The culture medium used in Step (2) can be prepared using a medium used for culturing animal cells as the basal medium. Examples of the basal medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, StemPro34 (invitrogen), RPMI-base medium, SF-03 medium (Eidia CO., Ltd.), a mixed medium of these and the like. In Step (2), SF-03 medium is preferably used.

The basal medium may contain a serum, or may be serum-free. Where necessary, the medium may contain one or more serum replacements such as albumin, transferrin, Knockout Serum Replacement (KSR) (serum replacement for FBS in ES cell culture), N2 supplement (Invitrogen), B27 supplement (Invitrogen), fatty acid, insulin, selenium (sodium selenite), collagen precursor, trace element, 2-mercaptoethanol (2 ME), thiolglycerol and the like, and may contain one or more substances such as lipid, amino acid, L-glutamine, Glutamax (Invitrogen), non-essential amino acid, vitamin, growth factor, low-molecular-weight compound, antibiotic, antioxidant, pyruvic acid, buffering agent, inorganic salt and the like. In Step (2), preferable basal medium is SF-03 medium added with albumin and 2-mercaptoethanol.

As the TGF-β inhibitor to be used in Step (2), those similar to the aforementioned can be used, with preference given to SB431542. While the concentration of SB431542 in the medium used in Step (2) is not particularly limited, it is preferably 1 μM-50 μM, and examples thereof include, but are not limited to, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 25 μM, 30 μM, 35 μM, 40 μM, 45 μM, 50 μM. It is more preferably 10 μM.

As the GSK3β inhibitor to be used in Step (2), those similar to the aforementioned can be used, with preference given to LiCl. While the concentration of LiCl in the medium used in Step (2) is not particularly limited, it is preferably 1 mM-50 mM, and examples thereof include, but are not limited to, 1 mM, 2 mM, 3 mM, 4 mM, 5 mM, 6 mM, 7 mM, 8 mM, 9 mM, 10 mM, 15 mM, 20 mM, 25 mM, 30 mM, 40 mM, 50 mM. It is more preferably 5 mM.

While the concentration of IGF1 in the medium used in Step (2) is not particularly limited, it is within the range of, for example, 1 ng/ml-100 ng/ml, preferably 1 ng/ml-50 ng/ml, and examples thereof include, but are not limited to, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 g/ml, 40 ng/ml, 45 ng/ml, 50 ng/ml, 60 ng/ml, 70 ng/ml, 80 ng/ml, 90 ng/ml, 100 ng/ml. It is more preferably 10 ng/ml.

While the concentration of HGF in the medium used in Step (2) is not particularly limited, it is within the range of, for example, 1 ng/ml-100 ng/ml, preferably 1 ng/ml-50 ng/ml, and examples thereof include, but are not limited to, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 g/ml, 40 ng/ml, 45 ng/ml, 50 ng/ml, 60 ng/ml, 70 ng/ml, 80 ng/ml, 90 ng/ml, 100 ng/ml. It is more preferably 10 ng/ml.

While the concentration of bFGF in the medium used in Step (2) is not particularly limited, it is within the range of, for example, 1 ng/ml-100 ng/ml, preferably 1 ng/ml-50 ng/ml, and examples thereof include, but are not limited to, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 g/ml, 40 ng/ml, 45 ng/ml, 50 ng/ml, 60 ng/ml, 70 ng/ml, 80 ng/ml, 90 ng/ml, 100 ng/ml. It is more preferably 10 ng/ml.

In Step (2), the culture period is, for example, not less than 1 day and not more than 10 days, such as 1 day, 2 days, 3 days, 4 days, 5 days, 6 days, 7 days, 8 days, 9 days, 10 days and the like, preferably 4 days.

In Step (2), while the culture temperature is not limited to the following, it is about 30-40° C., preferably about 37° C., and the culture is performed under the atmosphere of $CO_2$-containing air. The $CO_2$ concentration is preferably about 2-5%, preferably 5%.

Step (3): A Step of Culturing in a Culture Medium Containing a TGF-β Inhibitor, a GSK3β Inhibitor and IGF1

Step (3) is a step of culturing the cells obtained in the above-mentioned Step (2) in a culture medium containing a TGF-β inhibitor, a GSK3β inhibitor and IGF1. The culture medium used in Step (3) can be prepared using a medium used for culturing animal cells as the basal medium. Examples of the basal medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, StemPro34 (invitrogen), RPMI-base medium, SF-03 medium, a mixed medium of these and the like. In Step (3), SF-03 medium is preferably used.

The basal medium may contain a serum, or may be serum-free. Where necessary, the medium may contain one or more serum replacements such as albumin, transferrin, Knockout Serum Replacement (KSR) (serum replacement for FBS in ES cell culture), N2 supplement (Invitrogen), B27 supplement (Invitrogen), fatty acid, insulin, selenium (sodium selenite), collagen precursor, trace element, 2-mercaptoethanol (2 ME), thiolglycerol and the like, and may contain one or more substances such as lipid, amino acid, L-glutamine, Glutamax (Invitrogen), non-essential amino acid, vitamin, growth factor, low-molecular-weight compound, antibiotic, antioxidant, pyruvic acid, buffering agent, inorganic salt and the like. In Step (3), preferable basal medium is SF-03 medium added with albumin and 2-mercaptoethanol.

As the TGF-β inhibitor to be used in Step (3), those similar to the aforementioned can be used, with preference given to SB431542. While the concentration of SB431542 in the medium used in Step (3) is not particularly limited, it is preferably 1 μM-50 μM, and examples thereof include, but are not limited to, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 25 μM, 30 μM, 35 μM, 40 μM, 45 μM, 50 μM. It is more preferably 10 μM.

As the GSK3β inhibitor to be used in Step (3), those similar to the aforementioned can be used, with preference given to LiCl. While the concentration of LiCl in the medium used in Step (3) is not particularly limited, it is preferably 1 mM-50 mM, and examples thereof include, but are not limited to, 1 mM, 2 mM, 3 mM, 4 mM, 5 mM, 6 mM, 7 mM, 8 mM, 9 mM, 10 mM, 15 mM, 20 mM, 25 mM, 30 mM, 40 mM, 50 mM. It is more preferably 5 mM.

While the concentration of IGF1 in the medium used in Step (3) is not particularly limited, it is within the range of, for example, 1 ng/ml-100 ng/ml, preferably 1 ng/ml-50 ng/ml, and examples thereof include, but are not limited to, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 g/ml, 40 ng/ml, 45 ng/ml, 50 ng/ml, 60 ng/ml, 70 ng/ml, 80 ng/ml, 90 ng/ml, 100 ng/ml. It is more preferably 10 ng/ml.

In Step (3), the culture period is, for example, not less than 1 day and not more than 10 days, and can be, for example, 1 day, 2 days, 3 days, 4 days, 5 days, 6 days, 7 days, 8 days, 9 days, 10 days and the like, preferably 3 days.

In Step (3), while the culture temperature is not limited to the following, it is about 30-40° C., preferably about 37° C., and the culture is performed under the atmosphere of $CO_2$-containing air. The $CO_2$ concentration is preferably about 2-5%, preferably 5%.

Step (4): A Step of Culturing in a Culture Medium Containing a TGF-β Inhibitor, IGF1 and HGF Step (4) is a step of culturing the cells obtained in the aforementioned Step (3) in a culture medium containing a TGF-β inhibitor, IGF1 and HGF. The culture medium used in Step (4) can be prepared using a medium used for culturing animal cells as the basal medium. Examples of the basal medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, StemPro34 (invitrogen), RPMI-base medium, SF-03 medium, a mixed medium of these and the like. In Step (4), SF-03 medium is preferably used.

The basal medium may contain a serum, or may be serum-free. Where necessary, the medium may contain one or more serum replacements such as albumin, transferrin, Knockout Serum Replacement (KSR) (serum replacement for FBS in ES cell culture), N2 supplement (Invitrogen), B27 supplement (Invitrogen), fatty acid, insulin, selenium (sodium selenite), collagen precursor, trace element, 2-mercaptoethanol (2 ME), thiolglycerol and the like, and may contain one or more substances such as lipid, amino acid, L-glutamine, Glutamax (Invitrogen), non-essential amino acid, vitamin, growth factor, low-molecular-weight compound, antibiotic, antioxidant, pyruvic acid, buffering agent, inorganic salt and the like. In Step (4), preferable basal medium is SF-03 medium added with albumin and 2-mercaptoethanol.

As the TGF-β inhibitor to be used in Step (4), those similar to the aforementioned can be used, with preference given to SB431542. While the concentration of SB431542 in the medium used in Step (4) is not particularly limited, it is preferably 1 μM-50 μM, and examples thereof include, but are not limited to, 1 μM, 2 μM, 3 μM, 4 μM, 5 μM, 6 μM, 7 μM, 8 μM, 9 μM, 10 μM, 11 μM, 12 μM, 13 μM, 14 μM, 15 μM, 16 μM, 17 μM, 18 μM, 19 μM, 20 μM, 25 μM, 30 μM, 35 μM, 40 μM, 45 μM, 50 μM. It is more preferably 10 μM.

While the concentration of IGF1 in the medium used in Step (4) is not particularly limited, it is within the range of, for example, 1 ng/ml-100 ng/ml, preferably 1 ng/ml-50 ng/ml, and examples thereof include, but are not limited to, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 g/ml, 40 ng/ml, 45 ng/ml, 50 ng/ml, 60 ng/ml, 70 ng/ml, 80 ng/ml, 90 ng/ml, 100 ng/ml. It is more preferably 10 ng/ml.

While the concentration of HGF in the medium used in Step (4) is not particularly limited, it is within the range of, for example, 1 ng/ml-100 ng/ml, preferably 1 ng/ml-50 ng/ml, and examples thereof include, but are not limited to, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 g/ml, 40 ng/ml, 45 ng/ml, 50 ng/ml, 60 ng/ml, 70 ng/ml, 80 ng/ml, 90 ng/ml, 100 ng/ml. It is more preferably 10 ng/ml.

In Step (4), the culture period is, for example, not less than 7 days and not more than 20 days, and can be, for example, 7 days, 8 days, 9 days, 10 days, 11 days, 12 days, 13 days, 14 days, 15 days, 16 days, 17 days, 18 days, 19 days, 20 days and the like, preferably 14 days.

In Step (4), while the culture temperature is not limited to the following, it is about 30-40° C., preferably about 37° C., and the culture is performed under the atmosphere of $CO_2$-containing air. The $CO_2$ concentration is preferably about 2-5%, preferably 5%.

In Step (4), it is desirable to exchange medium as appropriate. While the timing of medium exchange is not particularly limited, it is performed, for example, every 1 day, every 2 days, every 3 days, every 4 days, every 5 days, preferably every 2 days, from the start of culture in a fresh medium. Alternatively, from another viewpoint, the medium can be exchanged, for example, once per week, twice per week, 3 times per week, 4 times per week, preferably twice per week, from the start of culture in a fresh medium.

Step (5): A Step of Culturing in a Culture Medium Containing a TGF-β Inhibitor, IGF1 and Serum Step (5) is a step of culturing the cells obtained in the aforementioned Step (4) in a culture medium containing a TGF-β inhibitor, IGF1 and serum. The culture medium used in Step (5) can be prepared using a medium used for culturing animal cells as the basal medium. Examples of the basal medium include IMDM medium, Medium 199 medium, Eagle's Minimum Essential Medium (EMEM) medium, αMEM medium, Dulbecco's modified Eagle's Medium (DMEM) medium, Ham's F12 medium, RPMI 1640 medium, Fischer's medium, StemPro34 (invitrogen), RPMI-base medium, a mixed medium of these and the like. In Step (5), DMEM medium is preferably used.

The basal medium may contain a serum, or may be serum-free. Where necessary, the medium may contain one or more serum replacements such as albumin, transferrin, Knockout Serum Replacement (KSR) (serum replacement for FBS in ES cell culture), N2 supplement (Invitrogen), B27 supplement (Invitrogen), fatty acid, insulin, selenium (sodium selenite), collagen precursor, trace element, 2-mercaptoethanol (2 ME), thiolglycerol and the like, and may contain one or more substances such as lipid, amino acid, L-glutamine, Glutamax (Invitrogen), non-essential amino acid, vitamin, growth factor, low-molecular-weight compound, antibiotic, antioxidant, pyruvic acid, buffering agent, inorganic salt and the like. In Step (5), preferable basal medium is DMEM medium added with serum, L-glutamine and 2-mercaptoethanol. The serum to be used in Step (5) is preferably horse serum and the concentration thereof in the basal medium is 1 to 10%, more preferably 2%.

As the TGF-β inhibitor to be used in Step (5), those similar to the aforementioned can be used, with preference given to SB431542. While the concentration of SB431542 in the medium used in Step (5) is not particularly limited, it is preferably 500 nM-50 µM, and examples thereof include, but are not limited to, 500 nM, 600 nM, 700 nM, 800 nM, 900 nM, 1 µM, 2 µM, 3 µM, 4 µM, 5 µM, 6 µM, 7 µM, 8 µM, 9 µM, 10 µM, 15 µM, 20 µM, 25 µM, 30 µM, 35 µM, 40 µM, 45 µM, 50 µM. More preferably, it is 5 µM.

While the concentration of IGF1 in the medium used in Step (5) is not particularly limited, it is within the range of, for example, 1 ng/ml-100 ng/ml, preferably 1 ng/ml-50 ng/ml, and examples thereof include, but are not limited to, 1 ng/ml, 2 ng/ml, 3 ng/ml, 4 ng/ml, 5 ng/ml, 6 ng/ml, 7 ng/ml, 8 ng/ml, 9 ng/ml, 10 ng/ml, 15 ng/ml, 20 ng/ml, 25 ng/ml, 30 ng/ml, 35 g/ml, 40 ng/ml, 45 ng/ml, 50 ng/ml, 60 ng/ml, 70 ng/ml, 80 ng/ml, 90 ng/ml, 100 ng/ml. It is more preferably 10 ng/ml.

In Step (5), while the culture period does not have a particular upper limit since a long-term culture period does not particularly influence induction of skeletal muscle progenitor cells, it is, for example, not less than 9 days and not more than 100 days, and preferably not less than 9 days and not more than 75 days, not less than 9 days and not more than 60 days. For example, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, and 53 days and the like can be mentioned.

In Step (5), while the culture temperature is not limited to the following, it is about 30-40° C., preferably about 37° C., and the culture is performed under the atmosphere of $CO_2$-containing air. The $CO_2$ concentration is preferably about 2-5%, preferably 5%.

In Step (5), it is desirable to exchange medium as appropriate. While the timing of medium exchange is not particularly limited, it is performed, for example, every 1 day, every 2 days, every 3 days, every 4 days, every 5 days, preferably every 2 days, from the start of culture in a fresh medium. Alternatively, from another viewpoint, the medium can be exchanged, for example, once per week, twice per week, 3 times per week, 4 times per week, preferably twice per week, from the start of culture in a fresh medium.

<Kit for Production of Skeletal Muscle Progenitor Cell from Pluripotent Stem Cell>

In one embodiment, the present invention provides a kit for production of a skeletal muscle progenitor cell from a pluripotent stem cell. The kit can contain, in addition to the above-mentioned miRNA-responsive mRNA, a skeletal muscle progenitor cell inducer containing particular factors for induction of skeletal muscle progenitor cells (e.g., lyophilizate, frozen liquid agent dissolved in suitable buffer and the like), cells, reagent and culture medium. This kit may further contain a protocol or instructions describing the step of differentiation induction.

<Myopathy Therapeutic Agent>

The present invention provides a therapeutic agent for myopathy, which contains skeletal muscle progenitor cells sorted by the aforementioned method.

Examples of the myogenic disease in the present invention include myodystrophy [e.g., Duchenne's muscular disease (DMD), Becker type muscular disease, congenital muscular dystrophy, limb-girdle muscular dystrophy, myotonic myodystrophy and the like], hereditary myopathies such as congenital myopathy, distal myopathy and mitochondrial myopathy, non-hereditary myopathies muscular dystrophy such as polymyositis, dermatomyositis and myasthenia gravis, glycogen storage disease, and periodic paralysis. A more preferable target is myodystrophy.

In the present invention, when sorted skeletal muscle progenitor cells are used as a therapeutic agent for myopathy, they are preferably used after re-culturing in a culture medium. A culture medium to be used for re-culturing can be prepared using a medium used for culturing animal cells as a basal medium and, for example, a medium similar to the aforementioned Step (5) is used, though the medium is not limited thereto.

While the re-culturing period may be any as long as it is a period that increases the engrafted rate in the transplant recipient when skeletal muscle progenitor cells are transplanted, it may be, for example, not less than 6 hr and not more than 60 hr, such as 6 hr, 12 hr, 18 hr, 24 hr, 30 hr, 36 hr, 42 hr, 48 hr, 54 hr, 60 hr and the like, preferably 24 hr.

As a skeletal muscle progenitor cell for treating myodystrophy and other hereditary myopathies, a skeletal muscle progenitor cell differentiated from a pluripotent stem cell induced from a person, having the same or substantially the same type of HLA as the patient's, is preferably used. In human regenerative medicine, it is difficult to obtain human ES cells having the same or substantially the same type of HLA; therefore, it is preferable to use a human iPS cell as a pluripotent stem cell for inducing a skeletal muscle progenitor cell.

In another embodiment, it is possible to use a skeletal muscle progenitor cell differentiated from an iPS cell derived from a somatic cell of the patient, as a skeletal muscle progenitor cell for the treatment of hereditary myopathies. For example, since an iPS cell induced from a somatic cell of a DMD patient lacks the dystrophin gene, the normal dystrophin gene is transferred to the iPS cell. The dystrophin cDNA is 14 kb in full-length, and the adeno-associated virus (AAV) vector, which is best suited for transfection to muscle cells, can only accommodate a length of up to about 4.5 kb. For this reason, current strategic attempts of gene therapy include transfer of a shortened functional dystrophin gene [micro-dystrophin gene (3.7 kb)] using the AAV vector, transfer of a 6.4 kb mini-dystrophin gene using a retrovirus/lentivirus vector enabling insertion of a larger DNA, or transfer of the full-length dystrophin gene in a bare state or using a Gutted adenovirus vector. In case of an iPS cell, the highest transfer efficiency is achieved using retrovirus/lentivirus, but a full-length cDNA can be transferred using an artificial chromosome; this offers an advantage of a broader range of choices of gene therapy. In case of limb-girdle muscular dystrophy, which is caused by an abnormality of the sarcoglycan gene, the gene may be transferred to the iPS cell. Alternatively, the mutated site in the causal gene can be repaired on the basis of the endogenous DNA repair mechanism or homologous recombination of the iPS cell. Specifically, a chimeric RNA/DNA oligonucleotide (chimeraplast) having the normalized sequence at the mutated site is transferred and allowed to bind to the target sequence and form a mismatch, whereby the endogenous mechanism for DNA repair is activated to induce gene repair. Alternatively, gene repair can also be achieved by transferring a 400-800-base single-stranded DNA that is homologous to the mutated site to cause homologous recombination. Thus-obtained iPS cell with the repaired causal gene of the disease is induced to differentiate into a skeletal muscle progenitor cell via the foregoing steps, whereby a normal skeletal muscle progenitor cell derived from the patient can be produced.

Since any patient with a hereditary myopathy innately lacks normal gene products, an immune response to a normal gene product (e.g., dystrophin) can occur even when the patient's own skeletal muscle progenitor cell is used. In all cases, it is preferable to use an immunosuppressant concurrently in transplanting skeletal muscle progenitor cells. Alternatively, to avoid this immune response, in case of DMD, the eutrophin gene, a dystrophin homologue also expressed in the patient's skeletal muscles, may be transferred as a substitute for the dystrophin function.

The skeletal muscle progenitor cells sorted by the method of the present invention can also be formulated in the form of cells.

In the present invention, a preparation can be produced as parenteral formulation, an injection, suspension, or drip infusion and the like, in a mixture with a pharmaceutically acceptable carrier, by a conventional means. Examples of the pharmaceutically acceptable carrier that can be contained in the parenteral preparation include aqueous liquids for injection, such as physiological saline and isotonic solutions containing glucose and other auxiliary drugs (e.g., D-sorbitol, D-mannitol, sodium chloride and the like). The agent of the present invention may be formulated with, for example, a buffering agent (e.g., phosphate buffer solution, sodium acetate buffer solution), a soothing agent (e.g., lidocaine hydrochloride, procaine hydrochloride and the like), a stabilizer (e.g., human serum albumin, polyethylene glycol and the like), a preservative (e.g., sodium benzoate, benzalkonium chloride, and the like), an anti-oxidant (e.g., ascorbic acid, sodium edetate and the like) and the like.

When the agent of the present invention is prepared as an aqueous suspension, skeletal muscle progenitor cells are suspended in one of the aforementioned aqueous liquids to obtain a cell density of about $1.0 \times 10^6$ to about $1.0 \times 10^7$ cells/mL. The preparation thus obtained is stable and less toxic, and can be safely administered to mammals such as humans. Although the method of administration is not particularly limited, the preparation is preferably administered by injection or drip infusion, including intravenous administration, intra-arterial administration, intramuscular administration (topical administration to affected site) and the like. The dose of the agent of the present invention varies depending on the subject of administration, treatment target site, symptoms, method of administration and the like. For a DMD patient (assuming a 60 kg body weight), in the case of intravenous administration, for example, it is usually convenient to administer the agent in an amount of about $1.0 \times 10^5$ to about $1 \times 10^7$ cells, based on the amount of skeletal muscle progenitor cells per dose, about 4 to about 8 times at about 1- to 2-week intervals.

While the present invention is explained in more detail in the following by referring to Examples, it is needless to say that the present invention is not limited thereto.

EXAMPLES

<Method of Differentiation Induction of iPS Cell into Skeleton Muscle Cell by Dox-MYOD1 Forced Expression>

Human iPS cell capable of Dox-dependent forced expression of MYOD1 (hereinafter to be referred to as MYOD1-hiPSCs) was supplied by Dr. Hidetoshi Sakurai in Center for iPS Cell Research and Application and used (PLoS One. 2013 Apr. 23; 8(4): e61540). MYOD1-hiPSCs were induced to differentiate into skeleton muscle cells. In detail, the cells were cultured in iPS medium (Primates ES Cell Medium: Reprocell # RCHEMD001) free of bFGF in a 24 well plate coated with Matrigel (BD bioscience). After 24 hr, 1 µg/mL doxycycline (LKT Laboratries) was added to the medium. After another 24 hr, the medium was exchanged with differentiation induction medium-1 (Table 4) and the cells were cultured up to day 9 of differentiation.

TABLE 4

| reagent | part by volume |
|---|---|
| aMEM basal media | 95 |
| 100 mM 2-ME | 0.2 |
| 1 mg/ml Doxycyclin | 0.1 |
| KSR | 5 |

<PAX3-GFP, MYF5-tdTomato Reporter iPS Cell>

Human iPS cells (201B7) supplied by Prof. Yamanaka of Kyoto University were cultured in a conventional method (Takahashi K, et al. Cell. 131:861-72, 2007). Said 201B7 was subjected to homologous recombination using BAC construct according to a conventional method to link EGFP sequence to the 3'-side of the initiation codon of the Pax3 gene locus, whereby iPS cell line (PAX3-GFP iPSCs) that expresses EGFP in cooperation with the expression of PAX3 was generated. Similarly, 201B7 was subjected to homologous recombination using CRISPR/CAS9 system according to a conventional method to link tdTomato sequence to the 5'-side of the initiation codon of the MYF5 gene locus, whereby iPS cell line (MYF5-tdTomato C3 iPSCs) that expresses tdTomato in cooperation with the expression of MYF5 was generated. In both cell lines, gene recombination in single-allele alone was confirmed.

<Diseased iPS Cell Line>

It was prepared according to the method described in Okita K et al., Nat Methods. 8:409-412, 2011 by using fibroblast obtained by culturing skin collected from faciouscapulohumeral muscular dystrophy patients with consent and Epi5 Episomal iPSC Reprogramming Kit (Life Technologies) (hereinafter to be referred to as diseased iPS cell line).

<Method of Differentiation Induction into Skeletal Muscle Progenitor Cell> iPS cells (PAX3-GFP iPSCs, MYF5-tdTomato C3 iPSCs, 201B7, or diseased iPS cell line) were induced to differentiate into skeleton muscle cells. To be specific, to iPS cells cultured on a 6 well plate coated with Matrigel (BD bioscience) were added CDMi basic medium (1:1 IMDM (Invitrogen) and F12 (Invitrogen) mixed medium supplemented with 1% Albumin from bovine serum (SIGMA), 1% Penicillin-Streptomycin Mixed Solution (26253-84 Nacalai Tesque), 1% CD Lipid Concentrate (Invitrogen), 1% Insulin-Trandferin-Selenium (Invitrogen) and 0.5 mM 1-Thioglycerol (SIGMA)) with 10 µM SB431542 and 5 µM CHIR99021 (hereinafter to be referred to as differentiation medium A) and the cells were cultured. Thereafter, the medium was exchanged every two days. The cells were passaged 7 days later, differentiation medium A was added to the iPS cells cultured in a 6 well plate coated with Matrigel (BD bioscience) and the cells were cultured. Thereafter, the medium was exchanged every two days. The cells were passaged 7 days later, differentiation medium A was added to the 6 well plate coated with Matrigel (BD bioscience) and the cells were cultured. After 24 hr, the medium was exchanged with differentiation medium A. Thereafter, the medium was exchanged every two days. Furthermore, 6 days later (14 days after initial day of induction), the cells were passaged, the differentiation medium A was added to a 6 well plate coated with Matrigel (BD bioscience) and the cells were cultured. After 24 hr, the medium was exchanged with differentiation medium A. Thereafter, the medium was exchanged every two days. Furthermore, 6 days later (21 days after initial day of induction), the medium was exchanged with SF-03 basic medium (SF-03 (Sanko Junyaku, SS1303) added with 0.2% BSA (Sigma)) supplemented with 200 µM 2-ME, 5 mM LiCl, 10 µM SB431542, 10 ng/ml IGF-1, 10 ng/ml HGF and 10 ng/ml bFGF (hereinafter to be referred to as muscle differentiation medium A). After 4 days (25 days after initial day of differentiation induction), the medium was exchanged with SF-03 basic medium supplemented with 200 µM 2-ME, 5 mM LiCl, 10 µM SB431542 and 10 ng/ml IGF-1 (hereinafter to be referred to as muscle differentiation medium B). After 3 days (28 days after initial day of differentiation induction), the medium was exchanged with SF-03 basic medium supplemented with 200 µM 2-ME, 5 mM LiCl, 10 µM SB431542, 10 ng/ml IGF-1 and 10 ng/ml HGF (hereinafter to be referred to as muscle differentiation medium C). Thereafter, the medium was exchanged with muscle differentiation medium C twice per week. After 14 days from changing to muscle differentiation medium C (42 days after initial day of differentiation induction), the medium was exchanged with DMEM basic medium (DMEM (Invitrogen #11960069) added with 1% Penicillin-Streptomycin Mixed Solution, 1% L-gluthamine (Nacalai Tesque #16948-04) and 200 µM 2-ME) supplemented with 2% Horse Serum (HS), 5 µM SB431542 and 10 ng/ml IGF-1 (hereinafter to be referred to as muscle differentiation medium D). Thereafter, the medium was exchanged with muscle differentiation medium D twice per week. Culturing in muscle differentiation medium D was performed up to day 95 at the longest from the start of differentiation induction.

<Production of DNA Template for In Vitro Transcription>

Genes encoding fluorescent proteins (EGFP, tagBFP and tagRFP) were obtained by PCR (20 cycles of 94° C. for 2 min 10 sec and 68° C. for 30 sec, preserved at 15° C.) using pEGFP-N1 (Clontech), pTagBFP-Tubulin (evrogen), or pTAP-tagRFP as a template, and the corresponding primers (TAPEGFP_IVTfwd (SEQ ID NO: 11) and TAP_IVTrev (SEQ ID NO: 14), tagBFP fwd (SEQ ID NO: 12) and TAP_IVTrev, or tagRFP fwd (SEQ ID NO: 13) and TAP_IV-Trev, respectively) and KOD-Plus-Neo (KOD-401, TOYOBO). The PCR products were purified using MiniElute PCR purification Kit (QIAGEN). The PCR products are referred to as fluorescent protein cassette (EGFP cassette (SEQ ID NO: 15), tagBFP cassette (SEQ ID NO: 16), and tagRFP cassette (SEQ ID NO: 17)), respectively.

5'-UTR was amplified by PCR (94° C. for 2 min, followed by 13 cycles of 98° C. for 10 sec and 68° C. for 10 sec, preserved at 15° C.) using IVT_5prime_UTR (IVT_5prime_UTR (SEQ ID NO: 18)) as a template and the corresponding primers (TAP_T7_G3C fwd primer (SEQ ID NO: 19) and Rev5UTR primer (SEQ ID NO: 20)) and KOD-Plus-Neo (KOD-401, TOYOBO). The amplified PCR product was purified using MiniElute PCR purification Kit (QIAGEN). The obtained PCR product is referred to as control 5'-UTR cassette (SEQ ID NO: 21).

The 5'-UTR cassettes having miRNA response sequence are referred to as 5UTR-miR-1 cassette (SEQ ID NO: 22), 5UTR-miR-133 cassette (SEQ ID NO: 23), 5UTR-miR-206 cassette (SEQ ID NO: 24), 5UTR-miR-489 cassette (SEQ ID NO: 25) and 5UTR-miR-708 cassette (SEQ ID NO: 26)), and obtained by DNA synthesis.

3'-UTR was amplified by PCR (94° C. for 2 min, followed by 13 cycles of 98° C. for 10 sec and 68° C. for 10 sec, preserved at 15° C.) using IVT_3prime_UTR (IVT_3prime_UTR (SEQ ID NO: 27)) as a template and the corresponding primers (Fwd3UTR primer (SEQ ID NO: 28) and Rev3UTR2T20 (SEQ ID NO: 29)) and KOD-Plus-Neo (KOD-401, TOYOBO). The amplified PCR product was purified using MiniElute PCR purification Kit (QIAGEN). The obtained PCR product is referred to as 3'-UTR cassette (SEQ ID NO: 30).

The DNA templates for producing mRNA containing control 5'-UTR by in vitro transcription were amplified by PCR (94° C. for 2 min, followed by 20 cycles of 98° C. for 10 sec, 68° C. for 45 sec, preserved at 15° C.) using each fluorescent protein cassette, control 5'-UTR and 3'-UTR cassette generated above, the corresponding primers (TAP_T7_G3C fwd primer and 3UTR120A rev primer (SEQ ID NO: 31)) and KOD-Plus-Neo (KOD-401, TOYOBO) selected as appropriate. The DNA templates for producing mRNA containing each 5'-UTR cassette by in vitro transcription were amplified by PCR (94° C. for 2 min, followed by 20 cycles of 98° C. for 10 sec, 60° C. for 30 sec and 68° C. for 45 sec, preserved at 15° C.) using each fluorescent protein cassette, each 5'-UTR cassette and 3'-UTR cassette generated above, the corresponding primers (GCT7pro_5 UTR2 (SEQ ID NO: 32) and 3UTR120A rev primer) and KOD-Plus-Neo (KOD-401, TOYOBO). The amplified PCR products were purified using MiniElute PCR purification Kit (QIAGEN). The obtained PCR products are referred to as EGFP DNA template (SEQ ID NO: 33), tagBFP DNA template (SEQ ID NO: 34), tagRFP DNA template (SEQ ID NO: 35) miR-206-EGFP DNA template (SEQ ID NO: 36), miR-1-tagBFP DNA template (SEQ ID NO: 37), miR-133-tagBFP DNA template (SEQ ID NO: 38), miR-206-tagBFP DNA template (SEQ ID NO: 39), miR-489-tagBFP DNA template (SEQ ID NO: 40), miR-708-tagBFP DNA template (SEQ ID NO: 41).

<In Vitro Transcription>

Using MEGAscript T7 kit (Ambion) and the DNA template generated above, mRNA was synthesized. In this reaction, pseudouridine-5'-triphosphate and methylcytidine-5'-triphosphate (TriLink BioTechnologies) were used instead of uridine triphosphate and cytidine triphosphate, respectively. Before IVT (mRNA synthesis) reaction, guanidine-5'-triphosphate was 5-fold diluted with Anti Reverse cap Analog (New England Biolabs). The reaction mixture was incubated at 37° C. for 5 hr, TURBO DNase (Amibion) was added, and the mixture was further incubated at 37° C. for 30 min. The obtained mRNA was purified using Favor-Prep Blood/Cultured Cells Total RNA Extraction Column (Favorgen Biotech), and incubated at 37° C. for 30 min using Antarctic phosphatase (New England Biolabs). Thereafter, the mixture was further purified by RNeasy Mini Elute Cleanup Kit (QIAGEN). The obtained mRNAs are referred to as EGFP mRNA (SEQ ID NO: 42), tagBFP mRNA (SEQ ID NO: 43), tagRFP mRNA (SEQ ID NO: 44), miR-206-EGFP switch (SEQ ID NO: 45), miR-1-tagBFP switch (SEQ ID NO: 46), miR-133-tagBFP switch (SEQ ID NO: 47), miR-206-tagBFP switch (SEQ ID NO: 48), miR-489-tagBFP switch (SEQ ID NO: 49), and miR-708-tagBFP switch (SEQ ID NO: 50).

<Analysis Using miRNA Switch> mRNA that suppresses translation of fluorescent protein in response to the expression of miRNA (hereinafter to be referred to as miRNA switch), as well as mRNA encoding the fluorescent protein gene different from encoded within the miRNA-responsive mRNA (hereinafter to be referred to as transfection control) were introduced into each cell. mRNA introduction without seeding cells was performed using Stemfect RNA transfection kit (Stemgent) and according to the following method. In a 1.5 mL tube, Stemfect Transfection Buffer and two kinds of mRNAs were prepared to 12.5 µL, and 1 µL of Stemfect RNA Transfection Reagent and Stemfect Transfection Buffer were prepared to 12.5 μL in another 1.5 mL tube. The prepared two kinds of solutions mentioned above were mixed, and incubated at room temperature for 15 min. The total amount of the mixture was added to a well (24 well plate) in which the cells were cultured, and the cells were incubated 4 hr at 37° C., 5% $CO_2$. Thereafter, the medium was removed, and 500 μL of a medium (DMEM 2% HS) was added to the well. After 24 hr, analysis was performed using fluorescence activated cell sorting (BD, hereinafter FACS). When mRNA is introduced after seeding cells, 200 μL of Accumax (Funakoshi) was added to the cells cultured in a 24 well plate, and the mixture was incubated at 37° C., 5% $CO_2$ for 10-15 min, 500 μL of a medium (DMEM 2% HS) was added, and the mixture was collected in a 15 mL tube, centrifuged at 4° C., 2000 rpm for 10 min, and the supernatant was removed. After addition of 500 μL of a medium and pipetting, cell number was measured by cell Countess (invitrogen), and the cells were diluted as necessary. When the cells were replated in a 24 well plate, the cells were replated at $2 \times 10^5$ cell/well, and when the cells were replated in a 6 well plate, the cells were replated at $1 \times 10^6$ cell/well. Simultaneously with the plating of the cells in a well, a mixture containing the prepared (the above-mentioned method) mRNA was added to the well. The cells were incubated 4 hr at 37° C., 5% $CO_2$. Thereafter, the medium was removed, and a requisite volume of medium (DMEM 2% HS) was added to the well. After 24 hr, analysis was performed using FACS.

<Analysis by FACS>

To the respective analysis target cells was added 200 μL of Accumax (Funakoshi) per well of a 24 well plate (1 mL for 6 well plate), and the mixture was incubated at 37° C., 5% $CO_2$ for 10-15 min. Thereafter, 500 μL of a medium (DMEM 2% HS) was added, the cells were collected in a 15 mL tube, centrifuged at 4° C., 2000 rpm for 10 min, and the supernatant was removed. 200 μL of a medium (DMEM 2% HS) or HBSS was added per well, and the mixture was suspended by pipetting, passed through a filter and used for analysis.

<Quantitative RT-PCR (qRT-PCR)>

Reverse transcription reaction was performed using ReverTra Ace (TOYOBO). PCR was performed using Power SYBR Green PCR Master Mix (Applied Biosystems). For the analysis of the expression level of miRNA, a reverse transcription reaction was performed using TaqMan MicroRNA Reverse Transcription Kit (Applied Biosystems) and PCR was performed using TaqMan Universal PCR Master Mix (Applied Biosystems). The primers used are shown in Table 5.

TABLE 5

| gene name | Fwd primer | Rev primer |
| --- | --- | --- |
| hMyf5 | tcacctcctcagagc aacct (SEQ ID NO: 51) | ggaactagaagcccctggag (SEQ ID NO: 52) |
| hMyoD | acgtgaggacgagca tgtg (SEQ ID NO: 53) | gtgcagcgttgagtgtct (SEQ ID NO: 54) |
| hmyogenin | tgggcgtgtaaggtg tgtaa (SEQ ID NO: 55) | cgatgtactggatggcactg (SEQ ID NO: 56) |
| hPax7 | gggattccctttgga agtgt (SEQ ID NO: 57) | cggcaaagaatcttggagac (SEQ ID NO: 58) |

TABLE 5-continued

| gene name | Fwd primer | Rev primer |
| --- | --- | --- |
| hPax3 | aggaaggaggcagag gaaag (SEQ ID NO: 59) | cagctgttctgctgtgaagg (SEQ ID NO: 60) |
| hb-actin | caccattggcaatga gcggttc (SEQ ID NO: 61) | aggtctttgcggatgtccacgt (SEQ ID NO: 62) |

<Immunostaining>

$1 \times 10^4$ cells sorted by FACS were centrifuged using Cytospin at 1000 rpm for 2 min to allow for adhesion to a slide glass. After drying at room temperature for 30 min by a dryer, 4% PFA (200 μL) was added dropwise, and the cells were fixed by drying at room temperature for 20 min. After drying for 30 min by a dryer, the cells were washed with PBS. Redundant PBS was removed, 5% Blocking one (Nacalai Tesque) (200 μL) was added dropwise, and the mixture was stood at room temperature for 1 hr. A requisite amount of an antibody was prepared by Can Get Signal Solution B (TOYOBO), 100 μL was added dropwise and the mixture was stood at room temperature for 1 hr or at 4° C. overnight. The mixture was washed with PBS-T, requisite amount of an antibody and Hoechst was prepared by Can Get Signal Solution B (TOYOBO), and stood at room temperature for 1 hr. The mixture was washed with PBS-T, 1-2 drops of PermaFlow (TERUMO) were added dropwise, a cover glass was placed thereon, and stood at room temperature for 30 min or longer. The antibodies are shown in Table 6.

TABLE 6

| name | selling source | catalog number |
| --- | --- | --- |
| MyoD (rabbit-monoclonal) | abcam | ab133627 (ER6653-131) |
| Pax7 (mouse-monoclonal) | DSHB | chick Pax7 a.a. 352-523 |
| MHC (mouse-monoclonal) | eBiosciencce | 14-6503 |
| MHC (rabbit-polyclonal) | Santacruz | sc-20641 |
| anti-Mouse-IgG Alexa488 | Life Technologies | A11029 |
| anti-Rabbit IgG Alexa488 | Life Technologies | A11034 |
| anti-Mouse-IgG Alexa568 | Life Technologies | A11031 |
| anti-Rabbit IgG Alexa568 | Life Technologies | A11036 |

<Re-Culture>

$3 \times 10^4$ cells sorted by FACS were seeded in a 48 well plate coated with Matrigel (BD bioscience), and cultured in muscle differentiation medium A. After seeding, the medium was exchanged the next day with muscle differentiation medium A, and thereafter exchanged with muscle differentiation medium A once every 4 days, or the medium was exchanged 5 days later with muscle differentiation medium D. After 7 days, the cells were immunostained with the requisite antibody. The antibodies are shown in Table 6.

<Results>

How the expression of miR-206 reported to be specifically expressed in muscular tissue (The Journal of Cell Biology, 174(5), 677-87, 2006) varies in the differentiation process into skeleton muscle cells by Dox-MYOD1 forced expression was examined by qRT-PCR (FIG. 1A). As a result, it was shown that the expression level of miR-206 increases as the differentiation into skeleton muscle cell is induced by Dox addition. Dox was added to the medium between day 1 and day 7. Since the expression of miR-206 decreased on day 9, it was suggested that the expression of miR-206 is suppressed as the expression of MyoD decreases (PLoS One. 2013 Apr. 23; 8(4):e61540).

mRNA that suppresses translation of EGFP in response to the expression level of miR-206 (miR-206-EGFP switch) and tagBFP mRNA as the transfection control were produced by the aforementioned method (FIG. 1B), introduced into MYOD1-hiPSCs and whether skeletal muscle lineage cells can be sorted was verified (FIG. 1O). miR-206-EGFP switch was transfected into cells cultured for one day without addition of Dox (Dox– Day 1) to find that the ratio between the fluorescence value of co-introduced tagBFP and the fluorescence value of EGFP encoded by miRNA switch was uniform in the cell population (FIG. 1O). In contrast, when miR-206 switch was transfected into cells cultured for 6 days after Dox addition (Dox+ Day 6), the ratio of the fluorescence values of tagBFP and EGFP varied (FIG. 1D). The above suggests that skeletal muscle lineage cells can be sorted by co-transfection of miR-206-EGFP and transfection control (tagBFP mRNA).

Figure 2:
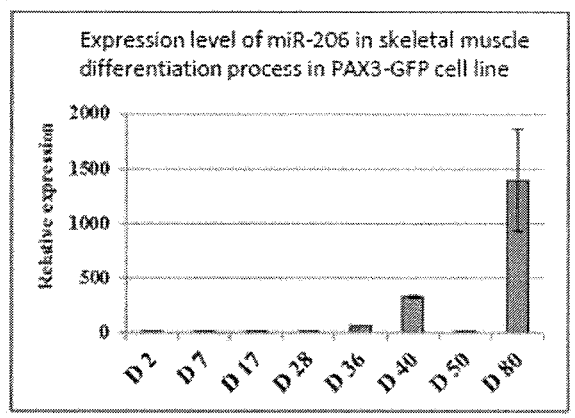
Figure 2:
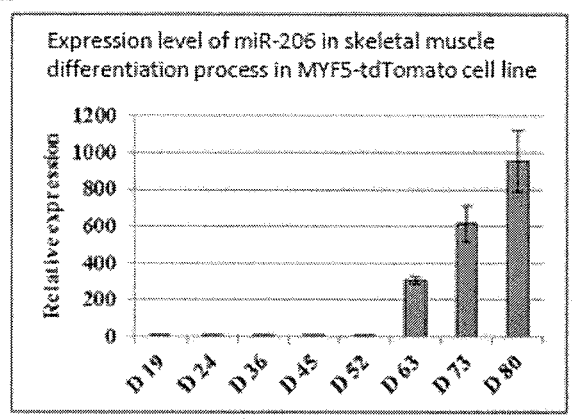
Figure 2:
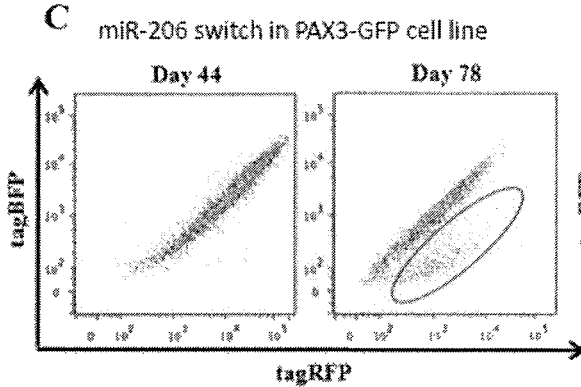
Figure 2:
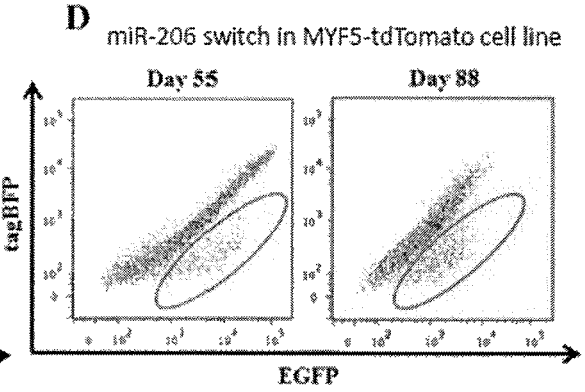
Figure 2:
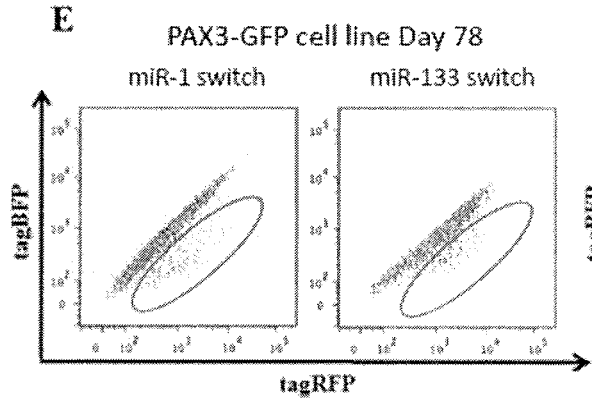
Figure 2:
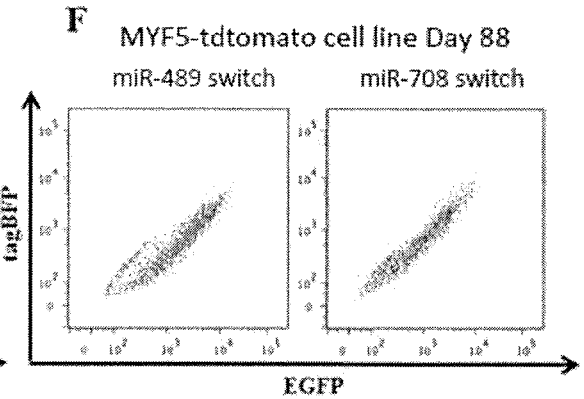

Subsequently, whether skeletal muscle lineage cells can be specifically sorted by miR-206 switch from the cell population obtained from PAX3-GFP iPSCs or MYF5-tdTomato C3 iPSCs by the aforementioned differentiation induction method of skeletal muscle progenitor cells was studied. First, the expression level of miR-206 in the differentiation induction process was examined by qRT-PCR (FIG. 2A and FIG. 2B). As a result, the expression level of miR-206 increased in the differentiation induction process.

Subsequently, whether skeletal muscle lineage cells can be sorted from the cells induced from PAX3-GFP iPSCs, by mRNA of which the tagBFP translation is suppressed in response to the expression level of miR-206 (hereinafter to be referred to as miR-206-tagBFP switch) was studied. In this case, tagRFP mRNA was used as a transfection control. The miR-206-tagBFP switch was transfected into PAX3-GFP iPSCs on day 44 after differentiation induction to find a uniform ratio of fluorescence values of tagBFP and tagRFP in the cell population (FIG. 2C left Figure). In contrast, when transfected into PAX3-GFP iPSCs on day 78 after differentiation induction, the ratio of fluorescence values of tagBFP and tagRFP varied, and the cell population could be separated (FIG. 2C right Figure). From the above, it was suggested that a cell that expresses miR206 was present in the cell population on day 78 after differentiation induction.

Similarly, miR-206-tagBFP switch was transfected into MYF5-tdTomato C3 iPSCs, and whether skeletal muscle lineage cells can be sorted was studied. In this case, EGFP mRNA was used as a transfection control. When miR-206-tagBFP switch was transfected into MYF5-tdTomato C3 iPSCs on day 55 and day 88 after differentiation induction, separation of cell population was suggested (FIG. 2D).

The above results suggest that, in the cell population of skeletal muscle progenitor cells induced to differentiate from PAX3-GFP iPSCs and MYF5-tdTomato C3 iPSCs, cells can be sorted according to the expression level of miR-206 in the cell by using the miR-206-tagBFP switch.

Switches of miRNA-1 and miRNA-133 reported as miRNA relating to skeletal muscle differentiation (Care, A et al. 2007 Nature Medicine. PMID 17468766, Tatsuguchi, M et al. 2007 Journal of Molecular and Cellular Cardiology. PMID 17498736), and miR-489 whose expression in skeletal muscle stem cell has been reported (Cheung, T et al. 2012 Nature. PMID 22358842) and miRNA-708 (Yamaguchi et al. 2012 J Mol Histol. PMID 22562803) were produced and whether similar cell populations appear was verified (FIG. 2E and FIG. 2F). When miRNA-1 switch or miRNA-133 switch was transfected together with the transfection control (tagRFP mRNA) into PAX3-GFP iPSCs on day 78 after differentiation induction, cell populations appeared to be sorted similar to miR-206 switch (FIG. 2E); however, lower responsiveness than miR-206 switch was suggested. On the other hand, when miR-489 switch, miR-708 switch were transfected together with the transfection control (EGFP mRNA) into MYF5-tdTomato C3 iPSCs on day 88 after differentiation induction, population responding to the switch was not found (FIG. 2F).

The above results suggest that skeletal muscle lineage cells can be sorted from the cell population with high efficiency by using miR-206, miRNA-1 and miRNA-133 as indices.

Two cell populations separated by miR-206-tagBFP switch responsiveness were isolated by soating using FACS, and the cells were evaluated by qRT-PCR. In this case, miR-206 switch was introduced together with the transfection control into PAX3-GFP iPSCs on day 84 after differentiation induction, and the cells were sorted based on the responsiveness to miR-206– tagBFP switch into two cell populations (cell population that responded to miR-206-tagBFP switch (hereinafter miR-206+) and cell population that did not respond to miR-206 switch (hereinafter miR-206–)) (FIG. 3A).

Figure 3:
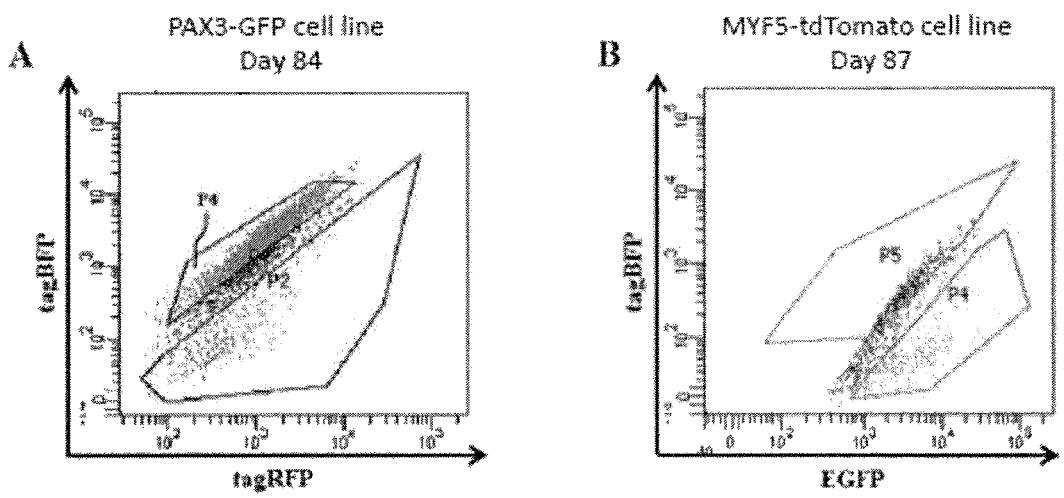
FIG. 3A shows dot plot after transfection of miR-206 switch into the cells on day 84 of differentiation induction of PAX3-GFP iPSCs.
FIG. 3B shows dot plot after transfection of miR-206 switch into the cells on day 87 of differentiation induction of MYF5-tdTomato C3 iPSCs.
FIG. 3C shows the results of quantification, by qRT-PCR, of the gene expression of MYF5 in the cell populations of miR-206+ fraction (corresponding to FIG. 3A, P2) and miR-206− fraction (corresponding to FIG. 3A, P4) sorted by miR-206 switch, on day 84 of differentiation induction of PAX3-GFP iPSCs.
FIG. 3D shows the results of quantification, by qRT-PCR, of the gene expression of MYOD1 in the cell populations of miR-206+ fraction and miR-206− fraction on day 84 of differentiation induction of PAX3-GFP iPSCs.
FIG. 3E shows the results of quantification, by qRT-PCR, of the gene expression of MYOGENIN in the cell populations of miR-206+ fraction and miR-206− fraction on day 84 of differentiation induction of PAX3-GFP iPSCs.
FIG. 3F shows the results of quantification, by qRT-PCR, of the gene expression of MYF5 in miR-206+ fraction (corresponding to FIG. 3B, P4) and miR-206− fraction (corresponding to FIG. 3B, P5) sorted by miR-206 switch, on day 87 of differentiation induction of Myf5-tdTomato C3 iPSCs.
FIG. 3G shows the results of quantification, by qRT-PCR, of the gene expression of MYOD1 in the cell populations of miR-206+ fraction and miR-206− fraction on day 87 of differentiation induction of Myf5-tdTomato C3 iPSCs.
FIG. 3H shows the results of quantification, by qRT-PCR, of the gene expression of MYOGENIN in the cell populations of miR-206+ fraction and miR-206− fraction on day 87 of differentiation induction of Myf5-tdTomato C3 iPSCs.
Figure 3:
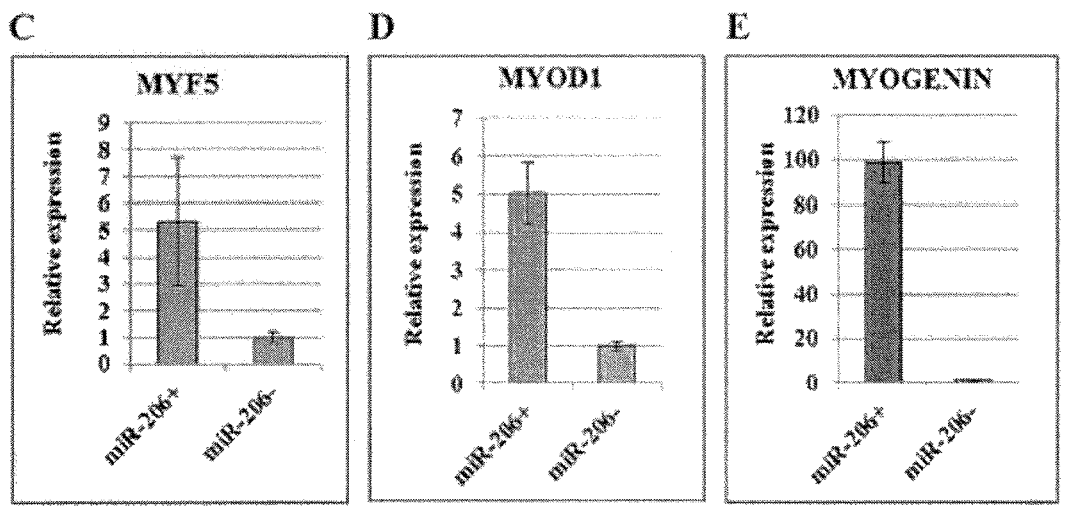
Figure 3:
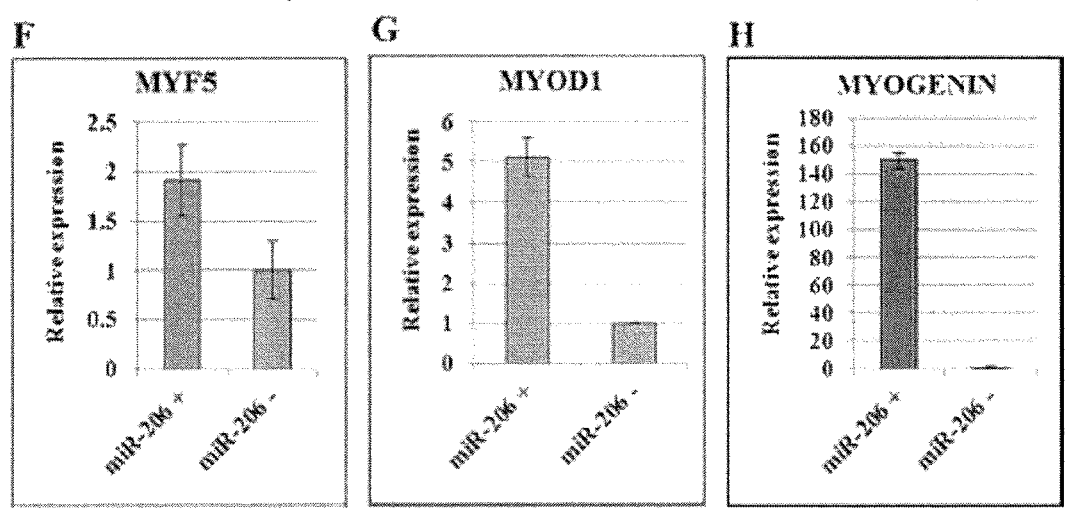

Similarly, miR-206 switch was introduced together with the transfection control into MYF5-tdTomato C3 iPSCs on day 87 after differentiation induction and the cells were sorted (FIG. 3B).

As a result, it was shown that the expression level of genes, MYF5, MYOD1 and MYOGENIN, involved in skeletal muscle differentiation, is increased in sorted miR-206+ than the expression level in miR-206–, in the cell population of skeletal muscle progenitor cells induced from PAX3-GFP iPSCs and MYF5-tdTomato C3 iPSCs (FIG. 3C to FIG. 3H).

The above results show that skeletal muscle lineage cells can be specifically sorted using miR-206 switch.

Figure 4:
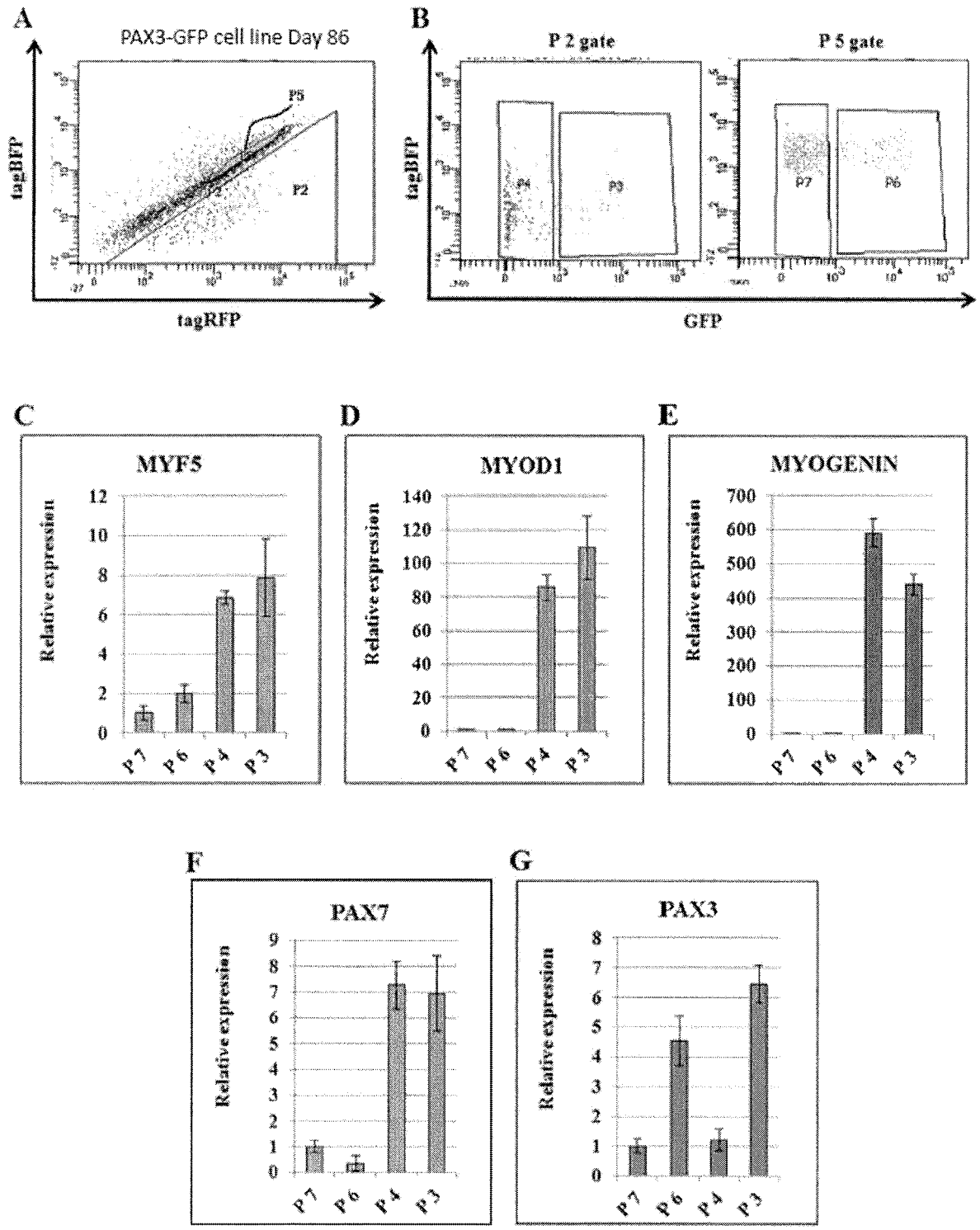
FIG. 4A shows dot plot after transfection of miR-206 switch into PAX3-GFP iPSCs on day 86 of differentiation induction.
FIG. 4B shows dot plot with the horizontal axis sorted out by GFP in each of miR-206+ fraction (corresponding to FIG. 4A, P2) and miR-206− fraction (corresponding to FIG. 4A, P5).
FIG. 4C shows the results of quantification of the expression of MYF5 by qRT-PCR.
FIG. 4D shows the results of quantification of the expression of MYOD1 by qRT-PCR.
FIG. 4E shows the results of quantification of the expression of MYOGENIN by qRT-PCR.
FIG. 4F shows the results of quantification of the expression of PAX7 by qRT-PCR.
FIG. 4G shows the results of quantification of the expression of PAX3 by qRT-PCR. In each graph of FIG. 4B to FIG. 4G, P 7, P 6, P 4, P 3 mean miR-206−/GFP−, miR-206−/GFP+, miR-206+/GFP− and miR-206+/GFP+, respectively.

To study whether miR206+ population contains skeletal muscle progenitor cell, miR-206 switch was introduced together with the transfection control into PAX3-GFP iPSCs on day 86 after differentiation induction, the cells were separated into two based on the responsiveness to miR-206 switch, and the two cell populations were further sorted based on GFP positive and negative (FIG. 4A and FIG. 4B). It was shown that the expression levels of MYF5, MYOD1, MYOGENIN, PAX7 genes increased more in miR-206+ and GFP positive (P3 gate, hereinafter miR-206+/PAX3+) and miR-206+ and GFP negative (P4 gate, hereinafter miR-206+/PAX3–) than in miR-206– and GFP positive (P6 gate, hereinafter miR-206–/PAX3+) and miR-206– and GFP negative (P7 gate, hereinafter miR-206–/PAX3–) (FIG. 4C to FIG. 4F).

Figure 5:
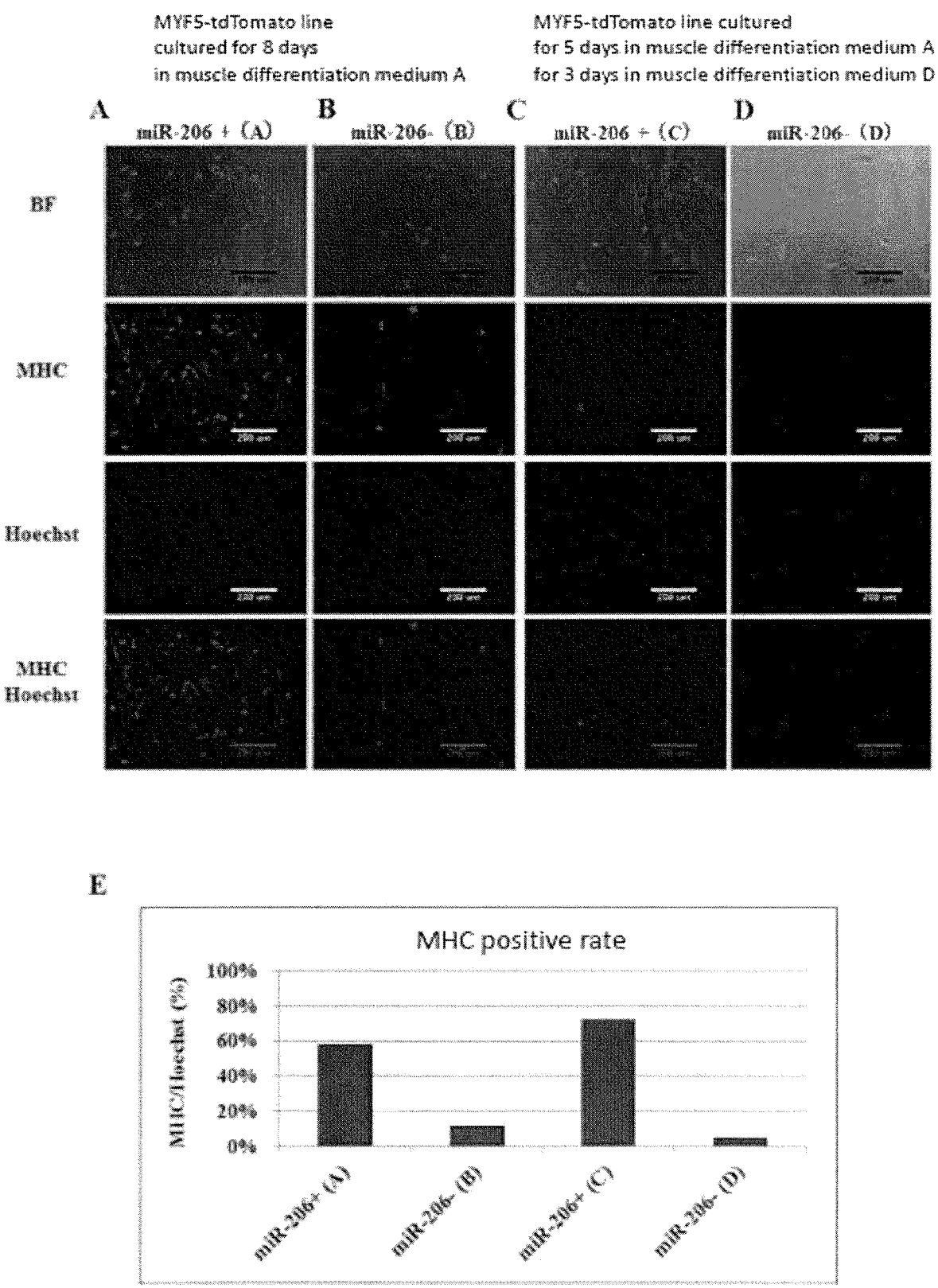
FIG. 5A shows fluorescence images of cells cultured for 8 days after isolation of miR-206 fraction on day 95 of differentiation induction of MYF5-tdTomato C3 iPSCs, and stained with MHC antibody and Hoechst (miR-206+ (A)).
FIG. 5B shows fluorescence images of cells cultured for 8 days after isolation of miR-206 fraction on day 95 of differentiation induction of MYF5-tdTomato C3 iPSCs, and stained with MHC antibody and Hoechst (miR-206− (B)).
FIG. 5C shows fluorescence images of cells cultured for 8 days (cultured for skeletal muscle progenitor cell for 5 days and cultured for skeletal muscle differentiation for 3 days) after isolation of miR-206+ fraction on day 95 of differentiation induction of MYF5-tdTomato C3 iPSCs, and stained with MHC antibody and Hoechst (miR-206+ (C)).
FIG. 5D shows fluorescence images of cells cultured for 8 days (cultured for skeletal muscle progenitor cell for 5 days and cultured for skeletal muscle differentiation for 3 days) after isolation of miR-206− fraction on day 95 of differentiation induction of MYF5-tdTomato C3 iPSCs, and stained with MHC antibody and Hoechst(miR-206− (D)).
FIG. 5E shows MHC positive rates of miR-206+ (A), miR-206− (B), miR-206+ (C) and miR-206− (D). The MHC positive rate is shown as a ratio of the number of MHC positive cells to the number of cells stained with Hoechst.
Figure 6:
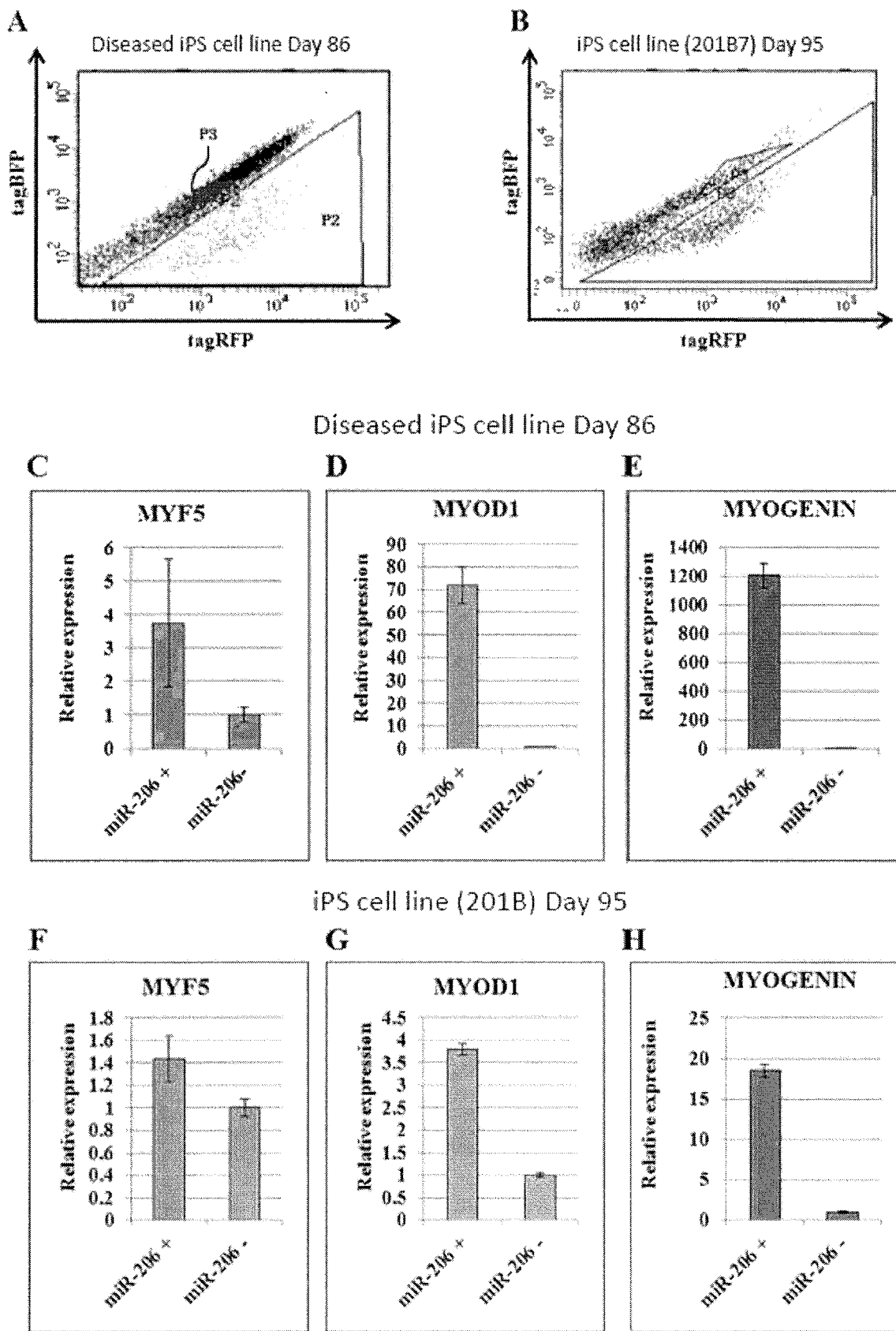
FIG. 6A shows dot plot after transfection of miR-206 switch into the cells on day 86 of differentiation induction of diseased iPS cell line.
FIG. 6B shows dot plot after transfection of miR-206 switch into the cells on day 95 of differentiation induction of 201B7.
FIG. 6C shows the results of quantification, by qRT-PCR, of the gene expression of MYF5 in miR-206+ fraction (corresponding to FIG. 6A, P2) and miR-206− fraction (corresponding to FIG. 6A, P3) sorted by miR-206 switch, on day 86 of differentiation induction of diseased iPS cell line.
FIG. 6D shows the results of quantification, by qRT-PCR, of the gene expression of MYOD1 in the cell populations of miR-206+ and miR-206− on day 86 of differentiation induction of diseased iPS cell line.
FIG. 6E shows the results of quantification, by qRT-PCR, of the gene expression of MYOGENIN in miR-206+ and miR-206− on day 86 of differentiation induction of diseased iPS cell line.
FIG. 6F shows the results of quantification, by qRT-PCR, of the gene expression of MYF5 in the cell populations of miR-206+ fraction and miR-206− fraction sorted by miR-206 switch, on day 95 of differentiation induction of 201B7.
FIG. 6G shows the results of quantification, by qRT-PCR, of the gene expression of MYOD1 in the cell populations of miR-206+ cell population and miR-206− cell population on day 95 of differentiation induction of 201B7.
FIG. 6H shows the results of quantification, by qRT-PCR, of the gene expression of MYOGENIN in the cell populations of miR-206+ fraction and miR-206− fraction on day 95 of differentiation induction of 201B7.

Then, cells expressing miR-206 were isolated (miR-206+ fraction), reseeded, and whether they are induced to differentiate into skeleton muscle cells was confirmed (FIG. 5A and FIG. 5E). MYF5-tdTomato cell line on day 95 after differentiation induction was sorted by miR-206 switch, miR-206+ fraction and fraction other than the cells sorted by miR-206 switch (miR-206– fraction) were reseeded in a Matrigel-coated 48 well plate and cultured for 8 days. The cells were cultured separately in a well containing muscle differentiation medium A for 8 days (FIG. 5A and FIG. 5B) or in a well containing muscle differentiation medium A for 5 days and then in muscle differentiation medium D for 3 days (FIG. 5C and FIG. 5D), and the cells were immunostained. Expression of Myosin Heavy Chain (hereinafter MHC) protein in miR-206+ fraction was confirmed (FIG. 5A and FIG. 5C), and slight expression of MHC protein was found in miR-206− fraction (FIG. 5B and FIG. 5D). The positive rate of MHC to the stained nucleus was about 60% in the miR-206+ population, and about 5% in the miR-206− population (FIG. 5E). These results suggest that miR-206+ population contains many skeletal muscle lineage cells having differentiation potency into skeleton muscle cells, and that miR-206− population contains many cells that do not have differentiation potency into skeleton muscle cells.

When a cell transplantation treatment is performed, it is necessary to induce differentiation using iPS cells free of genome modification. Subsequently, whether skeletal muscle lineage cells can be sorted similarly by miR-206 switch not only in cell line as reporter line but also in diseased iPS cell line and 201B7 free of genome modification was investigated. In diseased iPS cell line and cells induced from 201B7 (each on day 86 and day 95 after induction), similarly, skeletal muscle lineage cells were sorted by miR-206 switch (FIGS. 6A and B), subjected to qRT-PCR analysis, and the expression level of genes involved in skeletal muscle differentiation was examined (FIG. 6C to FIG. 6H). It was shown that the expression levels of MYF5 (FIG. 6C and FIG. 6F), MYOD1 (FIG. 6D and FIG. 6G), MYOGENIN (FIG. 6E and FIG. 6H) increased in miR-206+ also in the iPS cell line. The above results suggest that skeletal muscle lineage cells can be sorted by miR-206 switch also in the diseased iPS cell line and 201B7, and the sorted skeletal muscle lineage cell population contains skeletal muscle progenitor cells.

Figure 7:
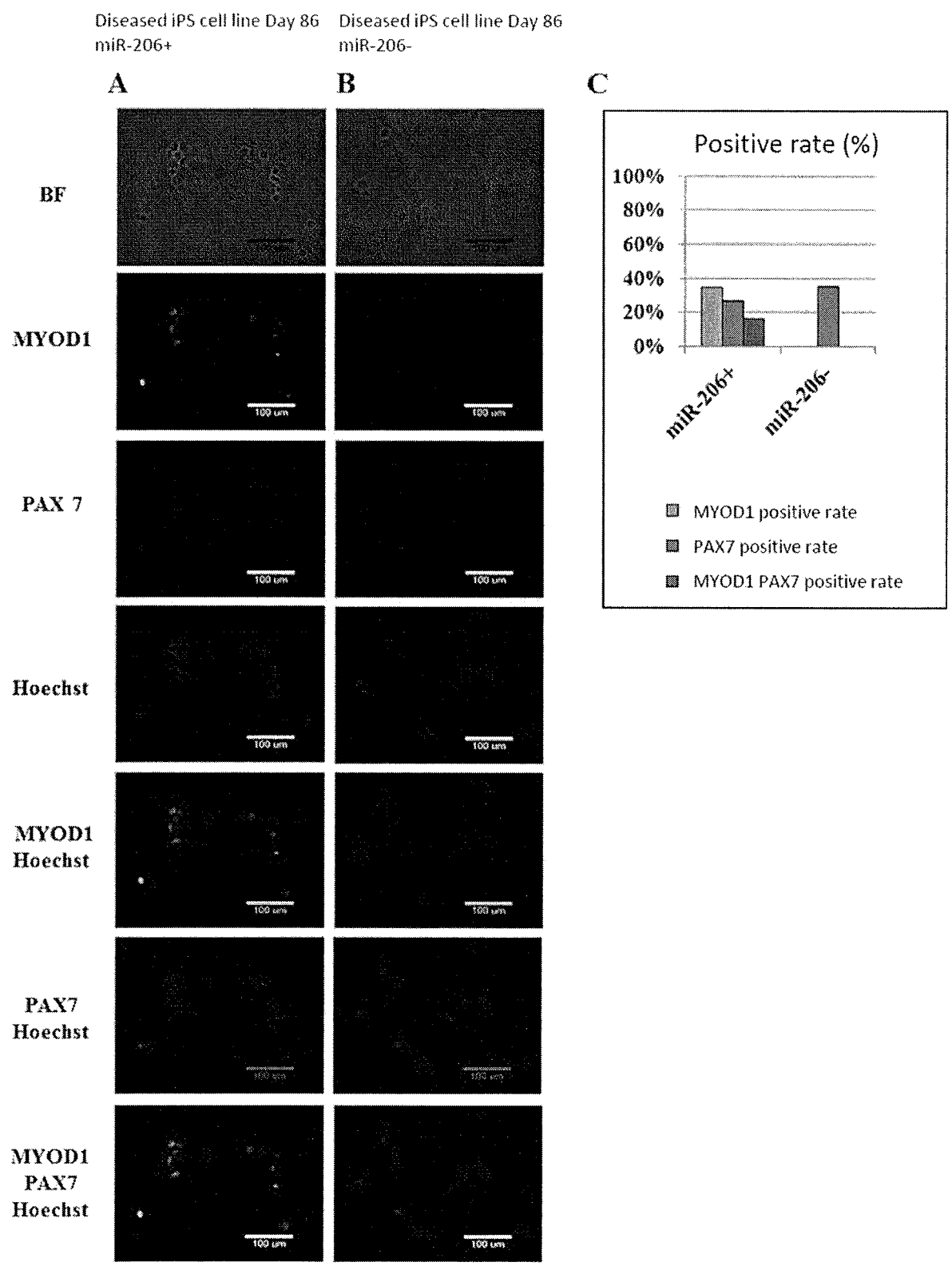
FIG. 7A shows fluorescence images of miR-206+ fraction on day 86 of differentiation induction of diseased iPS cell line and stained with antibodies to against MYOD1 and PAX7, and Hoechst.
FIG. 7B shows fluorescence images of cell population of miR-206− on day 86 of differentiation induction of diseased iPS cell line and stained with antibodies to against MYOD1 and PAX7, and Hoechst.
FIG. 7C is a graph showing MYOD1 positive rate, PAX7 positive rate, and MYOD1+PAX7 double positive rate of miR-206+ and miR-206−. Each positive rate is shown as a ratio of the number of positive cells to the number of cells stained with Hoechst.

Then, to confirm expression of MYOD1 and PAX7 observed in skeletal muscle progenitor cells also at the protein level, diseased iPS cell line after differentiation induction (day 86 after induction) was sorted by miR-206 switch, and the cells after soating were immunostained. As a result, expression of MYOD1 and PAX7 was confirmed in miR-206+ fraction (FIG. 7A). Furthermore, a cell expressing both MYOD1 and PAX7 proteins was found in miR-206+ fraction (FIG. 7C). In contrast, expression of MYOD1 was not found in miR-206− fraction, and slight expression of PAX7 was found (FIG. 7B). The above results suggest that miR-206 positive skeletal muscle lineage cell population sorted by miR-206 switch may contain a skeletal muscle progenitor cell having regenerative ability.

INDUSTRIAL APPLICABILITY

According to the present invention, skeletal muscle progenitor cells can be selectively obtained from pluripotent stem cells, and a therapeutic agent for myopathy containing the skeletal muscle progenitor cell can be provided. Particularly, a skeletal muscle progenitor cell differentiated from an iPS cell derived from the patient's own somatic cell can be provided as a skeletal muscle progenitor cell for the treatment of hereditary myopathies.

This application is based on a patent application No. 2015-005447 filed in Japan on Jan. 14, 2015, the contents of which are incorporated in full herein.

The invention claimed is:

1. A method of sorting a mammalian skeletal muscle progenitor cell, comprising the following steps (A) and (B):
   (A) a step of introducing miRNA-responsive mRNA into mammalian cells of a cell population that contains or may contain a mammalian skeletal muscle progenitor cell in the form of a synthetic mRNA molecule, wherein the miRNA-responsive mRNA consists of a sequence comprising the following:
      (i) a nucleic acid comprising a sequence specifically recognized by miRNA specifically expressed in a mammalian skeletal muscle progenitor cell selected from the group consisting of miR-1, miR-133, and miR206, and
      (ii) a nucleic acid comprising a sequence encoding a marker protein,
      wherein the nucleic acid of (ii) is functionally linked to the nucleic acid of (i) such that hybridization of the miRNA to the nucleic acid of (i) suppresses translation of the marker protein, and
      wherein the nucleic acid of (i) is in the 5' UTR of the miRNA-responsive mRNA, and
   (B) a step of sorting cells in which the translation of the marker protein is suppressed from the cell population.

2. The method according to claim 1, wherein the aforementioned (i) and (ii) are linked in the direction of from 5' to 3'.

3. The method according to claim 1, wherein the miRNA specifically expressed in a skeletal muscle progenitor cell of the aforementioned (i) is miR-206.

4. The method according to claim 1, wherein the marker protein of the aforementioned (ii) is one or more genes selected from the group consisting of a fluorescent protein, an apoptosis induction protein and a protein encoded by a suicide gene.

5. The method according to claim 4, wherein the marker protein of the aforementioned (ii) is a fluorescent protein, and the method further comprises introducing control mRNA into cells of the cell population.

6. The method according to claim 5, further comprising comparing a translation level of the control mRNA with that of the miRNA-responsive mRNA.

7. The method according to claim 1, wherein the marker protein of the aforementioned (ii) is an apoptosis induction protein or a protein encoded by a suicide gene, wherein the sorting is carried out by death of cells other than skeletal muscle progenitor cells.

8. The method according to claim 1, wherein the aforementioned cell population is a population of cells obtained by differentiation induction of mammalian pluripotent stem cells into skeletal muscle progenitor cells.

9. A method of sorting a mammalian skeletal muscle progenitor cell, comprising the following steps (A) and (B):
   (A) a step of introducing miRNA-responsive mRNA into mammalian cells of a population of cells obtained by differentiation induction of mammalian pluripotent stem cells into skeletal muscle progenitor cells, wherein the miRNA-responsive mRNA consists of a sequence comprising the following:
      (i) a nucleic acid comprising a sequence specifically recognized by miRNA specifically expressed in a mammalian skeletal muscle progenitor cell selected from the group consisting of miR-1, miR-133, and miR206, and (ii) a nucleic acid comprising a sequence encoding a marker protein, wherein the nucleic acid of (ii) is functionally linked to the nucleic acid of (i) such that hybridization of the miRNA to the nucleic acid of (i) suppresses translation of the marker protein, and (B) a step of sorting cells in which the translation of the marker protein is suppressed from the cell population, wherein the aforementioned differentiation induction of pluripotent stem cells into skeletal muscle progenitor cells comprises the following steps (1) to (5):

(1) a step of culturing mammalian pluripotent stem cells in a culture medium containing a TGF-β inhibitor and a GSK3β inhibitor, (2) a step of culturing the cells obtained in the step of (1) in a culture medium containing a TGF-β inhibitor, a GSK3β inhibitor, IGF1, HGF and bFGF, (3) a step of culturing the cells obtained in the step of (2) in a culture medium containing a TGF-β inhibitor, a GSK3β inhibitor and IGF1, (4) a step of culturing the cells obtained in the step of (3) in a culture medium containing a TGF-β inhibitor, IGF1 and HGF, and (5) a step of culturing the cells obtained in the step of (4) in a culture medium containing a TGF-β inhibitor, IGF1 and serum.

10. The method according to claim 9, wherein the TGF-β inhibitor in the aforementioned steps (1) to (5) is SB431542, the GSK3β inhibitor in the aforementioned Step (1) is CHIR99021, and the GSK3β inhibitor in the aforementioned steps (2) and (3) is LiCl.

11. The method according to claim 9, wherein the serum in the aforementioned Step (5) is horse serum.

12. A method of producing a population of skeletal muscle progenitor cells from a mammalian pluripotent stem cell, comprising the following steps (1) to (3):

(1) a step of inducing differentiation of a mammalian pluripotent stem cell clone into skeletal muscle progenitor cells, (2) a step of introducing miRNA-responsive mRNA in the form of a synthetic mRNA molecule comprising the following (i) and (ii) into the cells obtained in the step of (1):

(i) a nucleic acid having a sequence specifically recognized by miRNA specifically expressed in a skeletal muscle progenitor cell selected from the group consisting of miR-1, miR-133, and miR206, (ii) a nucleic acid encoding a marker protein, wherein the nucleic acid of (ii) is functionally linked to the nucleic acid of (i) such that hybridization of the miRNA to the nucleic acid of (i) suppresses translation of the marker protein, and wherein the nucleic acid of (i) is in the 5' UTR of the miRNA-responsive mRNA, and (3) a step of selecting a cell having a small translation amount of the aforementioned marker protein or incapable of detection thereof.

13. The method according to claim 12, wherein the aforementioned (i) and (ii) are linked in the direction of from 5' to 3'.

14. The method according to claim 12, wherein the miRNA specifically expressed in a mammalian skeletal muscle progenitor cell of the aforementioned (i) is miR-206.

15. The method according to claim 12, wherein the marker protein of the aforementioned (ii) is one or more genes selected from the group consisting of a fluorescent protein, an apoptosis induction protein and a protein encoded by a suicide gene.

16. The method according to claim 15, wherein the marker protein of the aforementioned (ii) is a fluorescent protein, wherein the method further comprises introducing control mRNA into the cells obtained in the step of (1), and the aforementioned Step (3) is a step of selecting a cell further characterized in that translation of a protein encoded by the control mRNA is not suppressed.

17. The method according to claim 12, wherein the marker protein of the aforementioned (ii) is an apoptosis induction protein or a protein encoded by a suicide gene, wherein the selection is carried out by death of cells other than skeletal muscle progenitor cells.

18. A method of producing a population of skeletal muscle progenitor cells from a mammalian pluripotent stem cell, comprising the following steps (1) to (3):

(1) a step of inducing differentiation of a mammalian pluripotent stem cell clone into skeletal muscle progenitor cells, (2) a step of introducing miRNA-responsive mRNA comprising the following (i) and (ii) into the cells obtained in the step of (1):

(i) a nucleic acid having a sequence specifically recognized by miRNA specifically expressed in a skeletal muscle progenitor cell selected from the group consisting of miR-1, miR-133, and miR206, (ii) a nucleic acid encoding a marker protein, wherein the nucleic acid of (ii) is functionally linked to the nucleic acid of (i) such that hybridization of the miRNA to the nucleic acid of (i) suppresses translation of the marker protein, and (3) a step of selecting a cell having a small translation amount of the aforementioned marker protein or incapable of detection thereof, wherein the aforementioned Step (1) comprises the following steps (1-1) to (1-5):

(1-1) a step of culturing mammalian pluripotent stem cells in a culture medium containing a TGF-β inhibitor and a GSK3β inhibitor, (1-2) a step of culturing the cells obtained in the step of (1-1) in a culture medium containing a TGF-β inhibitor, a GSK3β inhibitor, IGF1, HGF and bFGF, (1-3) a step of culturing the cells obtained in the step of (1-2) in a culture medium containing a TGF-β inhibitor, a GSK3β inhibitor and IGF1, (1-4) a step of culturing the cells obtained in the step of (1-3) in a culture medium containing a TGF-β inhibitor, IGF1 and HGF, and (1-5) a step of culturing the cells obtained in the step of (1-4) in a culture medium containing a TGF-β inhibitor, IGF1 and serum.

19. The method according to claim 18, wherein the TGF-β inhibitor in the aforementioned steps (1-1) to (1-5) is SB431542, the GSK3β inhibitor in the aforementioned step (1-1) is CHIR99021, and the GSK3β inhibitor in the aforementioned steps (1-2) and (1-3) is LiCl.

20. The method according to claim 18, wherein the serum in the aforementioned step (1-5) is horse serum.

\* \* \* \* \*